United States Patent
Rottensteiner et al.

(10) Patent No.: US 12,091,675 B2
(45) Date of Patent: Sep. 17, 2024

(54) GENE THERAPY OF HEMOPHILIA A USING VIRAL VECTORS ENCODING RECOMBINANT FVIII VARIANTS WITH INCREASED EXPRESSION

(71) Applicant: Takeda Pharmaceutical Company Limited, Osaka (JP)

(72) Inventors: Hanspeter Rottensteiner, Vienna (AT); Werner Hoellriegl, Altenmarkt/Triesting (AT)

(73) Assignee: Takeda Pharmaceutical Company Limited, Osaka (JP)

( * ) Notice: Subject to any disclaimer, the term of this patent is extended or adjusted under 35 U.S.C. 154(b) by 701 days.

(21) Appl. No.: 17/296,944

(22) PCT Filed: Jul. 15, 2019

(86) PCT No.: PCT/US2019/041802
§ 371 (c)(1),
(2) Date: May 25, 2021

(87) PCT Pub. No.: WO2020/018419
PCT Pub. Date: Jan. 23, 2020

(65) Prior Publication Data
US 2022/0333135 A1    Oct. 20, 2022

Related U.S. Application Data

(60) Provisional application No. 62/698,680, filed on Jul. 16, 2018, provisional application No. 62/867,171, filed on Jun. 26, 2019.

(51) Int. Cl.
| | |
|---|---|
| *C12N 15/861* | (2006.01) |
| *A61K 38/37* | (2006.01) |
| *A61K 48/00* | (2006.01) |
| *C07K 14/755* | (2006.01) |

(52) U.S. Cl.
CPC ............ *C12N 15/861* (2013.01); *A61K 38/37* (2013.01); *A61K 48/0083* (2013.01); *C07K 14/755* (2013.01); *A01K 2217/075* (2013.01); *A01K 2227/105* (2013.01); *A01K 2267/0381* (2013.01)

(58) Field of Classification Search
None
See application file for complete search history.

(56) References Cited

U.S. PATENT DOCUMENTS

| | | |
|---|---|---|
| 4,797,368 A | 1/1989 | Carter et al. |
| 4,868,112 A | 9/1989 | Toole, Jr. |
| 5,112,950 A | 5/1992 | Meulien et al. |
| 5,139,941 A | 8/1992 | Muzyczka et al. |
| 5,171,844 A | 12/1992 | Van Ooyen et al. |
| 5,543,502 A | 8/1996 | Nordfang et al. |
| 5,595,886 A | 1/1997 | Chapman et al. |
| 5,610,278 A | 3/1997 | Nordfang et al. |
| 5,789,203 A | 4/1998 | Chapman et al. |
| 5,935,935 A | 8/1999 | Connelly et al. |
| 5,972,885 A | 10/1999 | Spira et al. |
| 5,994,136 A | 11/1999 | Naldini et al. |
| 6,013,516 A | 1/2000 | Verma et al. |
| 6,048,720 A | 4/2000 | Dalborg et al. |
| 6,060,447 A | 5/2000 | Chapman et al. |
| 6,114,148 A | 9/2000 | Seed et al. |
| 6,200,560 B1 | 3/2001 | Couto et al. |
| 6,228,620 B1 | 5/2001 | Chapman et al. |
| 6,316,226 B1 | 11/2001 | Van Ooyen et al. |
| 6,346,513 B1 | 2/2002 | Van Ooyen et al. |
| 6,458,563 B1 | 10/2002 | Lollar |
| 6,649,375 B2 | 11/2003 | Connelly et al. |
| 6,818,439 B1 | 11/2004 | Jolly et al. |
| 6,924,365 B1 | 8/2005 | Miller et al. |
| 7,041,635 B2 | 5/2006 | Kim et al. |
| 7,635,763 B2 | 12/2009 | Lollar |
| 7,943,374 B2 | 5/2011 | Hildinger |
| 7,973,374 B2 | 7/2011 | Jeong |
| 8,188,246 B2 | 5/2012 | Lollar |
| 8,519,111 B2 | 8/2013 | Lollar |
| 8,986,991 B2 | 3/2015 | Denning et al. |
| 9,393,323 B2 | 7/2016 | Nathwani et al. |
| 9,447,168 B2 | 9/2016 | Nathwani et al. |
| 9,504,762 B2 | 11/2016 | Colosi et al. |
| 10,421,798 B2 | 9/2019 | Schellenberger et al. |

(Continued)

FOREIGN PATENT DOCUMENTS

| | | |
|---|---|---|
| WO | WO 2003/052051 A3 | 6/2003 |
| WO | WO 2007/149852 A2 | 12/2007 |

(Continued)

OTHER PUBLICATIONS

International Search Report with Written Opinion corresponding to International Patent Application No. PCT/US2019/041802, dated Dec. 9, 2019, 18 pages.

(Continued)

*Primary Examiner* — Robert M Kelly
(74) *Attorney, Agent, or Firm* — Morgan, Lewis & Bockius LLP

(57) ABSTRACT

The present disclosure provides, among other aspects, codon-altered polynucleotides encoding Factor VIII variants for expression in mammalian cells. In some embodiments, the disclosure also provides mammalian gene therapy vectors and methods for treating hemophilia A. In some embodiments, the present disclosure provides methods for dosing a hemophilia A patient with a polynucleotide, e.g., a codon-altered polynucleotide, encoding a Factor VIII polypeptide.

8 Claims, 28 Drawing Sheets
Specification includes a Sequence Listing.

(56) References Cited

U.S. PATENT DOCUMENTS

| | | |
|---|---|---|
| 2005/0003482 A1 | 1/2005 | Fang et al. |
| 2006/0099685 A1 | 5/2006 | Yallop et al. |
| 2011/0184049 A1 | 7/2011 | Chuah et al. |
| 2012/0178691 A1 | 7/2012 | Schellenberger et al. |
| 2013/0017997 A1 | 1/2013 | Schellenberger et al. |
| 2013/0024960 A1 | 1/2013 | Nathwani et al. |
| 2013/0202596 A1 | 8/2013 | Salas et al. |
| 2013/0211380 A1 | 8/2013 | Cabrera Aquino et al. |
| 2014/0370035 A1 | 12/2014 | Jiang et al. |
| 2015/0023959 A1 | 1/2015 | Chhabra et al. |
| 2015/0038421 A1 | 2/2015 | Schellenberger et al. |
| 2015/0071883 A1 | 3/2015 | Colosi et al. |
| 2015/0158929 A1 | 6/2015 | Schellenberger et al. |
| 2015/0158930 A1 | 6/2015 | Nathwani et al. |
| 2015/0283267 A1 | 10/2015 | Vandendriessche et al. |
| 2015/0361158 A1 | 12/2015 | Tan et al. |
| 2016/0030524 A1 | 2/2016 | Wang et al. |
| 2016/0102133 A1 | 4/2016 | Xiao et al. |
| 2016/0229904 A1 | 8/2016 | Xiao |
| 2016/0251409 A1 | 9/2016 | Oestergaard et al. |
| 2017/0049859 A1 | 2/2017 | Nathwani et al. |
| 2017/0095538 A1 | 4/2017 | Colosi et al. |
| 2017/0233455 A1 | 8/2017 | Falkner et al. |
| 2019/0194295 A1 | 6/2019 | Falkner et al. |
| 2021/0403948 A1 | 12/2021 | Chuah et al. |

FOREIGN PATENT DOCUMENTS

| | | |
|---|---|---|
| WO | WO 2008/069942 A2 | 6/2008 |
| WO | WO 2008/077616 A1 | 7/2008 |
| WO | WO 2013/016454 A1 | 1/2013 |
| WO | WO 2013/123503 A1 | 8/2013 |
| WO | WO 2013/151666 A2 | 10/2013 |
| WO | WO 2013/186563 A2 | 12/2013 |
| WO | WO 2014/064277 A3 | 5/2014 |
| WO | WO 2014/127215 A1 | 8/2014 |
| WO | WO 2015/038625 A1 | 3/2015 |
| WO | WO 2016/025764 A2 | 2/2016 |
| WO | WO 2016/146757 A1 | 9/2016 |
| WO | WO 2017053677 A1 | 3/2017 |
| WO | WO 2017083762 A1 | 5/2017 |
| WO | WO 2020/018419 A1 | 1/2020 |

OTHER PUBLICATIONS

International Search Report with Written Opinion corresponding to International Patent Application No. PCT/US20/13722, dated Jul. 23, 2020, 9 pages.

International Search Report with Written Opinion corresponding to International Patent Application No. PCT/US20/64375, dated Jun. 28, 2021, 19 pages.

Nair et al: "Computationally designed liver-specific transcriptional modules and hyperactive factor IX improve hepatic gene therapy", 15 Blood, May 2014 (May 15, 2014), pp. 3195-3199, XP055281944, DOI: 10.1182/blood-2013-10-534032 Retrieved from the Internet: URL:http://www.bloodjournal.org/content/12 3/20/3195.full.pdf.

Tsuzuki et al: "The Journal of Biological Chemistry 0 1985 by the American Society of Biological Chemists Structure of the Human Prealbumin Gene*", Oct. 5, 1985 (Oct. 5, 1985), pp. 12224-12227, XP55685725, Retrieved from the Internet: URL:https://www.jbc.org/content/260/22/12224.full.pdfw#page= l&view=FitH.

Altschul et al. (1990) "Basic local alignment search tool," Journal of molecular biology. 215(3):403-410.

Altschul et al. (1996) "Local alignment statistics," Methods in enzymology. 266(2):460-480.

Altschul et al. (1997) "Gapped BLAST and PSI-BLAST: a new generation of protein database search programs," Nucleic acids research. 25(17):3389-3402.

Aponte-Ubillus et al. (2018) "Molecular design for recombinant adeno-associated virus (rAAV) vector production," Applied microbiology and biotechnology. 102(3):1045-1054.

Asokan et al. "The AAV Vector Toolkit: Poised at the Clinical Crossroads" Molecular Therapy, vol. 20, No. 4, pp. 699-708 (2012).

Bancel. S. et al., EBII Accession No. GSN:BAW43417.

Blomer et al. "Highly Efficient and Sustained Gene Transfer in Adult Neurons with a Lentivirus Vector" Journal of Virology, vol. 71, No. 9, pp. 6641-6649 (1997).

Bolivar (1979) "Molecular cloning vectors derived from the CoLEI type plasmid pMBI," Life sciences. 25(10): 807-817.

Cao et al. "ASGCT abstract #460; details of mutations disclosed in oral presentation—A Novel Factor VII Variant with Enhanced Secretion for Gene Therapy of Hemophilia A," Molecular Therapy (2014).

Chuah et al. (2012) "Platelet-directed gene therapy overcomes inhibitory antibodies to factor VIII," Journal of Thrombosis and Haemostasis. 10(8):1566-1569.

Chuah et al. (2012) "Recent progress in gene therapy for hemophilia," Human gene therapy. 23(6):557-565.

Chuah et al. (2013) "Gene therapy for hemophilia," Journal of thrombosis and haemostasis. 11:99-110.

Chuah et al. (2014) "Liver-specific transcriptional modules identified by genome-wide in silico analysis enable efficient gene therapy in mice and non-human primates," Molecular Therapy. 22(9):1605-1613.

Cotten et al. (1992) "High-efficiency receptor-mediated delivery of small and large (48 kilobase gene constructs using the endosome-disruption activity of defective or chemically inactivated adenovirus particles" Proc. Natl. Acad. Sci. USA, vol. 89, pp. 6094-6098.

Curiel "High-efficiency gene transfer employing adenovirus-polylysine-DNA complexes." Natural Immunity, vol. 13, pp. 141-164 (1994).

Devereux, J et al. "A comprehensive set of sequence analysis programs for the VAX." Nucleic acids research vol. 12,1 Pt 1 (1984): 387-95. doi:10.1093/nar/12.1part1.387.

Database GenBank (Apr. 23, 2019) "*Homo sapiens* serpin family a member 1 (SERPINA1), transcript variant 1, mRNA," NCBI Reference Sequence: NM_000295.4, 5 pages.

Database GenBank (Apr. 6, 2016) "coagulation factor VIII [*Homo sapiens*]," NCBI Reference Sequence: AAA52420.1, 3 pages.

Database GenBank (Aug. 13, 2003) "factor VIII [Rattus norvegicus]," NCBI Reference Sequence: AAQ21580.1, 2 pages.

Database GenBank (Aug. 4, 2008) "Coagulation factor VIII, procoagulant component [*Homo sapiens*]," NCBI Reference Sequence: AAH22513.1, 2 pages.

Database GenBank (Aug. 4, 2008) "Coagulation factor VIII, procoagulant component [*Homo sapiens*]," NCBI Reference Sequence: AAH64380.1, 2 pages.

Database GenBank (Aug. 4, 2008) "Coagulation factor VIII, procoagulant component [*Homo sapiens*]," NCBI Reference Sequence: AAH98389.1, 2 pages.

Database GenBank (Aug. 4, 2008) "Coagulation factor VIII, procoagulant component [*Homo sapiens*]," NCBI Reference Sequence: AAI11968.1, 2 pages.

Database GenBank (Aug. 4, 2008) "Coagulation factor VIII, procoagulant component [*Homo sapiens*]," NCBI Reference Sequence: AAI11970.1, 2 pages.

Database GenBank (Dec. 11, 2004) "coagulation factor VIII, procoagulant component (hemophilia A) [*Homo sapiens*]," NCBI Reference Sequence: AAV85964.1, 3 pages.

Database GenBank (Dec. 31, 1994) "coagulation factor VIII associated protein B [*Homo sapiens*]," NCBI Reference Sequence: AAA58466.1, 1 page.

Database GenBank (Jan. 15, 2009) "coagulation factor VIII [Mus musculus]," NCBI Reference Sequence: CAM26492.1, 3 pages.

Database GenBank (Jan. 15, 2009) "coagulation factor VIII, procoagulant component [*Homo sapiens*]," NCBI Reference Sequence: CAI41660.1, 3 pages.

Database GenBank (Jan. 15, 2009) "coagulation factor VIII, procoagulant component [*Homo sapiens*]," NCBI Reference Sequence: CAI41666.1, 3 pages.

Database GenBank (Jan. 15, 2009) "coagulation factor VIII, procoagulant component [*Homo sapiens*]," NCBI Reference Sequence: CAI41672.1, 3 pages.

(56) References Cited

OTHER PUBLICATIONS

Database GenBank (Jan. 15, 2009) "coagulation factor VIII, procoagulant component [*Homo sapiens*]," NCBI Reference Sequence: CAI43241.1, 3 pages.
Database GenBank (Jan. 29, 2011) "HS14F12r HS Hordeum vulgare subsp. vulgare cDNA clone HS14F12 5-PRIME, mRNA sequence," NCBI Reference Sequence: CA003404.1, 1 page.
Database GenBank (Jan. 9, 2008) "unnamed protein product [*Homo sapiens*]," NCBI Reference Sequence: BAF82636.1, 2 pages.
Database GenBank (Jul. 26, 2016) "coagulation factor VIII [Mus musculus]," NCBI Reference Sequence: EDL29229.1, 3 pages.
Database GenBank (Jun. 15, 1997) "clotting factor VIII, partial [*Homo sapiens*]," NCBI Reference Sequence: AAB61261.1, 1 page.
Database GenBank (Jun. 7, 1993) "coagulation factor VIII [Mus musculus domesticus]," NCBI Reference Sequence: AAA37385.1, 2 pages.
Database GenBank (Mar. 23, 2015) "coagulation factor VIII, procoagulant component (hemophilia A), isoform CRA_a [*Homo sapiens*]," NCBI Reference Sequence: EAW72645.1, 2 pages.
Database GenBank (May 24, 2008) "unnamed protein product [*Homo sapiens*]," NCBI Reference Sequence: BAG36452.1, 2 pages.
Database GenBank (May 3, 2008) "coagulation factor VIII [Mus musculus]," NCBI Reference Sequence: CAM15581.1, 2 pages.
Database GenBank (Nov. 8, 1994) "factor VIII [*Homo sapiens*]," NCBI Reference Sequence: AAA52484.1, 3 pages.
Database GenBank (Nov. 8, 1994) "Human coagulation factor VIII:C mRNA, complete cds," NCBI Reference Sequence: M14113.1, 4 pages.
Database GenBank (Nov. 8, 1994) "preprocoagulation factor VIII:C [*Homo sapiens*]," NCBI Reference Sequence: AAA52485.1, 4 pages.
Database GenBank (Oct. 7, 2008) "unnamed protein product [*Homo sapiens*]," NCBI Reference Sequence: CAA25619.1, 4 pages.
Database UniProt (Jan. 9, 2013) "Full=Coagulation factor VIII {ECO:0000313|Ensembl:ENSSSCP00000031036}" NCBI Reference Sequence: F1RZ36, 1 page.
Database UniProt (May 3, 2011) "ull=Coagulation factor VIII {ECO:0000313|Ensembl:ENSSSCP00000013628}" NCBI Reference Sequence: F1RZ36, 2 pages.
Database UniProt (Nov. 13, 2019) "RecName: Full=Coagulation factor VIII; AltName: Full=Antihemophilic factor; Short=AHF; AltName: Full=Procoagulant component; Contains: RecName: Full=Factor VIIIa heavy chain, 200 kDa isoform; Contains: RecName: Full=Factor VIIIa heavy chain, 92 kDa isoform; Co. . . ," NCBI Reference Sequence: P00451.1, 61 pages.
Database UniProt (Oct. 16, 2019) "RecName: Full=Coagulation factor IX; AltName: Full=Christmas factor; AltName: Full=Plasma thromboplastin component; Short=PTC; Contains: RecName: Full=Coagulation factor IXa light chain; Contains: RecName: Full=Coagulation factor IXa heavy chain; Flags: Precursor" NCBI Reference Sequence: P00740.2, 36 pages.
Daya and Berns "Gene Therapy Using Adeno-Associated Virus Vectors" Clinical Microbiology Reviews, vol. 21, No. 4, pp. 583-593 (2008).
Desmet et al. (2005) "Anchor profiles of HLA-specific peptides: analysis by a novel affinity scoring method and experimental validation," PROTEINS: Structure, Function, and Bioinformatics. 58(1):53-69.
Donath et al. "Characterization of des-(741-1668)-factor VIII, a single-chain factor VIII variant with a fusion site susceptible to proteolysis by thrombin and factor Xa" Biochem Journal, vol. 312, pp. 49-55 (1995).
Fagone et al. (2012) "Systemic errors in quantitative polymerase chain reaction titration of self-complementary adeno-associated viral vectors and improved alternative methods," Human Gene Therapy, Part B: Methods. 23(1): 1-7.
Fath et al. "Multiparameter RNA and Codon Optimization: A Standardized Tool to Assess and Enhance Autologous Mammalian Gene Expression" PLoS ONE, vol. 6, Issue 3, pp. 1-14 (2011).

Feng et al. (1987) "Progressive sequence alignment as a prerequisite to correct phylogenetic trees," Journal of molecular evolution. 25(4):351-360.
Gardinier-Garden et al. "CpG Islands in vertebrate genomes" Journal of Molecular Biology, vol. 196, Issue 2, pp. 261-282 (1987).
GenBank Accession No. EU159410.1, "Synthetic construct B domain-deleted coagulation factor VIII gene, complete cds", Jun. 23, 2009 [online], 3 pages [retrieved on Mar. 1, 2021] Retrieved from the National Center for Biotechnology Information Database using Internet <URL: https://www.ncbi.nlm.nih.gov/nucleotide/EU159410.1?report=genbank&log$=nucltop&blast_rank=1&RID=VX3HYF04016>.
Graw et al. (2005) "Haemophilia A: from mutation analysis to new therapies," Nature Reviews Genetics. 6(6):488-501.
Gray et al. "Optimizing Promoters for Recombinant Adeno-Associated Virus-Mediated Gene Expression in the Peripheral and Central Nervous System Using Self-Complementary Vectors" Human Gene Therapy, vol. 22, pp. 1143-1153 (2011).
Grieger et al. "Production of Recombinant Adeno-associated Virus Vectors Using Suspension HEK293 Cells and Continuous Harvest of Vector From the Culture Media for GMP FIX and FLT1 Clinical Vector" Molecular Therapy, vol. 24, No. 2, pp. 287-297 (2015).
Grote et al. "JCat: a novel tool to adapt codon usage of a target gene to its potential expression host" Nucleic Acid Research, vol. 33, pp. W526-W531 (2005).
Guidance for Industry—Estimating the Maximum Safe Starting Dose in Initial Clinical Trials for Therapeutics in Adult Healthy Volunteers, U.S. Department of Health and Human Services, Food and Drug Administration, Center for Drug Evaluation and Research (CDER), Jul. 2005, Pharmacology and Toxicology.
Gupta, R. et al., "NetNGlyc 1.0 Server," located at: http://www.cbs.dtu.dk/services/NetNGlyc/, 2004, last accessed, May 30, 2018.
Haas et al. "Codon usage limitation in the expression of HIV-1 envelope glycoprotein" Current Biology, vol. 6, No. 3, pp. 315-324 (1996).
Higgins et al. (1989) "Fast and sensitive multiple sequence alignments on a microcomputer," Bioinformatics. 5(2):151-153.
High (2012) "The gene therapy journey for hemophilia: are we there yet?" Blood, The Journal of the American Society of Hematology. 120(23):4482-4487.
Hsieh et al. (2009) "Transthyretin-driven oncolytic adenovirus suppresses tumor growth in orthotopic and ascites models of hepatocellular carcinoma," Cancer science. 100(3):537-545.
International Search Report for International Application No. PCT/US2016/061684, mailed Feb. 15, 2017, 16 pages.
International Search Report for International Application No. PCT/US2016/061688, mailed Feb. 6, 2017, 16 pages.
International Search Report for International Application No. PCT/US2019/041802, mailed Jan. 23, 2020, 17 pages.
Karlin et al. (1993) "Applications and statistics for multiple high-scoring segments in molecular sequences," Proceedings of the National Academy of Sciences. 90(12):5873-5877.
Kelleher and Vos, "Long-term episomal gene delivery in human lymphoid cells using human and avian adenoviral-assisted transfection" Biotechniques, vol. 17, pp. 1110-1117 (1994).
Kotin (2011) "Large-scale recombinant adeno-associated virus production," Human molecular genetics. 20(R1):R2-R6.
Kriegler "Gene Transfer and Expression, A Laboratory Manual" (1990).
Krinner et al. "CpG domains downstream of TSSs promote high levels of gene expression" Nucleic Acid Research, vol. 42, No. 6, pp. 3551-3564 (2014).
Kudla et al. "High Guanine and Cytosine Content Increases mRNA Levels in Mammalian Cells" PLoS Biology, vol. 4, Issue 6, pp. 0933-0942 (2006).
Laupeze et al. (1999) "Differential expression of major histocompatibility complex class Ia, Ib and II molecules on monocytes and monocyte-derived dendritic and macrophagic cells," Human immunology. 60(7):591-597.
Lenting et al. (1998) "The life cycle of coagulation factor VIII in view of its structure and function," Blood, The Journal of the American Society of Hematology. 92(11):3983-3996.

(56) References Cited

OTHER PUBLICATIONS

Mann et al. "Construction of a retrovirus packaging mutant and its use to produce helper-free defective retrovirus" Cell, vol. 33, Issue 1, pp. 153-159 (1983).
Manno et al. "Successful transduction of liver in hemophilia by AAV-Factor IX and limitations imposed by the host immune response." Nature Medicine, vol. 12 pp. 342-347 (2006).
Mannucci (2003) "Hemophilia: treatment options in the twenty-first century," Journal of Thrombosis and Haemostasis. 1(7):1349-1355.
Mátrai et al. (2010) "Preclinical and clinical progress in hemophilia gene therapy," Current opinion in hematology. 17(5):387-392.
Mátrai et al. (2010) "Recent advances in lentiviral vector development and applications," Molecular therapy. 18(3):477-490.
McIntosh et al. "Therapeutic levels of FVIII following a single peripheral vein administration of rAAV vector encoding a novel human factor VIII variant" Blood Journal, vol. 121, No. 17, pp. 3335-3344 (2013).
Miao et al. "Bioengineering of coagulation factor VIII for improved secretion" Blood Journal, vol. 103, No. 9, pp. 3412-3419 (2004).
Mirsafian et al. "A Comparative Analysis of Synonymous Codon Usage Bias Pattern in Human Albumin Superfamily" Scientific World Journal, vol. 2014, Article 639682, pp. 1-7 (2014).
Murray, E.J., "Gene Transfer and Expression Protocols" Methods in Molecular Biology, vol. 7, Humana Press, Inc. (1991).
Muzyczka "Use of adeno-associated virus as a general transduction vector for mammalian cells." Current Topics Microbiology and Immunology, vol. 158, pp. 97-129 (1992).
Naldini et al. "In Vivo Gene Delivery and Stable Transduction of Nondividing Cells by a Lentiviral Vector" Science, vol. 272, Issue 5259, pp. 263-267 (1996).
Needleman et al. (1970) "A general method applicable to the search for similarities in the amino acid sequence of two proteins," Journal of molecular biology. 48(3):443-453.
Nicolas and Rubenstein, "Retroviral vectors," In: Vectors. A survey of molecular cloning vectors and their uses, Rodriguez and Denhardt (eds.), Stoneham: Butterworth, pp. 494-513 (1988).
Oh et al. "Purification of Recombinant Human B-Domain-Deleted Factor VIII Using Anti-Factor VIII Monoclonal Antibody Selected by the Surface Plasmon Resonance Biosensor" Biotechnol. Prog., vol. 17, pp. 1119-1127 (2001).
Pearson et al. (1988) "Improved tools for biological sequence comparison," Proceedings of the National Academy of Sciences. 85(8):2444-2448.
Penaud-Budloo et al. (2018) "Pharmacology of recombinant adeno-associated virus production," Molecular Therapy-Methods & Clinical Development. 8:166-180.
Radcliff et al. "Analysis of factor VIII mediated suppression of lentiviral vector titres" Gene Therapy, vol. 15, pp. 289-297 (2008).
Reipert et al. (2010) "Animal models of inhibitors," Haemophilia. 16:47-53.
Roberts et al. (2011) "Engineering factor Viii for hemophilia gene therapy." Journal of genetic syndrome & gene therapy. S1:006(1-16).
Saenko et al. (1999) "Role of activation of the coagulation factor VIII in interaction with vWf, phospholipid, and functioning within the factor Xase complex," Trends in cardiovascular medicine. 9(7):185-192.
Sandberg et al. "Structural and functional characteristics of the B-domain-deleted recombinant factor VIII, r-VIII SQ", Journal of Thrombosis and Haemostasis, vol. 85, pp. 93-100 (2001).
Selvaraj et al. "Bioengineering of coagulation factor VIII for efficient expression through elimination of a dispensable disulfide loop" Journal of Thrombosis and Haemostasis, vol. 10, pp. 107-115 (2012).
Smith et al. (1981) "Comparison of biosequences," Advances in applied mathematics. 2(4):482-489.
Steentoft et al. (2013) "Precision mapping of the human O—GalNAc glycoproteome through SimpleCell technology," The EMBO journal. 32(10):1478-1488.
Sun et al. (2018) "A Retrospective Study of the Cytokine Profile Changes in Mice with FVIII Inhibitor Development After Adeno-Associated Virus-Mediated Gene Therapy in a Hemophilia a Mouse Model." Human gene therapy vol. 29,3 (2018):381-389. doi:10.1089/hum.2017.094.
Sutcliffe (1978) "Nucleotide sequence of the ampicillin resistance gene of *Escherichia coli* plasmid pBR322," Proceedings of the National Academy of Sciences. 75(8):3737-3741.
Swaaroop et al. "Mutagenesis of a Potential Immunoglobulin-binding Protein-binding Site Enhances Secretion of Coagulation Factor VIII" Journal of Biological Chemistry, vol. 272, No. 39, pp. 24121-24124 (1997).
Tats et al. "Preferred and avoided codon pairs in three domains of life" BMC Genomics, vol. 9, Issue 463, pp. 1-15 (2008).
Temin, H.M. "Retrovirus Vectors for Gene Transfer: Efficient Integration into and Expression of Exogenous DNA in Vertebrate Cell Genomes" In: Kucherlapati R. (eds) Gene Transfer (1986).
Thim et al., "Purification and characterization of a new recombinant factor VIII (N8)" Haemophilia, vol. 16, Issue 2, pp. 349-359 (2010).
Toschi et al. OBI-1, porcine recombinant Factor VIII for the potential treatment of patients with congenital hemophilia A and alloantibodies against human Factor VIII, Current Opinion in Molecular Therapy, vol. 12, No. 5, pp. 617-625 (2010).
Van Helden et al. (2011) "Maintenance and break of immune tolerance against human factor VIII in a new transgenic hemophilic mouse model," Blood, The Journal of the American Society of Hematology. 118(13):3698-3707.
Vandendriessche et al. (2012) "Clinical progress in gene therapy: sustained partial correction of the bleeding disorder in patients suffering from severe hemophilia B," Human gene therapy. 23(1):4-6.
Varfaj et al. "Residues Surrounding Arg336 and Arg562 Contribute to the Disparate Rates of Proteolysis of Factor VIIIa Catalyzed by Activated Protein C" Journal of Biological Chemistry, vol. 282, No. 28, pp. 20264-20272 (2007).
Verreck et al. (1996) "The generation of SDS-stable HLA DR dimers is independent of efficient peptide binding," International immunology. 8(3):397-404.
Wakabayashi et al. (2005) "A Glu113Ala mutation within a factor VIII Ca2+ binding site enhances cofactor interactions in factor Xase" Biochemistry, vol. 44, pp. 10298-10304.
Wakabayashi et al. (2002) "Ca(2+) binding to both the heavy and light chains of factor VIII is required for cofactor activity" Biochemistry, vol. 41, pp. 8485-8492.
Wakabayashi et al. (2009) "Combining mutations of charged residues at the A2 domain interface enhances factor VIII stability over single point mutations" Journal of Thrombosis and Haemostasis, vol. 7, pp. 438-444.
Wakabayashi et al. (2012) "Enhancing factor VIII and VIIIa stability by combining mutations at the A2 domain interface and A1—C2 domain interface" Journal of Thrombosis and Haemostasis., vol. 10, pp. 492-495.
Wakabayashi et al. (2008) "Generation of enhanced stability factor VIII variants by replacement of charged residues at the A2 domain interface" Blood, vol. 12, No. 7, pp. 2761-2769.
Wakabayashi et al. (2011) "Increasing Hydrophobicity or Disulfide Bridging at the Factor VIII A1 and C2 Domain Interface Enhances Procofactor Stability" Journal of Biological Chemistry, vol. 286, No. 29 pp. 25748-25755.
Wakabayashi et al. (2004) "Residues 110-126 in the A1 Domain of Factor VIII Contain a Ca2+ Binding Site Required for Cofactor Activity" Journal of Biochemistry, vol. 279, No. 13, pp. 12677-12684.
Ward et al. (2011) "Codon optimization of human factor VIII cDNAs leads to high-level expression" Blood Journal, vol. 117, No. 3, pp. 798-807 \.
Yan et al. (1990) "Distinct positive and negative elements control the limited hepatocyte and choroid plexus expression of transthyretin in transgenic mice," The EMBO journal. 9(3):869-878.
Zhang et al. (2009) "Factor VIII inhibitors: risk factors and methods for prevention and immune modulation," Clinical reviews in allergy & immunology. 37(2):114-124.

(56) References Cited

OTHER PUBLICATIONS

Zollner et al. "Non-clinical pharmacokinetics and pharmacodynamics of rVIII-SingleChain, a novel recombinant single-chain factor VIII", Thrombosis Research, vol. 134, pp. 125-131 (2014).
Zufferey et al. "Multiply attenuated lentiviral vector achieves efficient gene delivery in vivo" Nature Biotechnology, vol. 15, pp. 871-875 (1997).
U.S. Appl. No. 15/349,930, filed Nov. 11, 2016, now U.S. Pat. No. 10,189,888.
U.S. Appl. No. 16/211,201, filed Dec. 5, 2018.
U.S. Appl. No. 16/211,202, filed Dec. 5, 2018.
U.S. Appl. No. 17/570,187, filed Jan. 6, 2022.
U.S. Appl. No. 15/349,940, filed Nov. 11, 2016, now U.S. Pat. No. 10,189,889.
U.S. Appl. No. 16/743,850, filed Jan. 15, 2020.
U.S. Appl. No. 18/145,784, filed Dec. 12, 2022.
U.S. Appl. No. 17/784,093, filed Jun. 9, 2022.

CS04-FL-NA

```
atgcagattgagctgagcacctgcttcttcctgtgcctgctgaggttctgcttctctgccaccagga
gatactacctgggggctgtggagctttcttgggactacatgcagtctgacctgggggagctgcctgt
ggatgccaggttcccacccagagtgcccaaatccttcccattcaacacctctgtggtctacaagaag
accctctttgtggagttcactgaccacctgttcaacattgccaaacccaggccaccctggatgggac
tcctgggaccaccattcaggctgaggtgtatgacactgtggtcatcaccctcaagaacatggcctc
ccaccctgtgagcctgcatgctgtggggtcagctactggaaggcctctgaggggctgagtatgat
gaccagacctcccagagggagaaggaggatgacaaagtgttccctggggcagccacacctatgtgt
ggcaggtcctcaaggagaatggccccatggcctctgacccactctgcctgacctactcctaccttc
tcatgtggacctggtcaaggacctcaactctggactgattggggccctgctggtgtgcagggagggc
tccctggccaaagagaagacccagaccctgcacaagttcattctcctgtttgctgtctttgatgagg
gcaagagctggcactctgaaaccaagaactccctgatgcaggacagggatgctgcctctgccaggc
ctggcccaagatgcacactgtgaatggctatgtgaacaggagcctgcctggactcattggctgccac
aggaaatctgtctactggcatgtgattggcatggggacaaccctgaggtgcactccattttcctgg
agggccacaccttcctggtcaggaaccacagacaggccagcctggagatcagcccatcaccttcct
cactgcccagaccctgctgatggacctcggacagttcctgctgttctgccacatcagctccaccag
catgatggcatggaggcctatgtcaaggtggacagctgccctgaggagccacagctcaggatgaaga
acaatgaggaggctgaggactatgatgatgacctgactgactctgagatggatgtggtccgctttga
tgatgacaacagcccatccttcattcagatcaggtctgtggccaagaaacaccccaagacctgggtg
cactacattgctgctgaggaggaggactgggactatgccccactggtcctggcccctgatgacagga
gctacaagagccagtacctcaacaatggcccacagaggattggacgcaagtacaagaaagtcaggtt
catggcctacactgatgaaaccttcaagaccagggaggccattcagcatgagtctggcatcctgggc
ccactcctgtatggggaggtggggacaccctgctcatcatcttcaagaaccaggcctccaggccct
acaacatctacccacatggcatcactgatgtcaggcccctgtacagccgcaggctgccaaaggggt
gaaacacctcaaggacttccccattctgcctggggagatcttcaagtacaagtggactgtcactgtg
gaggatggaccaaccaaatctgacccaggtgcctcaccagatactactccagctttgtgaacatgg
agagggacctggcctctggcctgattggcccactgctcatctgctacaaggagtctgtggaccagag
gggaaaccagatcatgtctgacaagaggaatgtgattctgttctctgtctttgatgagaacaggagc
tggtacctgactgagaacattcagcgcttcctgcccaaccctgctggggtgcagctggaggaccctg
agttccaggccagcaacatcatgcactccatcaatggctatgtgtttgacagcctccagctttctgt
ctgcctgcatgaggtggcctactggtacattctttctattggggcccagactgacttccttttctgtc
ttcttctctggctacaccttcaaacacaagatggtgtatgaggacacccctgaccctcttcccattct
ctggggagactgtgttcatgagcatggagaaccctggcctgtggattctgggatgccacaactctga
cttccgcaacaggggcatgactgccctgctcaaagtctcctcctgtgacaagaacactggggactac
tatgaggacagctatgaggacatctctgcctacctgctcagcaagaacaatgccattgagcccagga
gcttcagccagaatccacctgtcctgaaacgccaccagagggagatcaccaggaccaccctccagtc
tgaccaggaggagattgactatgatgacccatttctgtggagatgaagaagaggactttgacatc
tatgacgaggacgagaaccagagcccaaggagcttccagaagaagaccaggcactacttcattgctg
ctgtggagcgcctgtgggactatggcatgagctccagcccccatgtcctcaggaacagggcccagtc
tggctctgtgccacagttcaagaaagtggtcttccaagagttcactgatggcagcttcacccagccc
ctgtacagggggagctgaatgagcacctggactcctgggcccatacatcagggctgaggtggagg
acaacatcatggtgaccttccgcaaccaggcctccaggccctacagcttctacagctccctcatcag
ctatgagGaggaccagaggcaggggctgagccacgcaagaactttgtgaacccaatgaaaccaag
acctacttctggaaagtccagcaccacatggcccccaccaaggatgagtttgactgcaaggcctggg
```

```
cctacttctctgatgtggacctggagaaggatgtgcactctggcctgattggcccactcctggtctg
ccacaccaacaccctgaaccctgcccatggaaggcaagtgactgtgcaggagtttgccctcttcttc
accatctttgatgaaaccaagagctggtacttcactgagaacatggagcgcaactgcagggccccat
gcaacattcagatggaggacccaccttcaaagagaactaccgcttccatgccatcaatggctacat
catggacaccctgcctgggcttgtcatggcccaggaccagaggatcaggtggtacctgctttctatg
ggctccaatgagaacattcactccatccacttctctgggcatgtcttcactgtgcgcaagaaggagg
agtacaagatggccctgtacaacctctaccctggggtctttgagactgtggagatgctgccctccaa
agctggcatctggagggtggagtgcctcattggggagcacctgcatgctggcatgagcaccctgttc
ctggtctacagcaacaagtgccagacccccctgggaatggcctctggccacatcagggacttccaga
tcactgcctctggccagtatggccagtgggccccaagctggccaggctccactactctggatccat
caatgcctggagcaccaaggagccattcagctggatcaaagtggacctgctggccccatgatcatc
catggcatcaagacccagggggccaggcagaagttctccagcctgtacatcagccagttcatcatca
tgtacagcctggatggcaagaaatggcagacctacagaggcaactccactggaacactcatggtctt
ctttggcaatgtggacagctctggcatcaagcacaacatcttcaaccccccaatcatcgccagatac
atcaggctgcaccccacccactacagcatccgcagcaccctcaggatggagctgatgggctgtgacc
tgaactcctgcagcatgcccctgggcatggagagcaaggccatttctgatgcccagatcactgcctc
cagctacttcaccaacatgtttgccacctggagcccaagcaaggccaggctgcacctccagggaagg
agcaatgcctggaggcccaggtcaacaacccaaaggagtggctgcaggtggacttccagaagacca
tgaaggtcactggggtgaccacccagggggtcaagagcctgctcaccagcatgtatgtgaaggagtt
cctgatcagctccagccaggatggccaccagtggaccctcttcttccagaatggcaaggtcaaggtg
ttccagggcaaccaggacagcttcacCcctgtggtgaacagcctggaccccccctcctgaccagat
acctgaggattcaccccagagctgggtccaccagattgccctgaggatggaggtcctgggatgtga
ggcccaggacctgtactga (SEQ ID NO:1)
```

MQIELSTCFFLCLLRFCFSATRRYYLGAVELSWDYMQSDLGELPVDAR' FPPRVPKSFPFNTSVVYK
KTLFVEFTDHLFNIAKPRPPWMGLLGPTIQAEVYDTVVITLKNMASHPVSLHAVGVSYWKASEGAEY
DDQTSQREKEDDKVFPGGSHTYVWQVLKENGPMASDPLCLTYSYLSHVDLVKDLNSGLIGALLVCRE
GSLAKEKTQTLHKFILLFAVFDEGKSWHSETKNSLMQDRDAASARAWPKMHTVNGYVNRSLPGLIGC
HRKSVYWHVIGMGTTPEVHSIFLEGHTFLVRNHRQASLEISPITFLTAQTLLMDLGQFLLFCHISSH
QHDGMEAYVKVDSCPEEPQLRMKNNEEAEDYDDDLTDSEMDVVRFDDDNSPSFIQIRSVAKKHPKTW
VHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVT
VEDGPTKSDPRCLTRYYSSFVNMERDLASGLIGPLLICYKESVDQRGNQIMSDKRNVILFSVFDENR
SWYLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNTGD
YYEDSYEDISAYLLSKNNAIEPRSFSQNPPVLKRHQREITRTTLQSDQEEIDYDDTISVEMKKEDFD
IYDEDENQSPRSFQKKTRHYFIAAVERLWDYGMSSSPHVLRNRAQSGSVPQFKKVVFQEFTDGSFTQ
PLYRGELNEHLGLLGPYIRAEVEDNIMVTFRNQASRPYSFYSSLISYEEDQRQGAEPRKNFVKPNET
KTYFWKVQHHMAPTKDEFDCKAWAYFSDVDLEKDVHSGLIGPLLVCHTNTLNPAHGRQVTVQEFALF
FTIFDETKSWYFTENMERNCRAPCNIQMEDPTFKENYRFHAINGYIMDTLPGLVMAQDQRIRWYLLS
MGSNENIHSIHFSGHVFTVRKKEEYKMALYNLYPGVFETVEMLPSKAGIWRVECLIGEHLHAGMSTL
FLVYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPIIAR
YIRLHPTHYSIRSTLRMELMGCDLNSCSMPLGMESKAISDAQITASSYFTNMFATWSPSKARLHLQG
RSNAWRPQVNNPKEWLQVDFQKTMKVTGVTTQGVKSLLTSMYVKEFLISSSQDGHQWTLFFQNGKVK
VFQGNQDSFTPVVNSLDPPLLTRYLRIHPQSWVHQIALRMEVLGCEAQDLY    (SEQ ID NO:2)

```
                                                                    gcc
accaggagat actacctggg ggctgtggag cttctcttggg actacatgca gtctgacctg
ggggagctgc ctgtggatgc caggttccca cccagagtgc ccaaatcctt cccattcaac
acctctgtgg tctacaagaa gaccctcttt gtggagttca ctgaccacct gttcaacatt
gccaaaccca ggccaccctg gatgggactc ctggaccca ccattcaggc tgaggtgtat
gacactgtgg tcatcaccct caagaacatg gcctccacc ctgtgagcct gcatgctgtg
ggggtcagct actggaaggc ctctgagggg gctgagtatg atgaccagac ctcccagagg
gagaaggagg atgacaaagt gttccctggg ggcagccaca cctatgtgtg gcaggtcctc
aaggagaatg gccccatggc ctctgaccca ctctgcctga cctactccta cctttctcat
gtggacctgg tcaaggacct caactctgga ctgattgggg ccctgctggt gtgcaggag
ggctccctgg ccaaagagaa gacccagacc ctgcacaagt tcattctcct gtttgctgtc
tttgatgagg gcaagagctg gcactctgaa accaagaact ccctgatgca ggacagggat
gctgcctctg ccagggcctg gccaagatg cacactgtga atggctatgt gaacaggagc
ctgcctggac tcattggctg ccacaggaaa tctgtctact ggcatgtgat tggcatgggg
acaacccctg aggtgcactc catttttcctg gagggccaca ccttcctggt caggaaccac
agacaggcca gctggagat cagccccatc accttcctca ctgcccagac cctgctgatg
gacctcggac agttcctgct gttctgccac atcagctccc accagcatga tggcatggag
gcctatgtca aggtggacag ctgcctgag gagccacagc tcaggatgaa gaacaatgag
gaggctgagg actatgatga tgacctgact gactctgaga tggatgtggt ccgctttgat
gatgacaaca gccatccttt cattcagatc aggtctgtgg ccaagaaaca ccccaagacc
tgggtgcact acattgctgc tgaggaggag gactggact atgccccact ggtcctggcc
cctgatgaca ggagctacaa gagccagtac ctcaacaatg gcccacagag gattggacgc
aagtacaaga agtcaggtt catggcctac actgatgaaa ccttcaagac cagggaggcc
attcagcatg agtctggcat cctgggccca ctcctgtatg gggagtggg ggacaccctg
ctcatcatct tcaagaacca ggcctccagg cctacaaca tctacccaca tggcatcact
gatgtcaggc cctgtacag ccgcaggctg ccaaagggg tgaaacacct caaggacttc
cccattctgc ctggggagat cttcaagtac aagtggactg tcactgtgga ggatggacca
accaaatctg accccaggtg cctcaccaga tactactcca gctttgtgaa catggagagg
gacctggcct ctggcctgat tggcccactg ctcatctgct acaggagtc tgtgaccag
aggggaaacc agatcatgtc tgacaagagg aatgtgattc tgttctctgt ctttgatgag
aacaggagct ggtacctgac tgagaacatt cagcgcttcc tgcccaaccc tgctggggtg
cagctggagg accctgagtt ccaggccagc aacatcatgc actccatcaa tggctatgtg
tttgacagcc tccagctttc tgtctgcctg catgaggtgg cctactggta cattctttct
attggggccc agactgactt cctttctgtc ttcttctctg gctacacctt caaacacaag
atggtgtatg aggacacct gaccctcttc ccattctctg gggagactgt gttcatgagc
atggagaacc ctggcctgtg gattctggga tgccacaact ctgacttccg caacagggc
atgactgccc tgctcaaagt ctcctcctgt gacaagaaca ctgggggacta ctatgaggac
agctatgagg acatctctgc ctacctgctc agcaagaaca atgccattga gcccagg
(SEQ ID NO:3)
```

```
                                                      g agatcaccag gaccaccctc
cagtctgacc aggaggagat tgactatgat gacaccattt ctgtggagat gaagaaagag
gactttgaca tctatgacga ggacgagaac cagagcccaa ggagcttcca gaagaagacc
aggcactact tcattgctgc tgtggagcgc ctgtgggact atggcatgag ctccagcccc
catgtcctca ggaacagggc ccagtctggc tctgtgccac agttcaagaa agtggtcttc
caagagttca ctgatggcag cttcacccag ccctgtaca gagggggct gaatgagcac
ctgggactcc tgggcccata catcaggct gaggtggagg acaacatcat ggtgaccttc
cgcaaccagg cctccaggcc ctacagcttc tacagctccc tcatcagcta tgaggaggac
cagaggcagg gggctgagcc acgcaagaac tttgtgaaac ccaatgaaac caagacctac
ttctggaaag tccagcacca catggccccc accaaggatg agtttgactg caaggcctgg
gcctacttct ctgatgtgga cctggagaag gatgtgcact ctggcctgat tgcccactc
ctggtctgcc acaccaacac cctgaaccct gccatggaa ggcaagtgac tgtgcaggag
tttgccctct tcttcaccat ctttgatgaa accaagagct ggtacttcac tgagaacatg
gagcgcaact gcagggcccc atgcaacatt cagatggagg acccaccttt caaagagaac
taccgcttcc atgccatcaa tggctacatc atggacaccc tgcctgggct tgtcatggcc
caggaccaga ggatcaggtg gtacctgctt tctatgggct ccaatgagaa cattcactcc
atccacttct ctgggcatgt cttcactgtg cgcaagaagg aggagtacaa gatggccctg
tacaacctct accctggggt ctttgagact gtggagatgc tgccctccaa agctggcatc
tggagggtgg agtgcctcat tggggagcac ctgcatgctg catgagcac cctgttcctg
gtctacagca acaagtgcca gacccccctg gaatggcct ctggccacat cagggacttc
cagatcactg cctctggcca gtatggccag tgggccccca agctggccag gctccactac
tctggatcca tcaatgcctg gagcaccaag gagccattca gctggatcaa agtggacctg
ctggccccca tgatcatcca tggcatcaag acccaggggg ccaggcagaa gttctccagc
ctgtacatca gccagttcat catcatgtac agcctggatg caagaaatg gcagacctac
agaggcaact ccactggaac actcatggtc ttctttggca atgtggacag ctctggcatc
aagcacaaca tcttcaaccc cccaatcatc gccagataca tcaggctgca ccccacccac
tacagcatcc gcagcaccct caggatggag ctgatgggct gtgacctgaa ctcctgcagc
atgcccctgg gcatggagag caaggccatt tctgatgccc agatcactgc ctccagctac
ttcaccaaca tgtttgccac ctggagccca agcaaggcca ggctgcacct ccagggaagg
agcaatgcct ggaggcccca ggtcaacaac ccaaaggagt ggctgcaggt ggacttccag
aagaccatga aggtcactgg ggtgaccacc caggggtca agagcctgct caccagcatg
tatgtgaagg agttcctgat cagctccagc caggatggcc accagtggac cctcttcttc
cagaatggca aggtcaaggt gttccagggc aaccaggaca gcttcacccc tgtggtgaac
agcctggacc ccccctcct gaccagatac ctgaggattc accccagag ctgggtccac
cagattgccc tgaggatgga ggtcctggga tgtgaggccc aggacctgta c
(SEQ ID NO:4)
```

Figure 5

4 - agc ttcagccaga atccacctgt cctgaaacgc caccagagg (SEQ ID NO:5)

```
1     tcgcgcgttt cggtgatgac ggtgaaaacc tctgacacat gcagctcccg gagacggtca
61    cagcttgtct gtaagcggat gccggagca  gacaagcccg tcagggcgcg tcagcgggtg
121   ttggcgggtg tcgggctgg  cttaactatg cggcatcaga gcagattgta ctgagagtgc
181   accatatgcg gtgtgaaata ccgcacagat gcgtaaggag aaaataccgc atcaggcgcc
241   attcgccatt caggctgcgc aactgttggg aagggcgatc ggtgcgggcc tcttcgctat
301   tacgccagct ggcgaaaggg ggatgtgctg caaggcgatt aagttgggta acgccagggt
361   tttccagtc  acgacgttgt aaaacgacgg ccagtgaatt cctcgagatt taaatgacgt
421   tggccactcc ctctctgcgc gctcgctcgc tcactgaggc cgggcgacca aaggtcgccc
481   gacgcccggg cttttgcccgg gcggcctcag tgagcgagcg agcgcgcaga gagggagtgg
541   ccaactccat cactaggggt tcctgagttt aaacttcgtc gacgattcga gcttgggctg
601   caggtcgagg gcactgggag gatgttgagt aagatggaaa actactgatg cccttgcag
661   agacagagta ttaggacatg tttgaacagg ggccgggcga tcagcaggta gctctagagg
721   atccccgtct gtctgcacat ttcgtagagc gagtgttccg atactctaat ctccctaggc
781   aaggttcata tttgtgtagg ttacttattc tccttttgtt gactaagtca ataatcagaa
841   tcagcaggtt tggagtcagc ttggcaggga tcagcagcct gggttggaag gagggggtat
901   aaaagcccct tcaccaggag aagccgtcac acagactagg cgcgccaccg ccaccatgca
961   gattgagctg agcacctgct tcttcctgtg cctgctgagg ttctgcttct ctgccaccag
1021  gagatactac ctggggctg  tggagctttc ttgggactac atgcagtctg acctggggga
1081  gctgcctgtg gatgccaggt cccacccag  agtgcccaaa tccttcccat tcaacacctc
1141  tgtggtctac aagaagaccc tctttgtgga gttcactgac cacctgttca cattgccaa
1201  acccaggcca ccctggatgg gactcctggg acccaccatt caggctgagg tgtatgacac
1261  tgtggtcatc accctcaaga acatggcctc ccaccctgtg agcctgcatg ctgtgggggt
1321  cagctactgg aaggcctctg aggggctga  gtatgatgac cagacctccc agagggagaa
1381  ggaggatgac aaagtgttcc ctggggcag  ccacacctat gtgtggcagg tcctcaagga
1441  gaatggcccc atggcctctg accactctg  cctgacctac tctacctttt ctcatgtgga
1501  cctggtcaag gacctcaact ctggactgat tggggccctg ctggtgtgca gggagggctc
1561  cctggccaaa gagaagaccc agaccctgca caagttcatt ctcctgtttg ctgtctttga
1621  tgagggcaag agctggcact ctgaaaccaa gaactccctg atgcaggaca gggatgctgc
1681  ctctgccagg gcctggccca agatgcacac tgtgaatggc tatgtgaaca ggagcctgcc
1741  tggactcatt ggctgccaca ggaaatctgt ctactggcat gtgattggca tggggacaac
1801  ccctgaggtg cactccattt tcctggaggg ccacaccttc ctggtcagga accacagaca
1861  ggccagcctg gagatcagcc ccatcacctt cctcactgcc cagacctgc  tgatggacct
1921  cggacagttc ctgctgttct gccacatcag ctccaccagc atgatggca  tggaggccta
1981  tgtcaaggtg gacagctgcc ctgaggagcc acagctcagg atgaagaaca atgaggaggc
2041  tgaggactat gatgatgacc tgactgactc tgagatggat gtggtccgct tgatgatga
2101  caacagccca tccttcattc agatcaggtc tgtggccaag aaacacccca gacctgggt
2161  gcactacatt gctgctgagg aggaggactg ggactatgcc ccactggtcc tggccctga
2221  tgacaggagc tacaagagcc agtacctcaa caatggccca cagaggattg gacgcaagta
2281  caagaaagtc aggttcatgg cctacactga tgaaaccttc aagaccaggg aggccattca
2341  gcatgagtct ggcatcctgg gccactcct  gtatgggag gtgggggaca ccctgctcat
2401  catcttcaag aaccaggcct ccaggcccta caacatctac ccacatggca tcactgatgt
2461  caggccctg  tacagccgca ggctgccaaa gggggtgaaa cacctcaagg acttccccat
```

Figure 7A

```
2521 tctgcctggg gagatcttca agtacaagtg gactgtcact gtggaggatg gaccaaccaa
2581 atctgacccc aggtgcctca ccagatacta ctccagcttt gtgaacatgg agagggacct
2641 ggcctctggc ctgattggcc cactgctcat ctgctacaag gagtctgtgg accagagggg
2701 aaaccagatc atgtctgaca agaggaatgt gattctgttc tctgtctttg atgagaacag
2761 gagctggtac ctgactgaga acattcagcg cttcctgccc aaccctgctg ggtgcagct
2821 ggaggaccct gagttccagg ccagcaacat catgcactcc atcaatggct atgtgtttga
2881 cagcctccag ctttctgtct gcctgcatga ggtggcctac tggtacattc tttctattgg
2941 ggcccagact gacttccttt ctgtcttctt ctctggctac accttcaaac acaagatggt
3001 gtatgaggac accctgaccc tcttcccatt ctctggggag actgtgttca tgagcatgga
3061 gaaccctggc ctgtggattc tgggatgcca caactctgac ttccgcaaca gggcatgac
3121 tgccctgctc aaagtctcct cctgtgacaa gaacactggg gactactatg aggacagcta
3181 tgaggacatc tctgcctacc tgctcagcaa gaacaatgcc attgagccca ggagcttcag
3241 ccagaatcca cctgtcctga acgccacca gagggagatc accaggacca cctccagtc
3301 tgaccaggag gagattgact atgatgacac catttctgtg gagatgaaga agaggactt
3361 tgacatctat gacgaggacg agaaccagag cccaaggagc ttccagaaga agaccaggca
3421 ctacttcatt gctgctgtgg agcgcctgtg ggactatggc atgagctcca gccccatgt
3481 cctcaggaac agggcccagt ctggctctgt gccacagttc aagaaagtgg tcttccaaga
3541 gttcactgat ggcagcttca cccagcccct gtacagaggg gagctgaatg agcacctggg
3601 actcctgggc ccatacatca gggctgaggt ggaggacaac atcatggtga ccttccgcaa
3661 ccaggcctcc aggccctaca gcttctacag ctccctcatc agctatgagg aggaccagag
3721 gcaggggct gagccacgca gaactttgt gaaacccaat gaaaccaaga ctacttctg
3781 gaaagtccag caccacatgg ccccaccaa ggatgagttt gactgcaagg cctgggccta
3841 cttctctgat gtggacctgg agaaggatgt gcactctggc ctgattggcc cactcctggt
3901 ctgccacacc aacaccctga accctgccca tggaaggcaa gtgactgtgc aggagtttgc
3961 cctcttcttc accatctttg atgaaaccaa gagctggtac ttcactgaga acatggagcg
4021 caactgcagg gccccatgca acattcagat ggaggacccc accttcaaag agaactaccg
4081 cttccatgcc atcaatggct acatcatgga caccctgcct gggcttgtca tgcccagga
4141 ccagaggatc aggtggtacc tgctttctat gggctccaat gagaacattc actccatcca
4201 cttctctggg catgtcttca ctgtgcgcaa gaaggaggag tacaagatgg ccctgtacaa
4261 cctctaccct ggggtctttg agactgtgga tgctgccc tccaaagctg catctggag
4321 ggtggagtgc ctcattgggg agcacctgca tgctggcatg agcaccctgt cctggtcta
4381 cagcaacaag tgccagaccc cctgggaat ggcctctggc cacatcaggg acttccagat
4441 cactgcctct ggccagtatg ccagtgggc cccaagctg gccaggctcc actactctgg
4501 atccatcaat gcctggagca ccaaggagcc attcagctgg atcaaagtgg acctgctggc
4561 ccccatgatc atccatggca tcaagaccca ggggccaggg cagaagttct ccagcctgta
4621 catcagccag ttcatcatca tgtacagcct ggatgcaag aaatggcaga cctacagagg
4681 caactccact ggaacactca tggtcttctt tggcaatgtg gacagctctg gcatcaagca
4741 caacatcttc aaccccccaa tcatcgccag atacatcagg ctgcacccca ccactacag
4801 catccgcagc ccctcagga tggagctgat gggctgtgac ctgaactcct gcagcatgcc
4861 cctgggcatg gagagcaagg ccatttctga tgcccagatc actgcctcca gctacttcac
4921 caacatgttt gccacctgga gcccaagcaa ggccaggctg caccctccagg gaaggagcaa
4981 tgcctggagg cccaggtca acaacccaaa ggagtggctg caggtggact tccagaagac
```

Figure 7B

```
5041 catgaaggtc actggggtga ccacccaggg ggtcaagagc ctgctcacca gcatgtatgt
5101 gaaggagttc ctgatcagct ccagccagga tggccaccag tggaccctct tcttccagaa
5161 tggcaaggtc aaggtgttcc agggcaacca ggacagcttc acccctgtgg tgaacagcct
5221 ggaccccccc ctcctgacca gatacctgag gattcacccc cagagctggg tccaccagat
5281 tgccctgagg atggaggtcc tgggatgtga ggcccaggac ctgtactgat gacgagcggc
5341 cgctcttagt agcagtatcg ataataaaag atctttattt tcattagatc tgtgtgttgg
5401 ttttttgtgt gttaattaag ctcgcgaagg aaccctagt gatggagttg gccactccct
5461 ctctgcgcgc tcgctcgctc actgaggccg ggcgaccaaa ggtcgcccga cgcccgggct
5521 ttgcccgggc ggcctcagtg agcgagcgag cgcgcagaga gggagtggcc aagacgattt
5581 aaatgacaag cttggcgtaa tcatggtcat agctgtttcc tgtgtgaaat tgttatccgc
5641 tcacaattcc acacaacata cgagccggaa gcataaagtg taaagcctgg ggtgcctaat
5701 gagtgagcta actcacatta attgcgttgc gctcactgcc cgctttccag tcgggaaacc
5761 tgtcgtgcca gctgcattaa tgaatcggcc aacgcgcggg gagaggcggt ttgcgtattg
5821 ggcgctcttc cgcttcctcg ctcactgact cgctgcgctc ggtcgttcgg ctgcggcgag
5881 cggtatcagc tcactcaaag gcggtaatac ggttatccac agaatcaggg gataacgcag
5941 gaaagaacat gtgagcaaaa ggccagcaaa aggccaggaa ccgtaaaaag gccgcgttgc
6001 tggcgttttt ccataggctc cgcccccctg acgagcatca caaaaatcga cgctcaagtc
6061 agaggtggcg aaacccgaca ggactataaa gataccaggc gtttccccct ggaagctccc
6121 tcgtgcgctc tcctgttccg accctgccgc ttaccggata cctgtccgcc tttctccctt
6181 cgggaagcgt ggcgctttct catagctcac gctgtaggta tctcagttcg gtgtaggtcg
6241 ttcgctccaa gctgggctgt gtgcacgaac cccccgttca gcccgaccgc tgcgccttat
6301 ccggtaacta tcgtcttgag tccaacccgg taagacacga cttatcgcca ctggcagcag
6361 ccactggtaa caggattagc agagcgaggt atgtaggcgg tgctacagag ttcttgaagt
6421 ggtggcctaa ctacggctac actagaagaa cagtatttgg tatctgcgct ctgctgaagc
6481 cagttacctt cggaaaaaga gttggtagct cttgatccgg caaacaaacc accgctggta
6541 gcggtggttt ttttgtttgc aagcagcaga ttacgcgcag aaaaaaagga tctcaagaag
6601 atcctttgat cttttctacg ggtctgacg ctcagtggaa cgaaaactca cgttaaggga
6661 ttttggtcat gagattatca aaaggatct cacctagat ccttttaaat taaaaatgaa
6721 gttttaaatc aatctaaagt atatatgagt aaacttggtc tgacagttac caatgcttaa
6781 tcagtgaggc acctatctca gcgatctgtc tatttcgttc atccatagtt gcctgactcc
6841 ccgtcgtgta gataactacg atacgggagg gcttaccatc tggccccagt gctgcaatga
6901 taccgcgaga cccacgctca ccggctccag atttatcagc aataaaccag ccagccggaa
6961 gggccgagcg cagaagtggt cctgcaactt tatccgcctc catccagtct attaattgtt
7021 gccgggaagc tagagtaagt agttcgccag ttaatagttt gcgcaacgtt gttgccattg
7081 ctacaggcat cgtggtgtca cgctcgtcgt ttggtatggc ttcattcagc tccggttccc
7141 aacgatcaag gcgagttaca tgatccccca tgttgtgcaa aaaagcggtt agctccttcg
7201 gtcctccgat cgttgtcaga agtaagttgg ccgcagtgtt atcactcatg gttatggcag
7261 cactgcataa ttctcttact gtcatgccat ccgtaagatg cttttctgtg actggtgagt
7321 actcaaccaa gtcattctga gaatagtgta tgcggcgacc gagttgctct tgcccggcgt
7381 caatacggga taataccgcg ccacatagca gaactttaaa agtgctcatc attggaaaac
7441 gttcttcggg gcgaaaactc tcaaggatct taccgctgtt gagatccagt tcgatgtaac
7501 ccactcgtgc acccaactga tcttcagcat cttttacttt caccagcgtt tctgggtgag
7561 caaaaacagg aaggcaaaat gccgcaaaaa agggaataag ggcgacacgg aaatgttgaa
7621 tactcatact cttcctttttt caatattatt gaagcattta tcaggttat tgtctcatga
7681 gcggatacat atttgaatgt atttagaaaa ataaacaaat aggggttccg cgcacatttc
7741 cccgaaaagt gccacctgac gtctaagaaa ccattattat catgacatta acctataaaa
7801 ataggcgtat cacgaggccc tttcgtc    (SEQ ID NO:6)
```

```
ATGCAGATCGAACTGAGCACTTGCTTCTTCCTGTGTCTCCTGCGCTTTTGCTTCTCCGCCACAAGG
AGATACTATCTCGGTGCCGTGGAGCTCAGCTGGGACTACATGCAGAGCGACTTGGGTGAACTGCCT
GTGGACGCCAGGTTTCCACCCCGCGTGCCCAAGAGTTTCCCGTTCAACACCAGTGTCGTGTACAAG
AAAACCCTCTTCGTGGAATTCACCGACCACCTGTTCAACATCGCCAAACCGCGCCCTCCCTGGATG
GGGCTGCTCGGCCCGACGATCCAGGCTGAGGTCTATGACACGGTGGTGATTACCCTCAAGAACATG
GCTAGCCACCCGGTGAGCCTGCACGCCGTGGGCGTGTCCTATTGGAAAGCGTCCGAGGGTGCGGAG
TACGATGACCAGACTTCACAGCGGGAGAAGGAAGACGACAAAGTGTTCCCCGGGGGTTCCCACACC
TATGTCTGGCAGGTCCTGAAGGAGAATGGTCCTATGGCCTCCGACCCATTGTGCCTCACCTACTCT
TACCTAAGCCATGTGGATCTCGTCAAGGACCTGAACTCGGGGCTGATCGGCGCCCTGCTCGTGTGC
CGGGAGGGCTCACTGGCCAAGGAGAAGACCCAAACTCTGCACAAGTTCATCCTGCTGTTCGCGGTA
TTCGACGAGGGGAAGTCCTGGCACTCCGAGACCAAGAACAGCCTGATGCAGGACCGCGACGCAGCC
TCGGCCCGTGCGTGGCCAAAGATGCACACCGTGAACGGCTACGTTAACAGGAGCCTACCCGGCCTG
ATCGGCTGCCACCGCAAATCGGTCTACTGGCATGTGATCGGAATGGGCACAACGCCCGAGGTCCAC
AGTATCTTCCTCGAGGGCCACACTTTCCTGGTCCGGAATCACCGCCAGGCCAGCCTGGAGATCAGC
CCCATAACCTTTCTGACGGCGCAGACCTTACTCATGGATCTCGGCCAGTTCCTCCTGTTCTGCCAC
ATTTCGTCCCACCAGCACGATGGGATGGAAGCATATGTGAAAGTGGACTCCTGCCCCGAGGAACCC
CAGCTTAGGATGAAGAACAATGAGGAGGCCGAGGACTACGACGATGACCTTACCGATTCAGAAATG
GACGTAGTACGCTTTGACGACGACAACTCTCCATCCTTCATACAGATTCGCTCCGTCGCCAAGAAG
CACCCTAAGACTTGGGTGCACTACATCGCGGCCGAGGAGGAGGACTGGGATTATGCTCCCCTGGTG
CTGGCCCCCGACGACCGCAGCTACAAGAGCCAGTACCTGAATAACGGGCCCCAGCGCATCGGCCGG
AAGTACAAGAAAGTGCGGTTCATGGCTTACACGGACGAGACCTTCAAGACCCGGGAGGCTATCCAG
CATGAGAGCGGCATCTTGGGGCCCCTCCTGTACGGCGAAGTTGGAGACACACTGCTGATCATCTTC
AAGAACCAGGCGAGCAGGCCCTACAACATCTACCCCCACGGCATTACCGATGTCCGGCCGTTGTAC
AGCCGACGGCTGCCCAAGGGCGTGAAGCACCTGAAGGACTTTCCGATCCTGCCGGGCGAGATCTTC
AAGTACAAGTGGACTGTGACCGTGGAGGATGGGCCGACCAAGAGCGATCCGCGCTGCCTGACCCGT
TACTACTCCAGCTTTGTCAATATGGAGCGCGACCTCGCTAGCGGCTTGATTGGCCCTCTGCTGATC
TGCTACAAGGAGTCCGTGGACCAGAGGGGGAATCAGATCATGAGTGACAAGAGGAACGTGATCCTG
TTCTCCGTGTTCGACGAAAACCGCAGCTGGTATCTCACCGAGAATATCCAGCGCTTCCTGCCCAAC
CCGGCCGGTGTGCAGCTGGAGGACCCCGAGTTTCAGGCCAGCAACATCATGCATTCTATCAACGGA
TATGTGTTTGATTCCCTGCAGCTCTCAGTGTGTCTGCACGAGGTCGCCTACTGGTATATCCTCAGC
ATTGGGGCACAGACCGACTTCCTGAGCGTGTTCTTCTCCGGGTATACCTTCAAGCACAAGATGGTG
TACGAGGATACCCTGACCCTGTTCCCCTTTAGCGGCGAAACCGTGTTTATGTCTATGGAGAACCCC
GGGCTCTGGATCCTTGGCTGCCATAACTCCGACTTCCGCAACCGCGGAATGACCGCGCTCCTGAAA
GTGTCGAGTTGTGACAAGAACACCGGCGACTATTACGAGGACAGTTACGAGGACATCTCTGCGTAC
CTCCTTAGCAAGAATAACGCCATCGAGCCAAGATCCTTCAGCCAGAACCCCCAGTGCTGAAGAGG
CATCAGCGGGAGATCACCCGCACGACCCTGCAGTCGGATCAGGAGGAGATTGATTACGACGACACG
ATCAGTGTGGAGATGAAGAAGGAGGACTTCGACATCTACGACGAAGATGAAAACCAGTCCCTCGG
TCCTTCCAAAAGAAGACCCGGCACTACTTCATCGCCGCTGTGGAACGCCTGTGGGACTATGGAATG
```

```
TCTTCTAGCCCTCACGTTTTGAGGAACCGCGCCCAGTCGGGCAGCGTGCCCCAGTTCAAGAAAGTG
GTGTTCCAGGAGTTCACCGACGGCTCCTTCACCCAGCCACTTTACCGGGGCGAGCTCAATGAACAT
CTGGGCCTGCTGGGACCCTACATCAGGGCTGAGGTGGAGGACAACATCATGGTGACATTCCGGAAT
CAGGCCAGCAGACCATACAGTTTCTACAGTTCACTCATCTCCTACGAGGAGGACCAGCGCCAGGGG
GCTGAACCCCGTAAGAACTTCGTGAAGCCAAACGAAACAAAGACCTACTTCTGGAAGGTCCAGCAC
CACATGGCACCTACCAAGGACGAGTTCGATTGCAAGGCCTGGGCCTACTTCTCCGACGTGGACCTG
GAGAAAGATGTGCACAGCGGCCTGATTGGCCCTCTGCTGGTGTGTCACACGAACACACTCAACCCT
GCACACGGGCGGCAGGTCACTGTGCAGGAATTCGCCCTGTTCTTTACCATCTTTGATGAGACGAAG
TCCTGGTATTTCACCGAAAACATGGAGAGGAACTGCCGCGCACCCTGCAACATCCAGATGGAAGAT
CCGACATTCAAGGAGAACTACCGGTTCCATGCCATCAATGGCTACATCATGGACACCCTGCCTGGC
CTCGTGATGGCCCAAGACCAGCGTATCCGCTGGTATCTGCTGTCGATGGGCTCCAACGAGAACATC
CATAGTATCCACTTCAGCGGGCATGTCTTCACGGTGAGGAAAAAGGAGGAGTACAAGATGGCACTG
TACAACCTCTATCCCGGCGTGTTCGAGACCGTGGAGATGCTGCCCTCCAAGGCCGGCATCTGGAGA
GTGGAATGCCTGATCGGCGAGCACCTCCACGCTGGGATGTCCACGCTGTTCCTCGTTTACAGCAAT
AAGTGCCAGACCCCTCTGGGCATGGCGAGCGGCCACATCCGCGACTTCCAGATTACAGCCAGCGGC
CAGTACGGTCAGTGGGCTCCAAAGCTGGCCCGTCTGCACTACTCCGGATCCATCAACGCCTGGTCC
ACCAAGGAACCGTTCTCCTGGATCAAAGTAGACCTGCTAGCCCCCATGATCATTCACGGCATCAAG
ACACAAGGCGCCCGACAGAAGTTCTCGAGCCTCTATATCTCCCAGTTCATCATCATGTATAGCCTG
GACGGAAAGAAGTGGCAGACTTACCGCGGAAACTCGACAGGGACCCTGATGGTATTCTTCGGTAAC
GTGGACAGCTCCGGAATCAAGCACAACATCTTCAACCCACCCATTATCGCCCGCTACATCCGCCTG
CACCCCACTCACTATAGCATTAGGTCCACCCTGCGAATGGAGCTCATGGGCTGTGACCTGAACAGC
TGTAGCATGCCCCTCGGCATGGAGTCTAAGGCGATCTCCGACGCACAGATAACGGCATCATCCTAC
TTTACCAACATGTTCGCTACCTGGTCCCCCTCCAAGGCCCGACTCCACCTGCAAGGGAGATCCAAC
GCCTGGCGGCCACAGGTCAACAATCCCAAGGAGTGGCTGCAAGTGGACTTTCAGAAAACTATGAAA
GTCACCGGAGTGACCACACAGGGAGTGAAGTCTCTGCTGACCAGCATGTACGTGAAGGAGTTCCTC
ATCTCCAGTTCGCAGGATGGCCACCAGTGGACGTTGTTCTTCCAAAACGGTAAAGTCAAAGTCTTC
CAAGGGAACCAGGACAGCTTTACACCCGTCGTGAACTCCCTGGACCCCCGCTTCTCACTAGATAC
CTCCGCATCCACCCTCAGAGCTGGGTGCACCAGATTGCCCTGCGCATGGAGGTTCTGGGGTGTGAA
GCCCAGGACCTGTACTAA (SEQ ID NO:7)
```

```
ATGCAGATTGAGCTCTCCACCTGCTTCTTTCTCTGCCTTCTTCGCTTCTGCTTTTCTGCCACACGC
AGGTACTATTTGGGAGCAGTGGAACTGAGCTGGGATTACATGCAGAGTGACCTTGGTGAACTTCCT
GTGGACGCTCGTTTTCCACCTAGAGTTCCCAAGTCCTTCCCCTTCAACACCTCAGTGGTCTACAAG
AAAACGCTGTTTGTGGAGTTCACTGACCACCTCTTCAACATTGCCAAACCAAGACCCCCTTGGATG
GGATTGCTGGGACCCACAATACAAGCAGAAGTCTACGACACGGTGGTGATTACCCTGAAGAACATG
GCGTCACACCCTGTTTCACTTCACGCTGTTGGGGTCAGTTATTGGAAAGCCTCAGAGGGTGCGGAA
TACGATGATCAAACCAGCCAGAGGGAGAAGGAAGATGACAAGGTCTTTCCTGGGGGTAGCCATACC
TATGTTTGGCAGGTGCTGAAAGAGAATGGGCCTATGGCCTCTGATCCCTTGTGCCTCACATACTCT
TACCTGAGTCACGTCGACCTGGTGAAAGACCTGAATAGCGGTCTGATTGGTGCACTGCTTGTTTGT
AGAGAGGGGAGTTTGGCCAAGGAGAAAACTCAGACTCTCCACAAGTTTATCCTCCTGTTTGCTGTG
TTCGACGAGGGCAAGTCTTGGCACTCTGAAACAAAGAACTCCCTGATGCAGGACAGAGATGCTGCA
TCTGCAAGGGCTTGGCCAAAAATGCACACAGTGAACGGCTATGTGAATCGATCACTGCCAGGACTG
ATAGGCTGTCATCGCAAGTCAGTGTATTGGCACGTTATCGGGATGGGAACAACTCCAGAAGTGCAC
AGCATCTTCCTTGAGGGCCACACTTTCCTGGTTCGGAATCATAGACAGGCCAGCCTTGAGATCAGC
CCAATCACCTTTCTGACTGCCCAAACCTTGCTGATGGATCTGGGACAGTTCCTCCTGTTTTGTCAC
ATCTCCTCCCACCAACATGACGGGATGGAGGCTTATGTGAAGGTCGATAGCTGTCCGGAGGAACCA
CAACTGAGGATGAAGAACAACGAAGAGGCAGAGGACTATGACGACGATCTGACTGACAGTGAAATG
GACGTGGTTCGGTTCGACGATGACAATTCTCCTTCATTTATCCAGATCCGTTCCGTGGCCAAGAAG
CACCCCAAGACTTGGGTTCATTACATCGCTGCTGAGGAGGAGGATTGGGACTACGCGCCCTTGGTG
TTGGCCCCAGACGATCGCTCATACAAGAGCCAGTACCTTAACAATGGTCCACAAAGGATCGGCCGG
AAGTACAAGAAGGTTAGATTTATGGCTTATACCGACGAGACTTTTAAAACTAGGGAAGCAATTCAG
CATGAAAGTGGCATTCTTGGACCCCTGCTGTATGGCGAGGTTGGCGACACCCTGCTGATTATCTTT
AAGAACCAGGCAAGCCGGCCCTACAACATCTACCCGCACGGCATAACCGATGTACGACCCCTGTAC
AGTCGCAGACTTCCTAAAGGGGTGAAACACCTGAAGGACTTCCCAATTCTGCCCGGGGAGATCTTC
AAGTATAAATGGACCGTGACGGTTGAGGATGGTCCCACAAAGTCCGATCCGAGATGCCTTACCCGA
TATTATTCCAGCTTCGTGAACATGGAAAGGGACCTGGCCAGCGGGCTGATTGCCCACTGCTGATT
TGTTACAAGGAGTCTGTCGATCAAAGAGGAAACCAAATAATGAGCGACAAACGTAACGTCATCCTG
TTCAGCGTCTTTGATGAGAATAGAAGCTGGTACCTCACAGAAATATTCAGCGGTTCTGCCTAAC
CCCGCAGGCGTCCAGCTGGAAGATCCCGAGTTCCAAGCCTCAAACATCATGCATAGCATCAACGGA
TACGTATTCGATAGCCTGCAGCTGTCCGTCTGTCTCCATGAAGTGGCATATTGGTACATCCTGAGT
ATCGGGGCGCAGACCGACTTCCTGAGCGTGTTCTTTTCTGGATACACGTTCAAACACAAAATGGTC
TATGAAGATACCCTGACTCTGTTTCCATTCTCAGGAGAGACAGTCTTTATGAGTATGGAAAATCCT
GGACTGTGGATCCTGGGCTGTCACAATTCTGATTTTCGGAACAGAGGCATGACAGCCCTGCTTAAA
GTGAGCTCATGCGACAAGAACACCGGTGATTACTACGAAGATAGCTATGAGGACATCAGTGCGTAT
TTGCTCTCCAAGAACAACGCTATCGAGCCACGGTCTTTCAGTCAGAATCCTCCCGTTCTGAAGCGG
CATCAGCGCGAAATAACACGCACAACCCTTCAGTCAGACCAAGAGGAAATCGACTACGATGATACT
ATCTCTGTGGAGATGAAGAAGGAGGATTTCGACATTTACGACGAGGACGAGAATCAGTCCCCAAGG
AGCTTTCAGAAGAAAACAAGACACTATTTCATTGCCGCCGTGGAGCGACTGTGGGACTACGGCATG
```

```
TCTAGCTCTCCGCATGTACTTAGAAATAGGGCACAAAGCGGATCCGTGCCTCAGTTTAAGAAAGTT
GTCTTTCAGGAGTTTACAGATGGCTCCTTCACCCAGCCCTTGTATCGCGGGGAACTCAATGAACAC
CTGGGCCTCCTGGGTCCTTATATTAGGGCCGAAGTCGAGGACAATATCATGGTGACCTTTAGGAAC
CAGGCATCTAGACCTTACTCTTTCTACTCCTCCCTGATATCCTATGAGGAGGACCAGCGGCAAGGC
GCTGAGCCTCGGAAGAACTTTGTGAAGCCAAATGAAACCAAAACATACTTTTGGAAAGTTCAGCAC
CACATGGCTCCCACGAAGGACGAATTTGACTGTAAAGCCTGGGCCTACTTCTCAGATGTAGATCTC
GAGAAAGACGTGCACTCAGGGCTCATTGGTCCCCTCCTGGTCTGTCATACTAATACCCTCAATCCA
GCACACGGACGTCAGGTAACCGTCCAGGAATTTGCCCTGTTCTTTACCATTTTCGATGAGACTAAA
TCCTGGTACTTTACCGAAAACATGGAGAGGAATTGCAGAGCCCCATGCAACATCCAGATGGAGGAC
CCTACCTTCAAAGAGAACTATCGCTTCCATGCCATTAACGGTTACATTATGGATACTCTCCCAGGA
CTTGTGATGGCACAGGATCAGCGGATAAGATGGTATCTGTTGAGCATGGGCTCCAACGAGAATATT
CACAGCATCCATTTCTCCGGTCACGTGTTTACAGTGAGAAAGAAAGAAGAGTACAAGATGGCTCTG
TATAATCTCTATCCAGGCGTATTCGAAACGGTGGAGATGTTGCCTAGCAAGGCCGGCATTTGGCGA
GTAGAATGCCTTATCGGGGAACATCTGCATGCCGGAATGAGCACGCTCTTCCTGGTGTATAGTAAC
AAGTGCCAGACTCCGCTGGGCATGGCATCTGGCCATATACGGGACTTTCAGATTACGGCTAGCGGG
CAGTATGGGCAGTGGGCACCCAAACTTGCGCGACTGCACTATTCAGGCTCTATCAATGCATGGTCC
ACCAAGGAACCCTTCTCTTGGATTAAGGTGGACCTTTTGGCGCCCATGATAATCCATGGGATCAAA
ACCCAGGGCGCTCGTCAGAAATTCTCATCACTCTACATCTCTCAGTTCATAATAATGTATTCACTG
GATGGGAAGAAATGGCAGACTTACAGAGGAAACAGCACCGGGACGCTGATGGTGTTCTTTGGCAAC
GTGGACAGCAGCGGCATCAAACACAACATCTTCAATCCTCCCATTATTGCCCGTTATATTAGACTG
CATCCCACTCACTACTCTATACGCAGCACACTTAGGATGGAGCTCATGGGATGCGACCTGAACAGT
TGTAGTATGCCCTTGGGGATGGAGTCCAAAGCTATAAGCGACGCACAAATTACAGCTAGCTCTTAC
TTTACGAATATGTTCGCCACGTGGAGCCCAAGCAAAGCCCGGCTGCATTTGCAGGGTCGGAGTAAT
GCTTGGCGCCCACAGGTGAATAACCCTAAGGAATGGTTGCAAGTAGATTCCAGAAAACTATGAAG
GTAACCGGCGTCACTACACAGGGAGTCAAGTCCCTCTTGACCTCTATGTACGTCAAGGAGTTCCTG
ATTAGCAGCAGTCAGGATGGGCACCAATGGACACTGTTCTTCCAGAATGGGAAAGTTAAAGTATTT
CAGGGTAACCAGGACTCCTTTACACCTGTGGTGAATAGCCTCGACCCACCCCTGCTGACACGATAC
CTCCGCATCCACCCTCAGTCTTGGGTGCATCAAATTGCCCTGCGAATGGAGGTGTTGGGATGCGAA
GCTCAGGACCTCTACTGA (SEQ ID NO:8)
```

```
ATGCAGATCGAACTCTCTACTTGCTTCTTCCTGTGCCTTCTGAGGTTCTGCTTCTCTGCCACTCGC
CGATATTACCTCGGGGCCGTGGAGTTGAGTTGGGACTACATGCAATCAGATCGGGCGAACTCCCT
GTGGATGCCCGATTCCCACCGCGCGTGCCCAAGTCTTTCCCATTTAATACTTCTGTGGTGTACAAG
AAGACATTGTTTGTGGAGTTTACCGATCACCTGTTCAACATCGCCAAACCGCGGCCCCATGGATG
GGTCTGCTTGGGCCCACCATTCAAGCGGAGGTCTATGATACAGTGGTGATAACGCTTAAGAACATG
GCGAGCCACCCAGTGTCTCTGCATGCCGTTGGTGTATCATATTGGAAGGCCAGCGAAGGAGCGGAG
TACGATGACCAGACCTCTCAGAGAGAGAAGGAAGACGATAAGGTTTTTCCTGGCGGAAGTCATACA
TATGTATGGCAGGTCCTGAAAGAGAATGGGCCGATGGCTTCTGACCCCCTTTGTCTTACCTATAGT
TATCTGAGCCACGTGGACCTGGTCAAGGACCTCAACAGTGGTCTGATTGGGGCTCTGCTTGTTTGT
AGAGAGGGTAGCTTGGCTAAGGAGAAAACCCAAACACTCCATAAGTTCATTTTGCTGTTCGCGGTG
TTCGACGAGGGAAAGAGTTGGCACAGCGAAACAAAGAATTCACTGATGCAAGACAGGGACGCCGCT
TCCGCAAGGGCTTGGCCTAAGATGCATACGGTGAATGGGTATGTGAACCGGAGCCTCCCGGGGCTG
ATCGGGTGCCATCGCAAGTCTGTTTACTGGCACGTCATTGGAATGGGGACAACGCCAGAGGTACAT
AGTATATTTCTTGAAGGCCACACGTTCCTCGTACGGAACCACCGACAGGCTTCCCTGGAGATAAGC
CCCATTACCTTTCTGACCGCTCAGACTCTGCTGATGGACCTTGGCCAGTTTCTCCTGTTCTGCCAT
ATTAGCAGCCACCAGCACGACGGTATGGAAGCATACGTGAAAGTCGATAGCTGTCCTGAGGAGCCT
CAGCTCAGAATGAAGAACAACGAGGAGGCCGAAGACTATGACGATGACCTTACAGATTCCGAGATG
GACGTGGTGCGCTTTGACGACGATAACAGTCCTAGTTTCATTCAAATCAGATCCGTAGCCAAAAAG
CATCCAAAGACATGGGTGCATTACATTGCAGCCGAAGAGGAGGATTGGGATTATGCGCCCCTTGTT
CTGGCTCCAGATGACAGGAGCTATAAGTCCCAGTACTTGAACAACGGGCCACAGCGAATCGGTAGA
AAATATAAGAAGGTAAGATTCATGGCCTACACTGACGAAACATTTAAAACCAGGGAAGCTATCCAA
CACGAATCTGGAATTCTCGGCCCTCTGCTCTACGGTGAGGTGGGGGACACCTTGCTGATCATTTTC
AAAAATCAGGCATCCAGGCCTTACAACATATACCCCATGGCATCACCGATGTCCGCCCGCTGTAT
TCCAGAAGACTCCCCAAGGGAGTGAAACATCTGAAAGATTTTCCCATCCTGCCGGGCGAGATCTTT
AAATACAAATGGACTGTGACTGTAGAGGACGGGCCTACAAAATCAGACCCACGGTGCCTGACAAGG
TATTACAGTAGCTTCGTCAACATGGAACGCGACCTCGCCAGCGGACTCATTGGCCCACTGTTGATC
TGTTACAAAGAGTCAGTGGATCAGAGGGGAAATCAGATCATGAGCGATAAGAGAAACGTTATCCTG
TTTAGTGTCTTCGACGAGAACCGGTCTTGGTACCTTACTGAGAACATCCAGAGGTTCCTGCCGAAT
CCGGCTGGCGTTCAGCTCGAGGACCCAGAGTTCCAGGCCAGTAATATAATGCACTCAATCAACGGT
TATGTGTTCGATAGCCTGCAGCTGAGCGTCTGCCTCCACGAGGTAGCCTATTGGTACATATTGTCC
ATCGGGCTCAGACCGATTTCTGTCCGTGTTCTTTAGCGGGTATACCTTTAAACATAAAATGGTC
TATGAAGACACCCTGACCCTGTTCCCATTCTCCGGTGAGACTGTGTTCATGTCCATGGAGAACCCA
GGGCTGTGGATCCTGGGGTGTCACAATAGTGACTTTAGGAATCGGGGAATGACGGCACTGCTGAAG
GTGAGTTCTTGCGATAAAAATACAGGAGATTACTATGAGGATAGTTACGAGGATATCAGTGCCTAT
CTGCTTTCAAAAACAACGCAATTGAGCCCCGGTCTTTCTCACAAAACCCCCGGTGCTGAAGCGC
CACCAGCGCGAAATTACCCGGACAACCTTGCAGTCCGACCAGGAGGAAATCGATTATGACGATACT
ATCAGTGTAGAAATGAAAAGGAGGATTTTGATATTTACGACGAAGACGAGAACCAGTCTCCGCGA
```

```
AGTTTTCAGAAGAAAACGCGACACTACTTTATAGCTGCCGTGGAACGACTCTGGGATTATGGCATG
TCCTCCAGCCCTCATGTCCTTAGGAATCGAGCGCAGAGTGGCTCTGTGCCTCAGTTCAAAAAGGTT
GTGTTCCAGGAATTCACCGACGGCTCATTTACCCAGCCGCTGTACAGAGGCGAACTCAACGAACAC
CTTGGGCTGCTTGGGCCATATATTCGAGCAGAGGTGGAAGATAATATCATGGTAACCTTTAGAAAC
CAGGCGTCAAGACCCTATTCCTTCTACAGTTCTCTGATCAGCTACGAGGAGGACCAAAGACAGGGA
GCTGAACCCAGGAAGAACTTTGTGAAACCTAATGAGACCAAGACCTACTTCTGGAAGGTCCAGCAC
CATATGGCCCCAACTAAAGATGAATTCGATTGCAAGGCCTGGGCTTATTTCAGCGACGTGGATCTC
GAAAAGGATGTGCACAGCGGGTTGATCGGACCGCTTTTGGTGTGCCACACAAATACCCTCAATCCT
GCCCACGGGCGGCAGGTCACAGTTCAAGAGTTTGCACTCTTCTTTACAATATTTGACGAGACAAAG
TCATGGTATTTTACAGAGAATATGGAGAGAAATTGTCGCGCACCTTGCAACATTCAGATGGAGGAC
CCCACATTTAAGGAGAATTACAGATTTCATGCTATCAATGGGTACATTATGGATACTCTGCCTGGT
CTGGTCATGGCCCAGGATCAGCGCATAAGGTGGTACTTGCTGAGCATGGGATCTAATGAGAATATA
CACAGCATTCACTTCAGTGGCCACGTTTTACTGTTAGAAAGAAGGAGGAGTACAAAATGGCGCTC
TACAACCTTTACCCGGGTGTGTTTGAGACAGTGGAGATGCTGCCAAGCAAGGCAGGCATCTGGAGG
GTTGAGTGTCTTATTGGGGAGCATCTGCATGCTGGAATGTCCACCCTCTTTCTTGTGTACAGCAAT
AAGTGCCAGACACCGCTTGGCATGGCCAGCGGCCACATTAGGGACTTTCAGATAACTGCCAGTGGA
CAGTACGGCCAGTGGGCTCCCAAGCTTGCAAGACTCCACTACTCCGGAAGCATAAACGCATGGAGC
ACCAAGGAACCCTTCTCTTGGATTAAGGTGGACCTGCTGGCGCCAATGATCATTCACGGCATAAAA
ACCCAAGGGGCACGACAGAAATTTTCATCTTTGTATATTAGTCAGTTTATCATCATGTACAGCTTG
GATGGAAAGAAGTGGCAGACGTACAGGGGCAATTCTACAGGAACACTTATGGTGTTTTTGGGAAT
GTCGATTCCAGCGGGATCAAACATAACATCTTCAATCCTCCTATTATCGCCCGATATATCCGCCTG
CACCCTACGCATTACTCCATCAGGTCCACATTGAGAATGGAACTGATGGGGTGCGACCTGAATAGT
TGTAGTATGCCACTGGGCATGGAGTCTAAAGCCATCAGCGATGCACAGATCACTGCCAGCTCTTAC
TTCACCAACATGTTTGCAACTTGGTCCCCTCTAAAGCTCGCCTGCATCTGCAGGGACGCTCAAAT
GCATGGCGACCACAGGTGAACAATCCAAAAGAGTGGCTCCAGGTCGACTTTCAGAAGACAATGAAG
GTAACAGGAGTGACAACCCAGGGTGTAAAAGCCTCCTTACGAGTATGTACGTTAAGGAGTTTCTG
ATTTCTAGCTCCCAGGACGGACACCAGTGGACTCTGTTCTTCCAGAACGGCAAAGTGAAGGTATTT
CAGGGAAACCAGGATTCTTTTACCCCGGTAGTGAATAGCCTGGATCCACCGTTGCTGACCCGCTAT
CTGAGAATTCATCCACAATCCTGGGTGCATCAGATTGCCCTCCGGATGGAAGTGCTCGGCTGTGAA
GCTCAGGATCTGTATTAG (SEQ ID NO:9)
```

```
ATGCAAATAGAGCTCTCCACCTGCTTCTTTCTGTGCCTTTTGCGATTCTGCTTTAGTGCCACCAGA
AGATACTACCTGGGTGCAGTGGAACTGTCATGGGACTATATGCAAAGTGATCTCGGTGAGCTGCCT
GTGGACGCAAGATTTCCTCCTAGAGTGCCAAAATCTTTTCCATTCAACACCTCAGTCGTGTACAAA
AAGACTCTGTTTGTAGAATTCACGGATCACCTTTTCAACATCGCTAAGCCAAGGCCACCCTGGATG
GGTCTGCTAGGTCCTACCATCCAGGCTGAGGTTTATGATACAGTGGTCATTACACTTAAGAACATG
GCTTCCCATCCTGTCAGTCTTCATGCTGTTGGTGTATCCTACTGGAAAGCTTCTGAGGGAGCTGAA
TATGATGATCAGACCAGTCAAAGGGAGAAGAAGATGATAAAGTCTTCCCTGGTGGAAGCCATACA
TATGTCTGGCAGGTCCTGAAAGAGAATGGTCCAATGGCCTCTGACCCACTGTGCCTTACCTACTCA
TATCTTTCTCATGTGGACCTGGTAAAAGACTTGAATTCAGGCCTCATTGGAGCCCTACTAGTATGT
AGAGAAGGGAGTCTGGCCAAGGAAAAGACACAGACCTTGCACAAATTTATACTACTTTTTGCTGTA
TTTGATGAAGGGAAAAGTTGGCACTCAGAAACAAAGAACTCCTTGATGCAGGATAGGGATGCTGCA
TCTGCTCGGGCCTGGCCTAAAATGCACACAGTCAATGGTTATGTAAACAGGTCTCTGCCAGGTCTG
ATTGGATGCCACAGGAAATCAGTCTATTGGCATGTGATTGGAATGGGCACCACTCCTGAAGTGCAC
TCAATATTCCTCGAAGGTCACACATTTCTTGTGAGGAACCATCGCCAGGCGTCCTTGGAAATCTCG
CCAATAACTTTCCTTACTGCTCAAACACTCTTGATGGACCTTGGACAGTTTCTACTGTTTTGTCAT
ATCTCTTCCCACCAACATGATGGCATGGAAGCTTATGTCAAAGTAGACAGCTGTCCAGAGGAACCC
CAACTACGAATGAAAAATAATGAAGAAGCGGAAGACTATGATGATGATCTTACTGATTCTGAAATG
GATGTGGTCAGGTTTGATGATGACAACTCTCCTTCCTTTATCCAAATTCGCTCAGTTGCCAAGAAG
CATCCTAAAACTTGGGTACATTACATTGCTGCTGAAGAGGAGGACTGGGACTATGCTCCCTTAGTC
CTCGCCCCCGATGACAGAAGTTATAAAAGTCAATATTTGAACAATGGCCCTCAGCGGATTGGTAGG
AAGTACAAAAAGTCCGATTTATGGCATACACAGATGAAACCTTTAAGACTCGTGAAGCTATTCAG
CATGAATCAGGAATCTTGGGACCTTTACTTTATGGGGAAGTTGGAGACACACTGTTGATTATATTT
AAGAATCAAGCAAGCAGACCATATAACATCTACCCTCACGGAATCACTGATGTCCGTCCTTTGTAT
TCAAGGAGATTACCAAAAGGTGTAAAACATTTGAAGGATTTTCCAATTCTGCCAGGAGAAATATTC
AAATATAAATGGACAGTGACTGTAGAAGATGGGCCAACTAAATCAGATCCTCGGTGCCTGACCCGC
TATTACTCTAGTTTCGTTAATATGGAGAGAGATCTAGCTTCAGGACTCATTGGCCCTCTCCTCATC
TGCTACAAAGAATCTGTAGATCAAAGAGGAAACCAGATAATGTCAGACAAGAGGAATGTCATCCTG
TTTTCTGTATTTGATGAGAACCGAAGCTGGTACCTCACAGAGAATATACAACGCTTTCTCCCCAAT
CCAGCTGGAGTGCAGCTTGAGGATCCAGAGTTCCAAGCCTCCAACATCATGCACAGCATCAATGGC
TATGTTTTTGATAGTTTGCAGTTGTCAGTTTGTTTGCATGAGGTGGCATACTGGTACATTCTAAGC
ATTGGAGCACAGACTGACTTCCTTTCTGTCTTCTTCTCTGGATATACCTTCAAACACAAAATGGTC
TATGAAGACACACTCACCCTATTCCCATTCTCAGGAGAAACTGTCTTCATGTCGATGGAAAACCCA
GGTCTATGGATTCTGGGGTGCCACAACTCAGACTTTCGGAACAGAGGCATGACCGCCTTACTGAAG
GTTTCTAGTTGTGACAAGAACACTGGTGATTATTACGAGGACAGTTATGAAGATATTTCAGCATAC
TTGCTGAGTAAAAACAATGCCATTGAACCAAGAAGCTTCTCCCAGAATCCACCAGTCTTGAAACGC
CATCAACGGGAATAACTCGTACTACTCTTCAGTCAGATCAAGAGGAAATTGACTATGATGATACC
ATATCAGTTGAAATGAAGAAGGAAGATTTTGACATTTATGATGAGGATGAAAATCAGAGCCCCGC
AGCTTTCAAAAGAAAACACGACACTATTTTATTGCTGCAGTGGAGAGGCTCTGGGATTATGGGATG
```

```
AGTAGCTCCCCACATGTTCTAAGAAACAGGGCTCAGAGTGGCAGTGTCCCTCAGTTCAAGAAAGTT
GTTTTCCAGGAATTTACTGATGGCTCCTTTACTCAGCCCTTATACCGTGGAGAACTAAATGAACAT
TTGGGACTCCTGGGGCCATATATAAGAGCAGAAGTTGAAGATAATATCATGGTAACTTTCAGAAAT
CAGGCCTCTCGTCCCTATTCCTTCTATTCTAGCCTTATTTCTTATGAGGAAGATCAGAGGCAAGGA
GCAGAACCTAGAAAAAACTTTGTCAAGCCTAATGAAACCAAAACTTACTTTTGGAAAGTGCAACAT
CATATGGCACCCACTAAAGATGAGTTTGACTGCAAAGCCTGGGCTTATTTCTCTGATGTTGACCTG
GAAAAGATGTGCACTCAGGCCTGATTGGACCCCTTCTGGTCTGCCACACTAACACACTGAACCCT
GCTCATGGGAGACAAGTGACAGTACAGGAATTTGCTCTGTTTTCACCATCTTTGATGAGACCAAA
AGCTGGTACTTCACTGAAAATATGGAAAGAAACTGCAGGGCTCCCTGCAATATCCAGATGGAAGAT
CCCACTTTTAAAGAGAATTATCGCTTCCATGCAATCAATGGCTACATAATGGATACACTACCTGGC
TTAGTAATGGCTCAGGATCAAAGGATTCGATGGTATCTGCTCAGCATGGGCAGCAATGAAAACATC
CATTCTATTCATTTCAGTGGACATGTGTTCACTGTACGAAAAAAGAGGAGTATAAAATGGCACTG
TACAATCTCTATCCAGGTGTTTTTGAGACAGTGGAAATGTTACCATCCAAAGCTGGAATTTGGCGG
GTGGAATGCCTTATTGGCGAGCATCTACATGCTGGGATGAGCACACTTTTTCTGGTGTACAGCAAT
AAGTGTCAGACTCCCCTGGGAATGGCTTCTGGACACATTAGAGATTTTCAGATTACAGCTTCAGGA
CAATATGGACAGTGGGCCCCAAAGCTGGCCAGACTTCATTATTCCGGATCAATCAATGCCTGGAGC
ACCAAGGAGCCCTTTTCTTGGATCAAGGTGGATCTGTTGGCACCAATGATTATTCACGGCATCAAG
ACCCAGGGTGCCCGTCAGAAGTTCTCCAGCCTCTACATCTCTCAGTTTATCATCATGTATAGTCTT
GATGGGAAGAAGTGGCAGACTTATCGAGGAAATTCCACTGGAACCTTAATGGTCTTCTTTGGCAAT
GTGGATTCATCTGGGATAAAACACAATATTTTTAACCCTCCAATTATTGCTCGATACATCCGTTTG
CACCCAACTCATTATAGCATTCGCAGCACTCTTCGCATGGAGTTGATGGGCTGTGATTTAAATAGT
TGCAGCATGCCATTGGGAATGGAGAGTAAAGCAATATCAGATGCACAGATTACTGCTTCATCCTAC
TTTACCAATATGTTTGCCACCTGGTCTCCTTCAAAAGCTCGACTTCACCTCCAAGGGAGGAGTAAT
GCCTGGAGACCTCAGGTGAATAATCCAAAAGAGTGGCTGCAAGTGGACTTCCAGAAGACAATGAAA
GTCACAGGAGTAACTACTCAGGGAGTAAAATCTCTGCTTACCAGCATGTATGTGAAGGAGTTCCTC
ATCTCCAGCAGTCAAGATGGCCATCAGTGGACTCTCTTTTTCAGAATGGCAAAGTAAAGGTTTTT
CAGGGAAATCAAGACTCCTTCACACCTGTGGTGAACTCTCTAGACCCACCGTTACTGACTCGCTAC
CTTCGAATTCACCCCAGAGTTGGGTGCACCAGATTGCCCTGAGGATGGAGGTTCTGGGCTGCGAG
GCACAGGACCTCTACTGA (SEQ ID NO:10)
```

```
ATGCAGATCGAGCTGTCCACATGCTTTTTTCTGTGCCTGCTGCGGTTCTGCTTCAGCGCCACCCGG
CGGTACTACCTGGGCGCCGTGGAGCTGTCCTGGGACTACATGCAGAGCGACCTGGGCGAGCTGCCC
GTGGACGCCCGGTTCCCCCCCAGAGTGCCCAAGAGCTTCCCCTTCAACACCAGCGTGGTGTACAAG
AAAACCCTGTTCGTGGAGTTCACCGACCACCTGTTCAACATCGCCAAGCCCAGGCCCCCCTGGATG
GGCCTGCTGGGCCCCACCATCCAGGCCGAGGTGTACGACACCGTGGTGATCACCCTGAAGAACATG
GCCAGCCACCCCGTGAGCCTGCACGCCGTGGGCGTGAGCTACTGGAAGGCCTCCGAGGGCGCCGAG
TACGACGACCAGACCAGCCAGCGGGAGAAGAGGACGACAAAGTCTTTCCTGGCGGCAGCCACACC
TACGTGTGGCAGGTCCTGAAAGAAAACGGCCCCATGGCCTCCGACCCCCTGTGCCTGACCTACAGC
TACCTGAGCCACGTGGACCTGGTGAAGGACCTGAACAGCGGGCTGATTGGGGCCCTGCTGGTCTGC
CGGGAGGGCAGCCTGGCCAAAGAGAAAACCCAGACCCTGCACAAGTTCATCCTGCTGTTCGCCGTG
TTCGACGAGGGCAAGAGCTGGCACAGCGAGACCAAGAACAGCCTGATGCAGGACCGGGACGCCGCC
TCTGCCAGAGCCTGGCCCAAGATGCACACCGTGAACGGCTACGTGAACAGAAGCCTGCCCGGCCTG
ATTGGCTGCCACCGGAAGAGCGTGTACTGGCACGTGATCGGCATGGGCACCACACCCGAGGTGCAC
AGCATCTTTCTGGAAGGGCACACCTTTCTGGTGCGGAACCACCGGCAGGCCAGCCTGGAAATCAGC
CCTATCACCTTCCTGACCGCCCAGACACTGCTGATGGACCTGGGCCAGTTCCTGCTGTTTTGCCAC
ATCAGCTCTCACCAGCACGACGGCATGGAAGCCTACGTGAAGGTGGACTCCTGCCCCGAGGAACCC
CAGCTGCGGATGAAGAACAACGAGGAAGCCGAGGACTACGACGACGACCTGACCGACAGCGAGATG
GACGTGGTGCGGTTCGACGACGACAACAGCCCCAGCTTCATCCAGATCAGAAGCGTGGCCAAGAAG
CACCCCAAGACCTGGGTGCACTACATCGCCGCCGAGGAAGAGGACTGGGACTACGCCCCCTGGTG
CTGGCCCCCGACGACAGAAGCTACAAGAGCCAGTACCTGAACAATGGCCCCCAGCGGATCGGCCGG
AAGTACAAGAAAGTGCGGTTCATGGCCTACACCGACGAGACCTTCAAGACCCGGGAGGCCATCCAG
CACGAGAGCGGCATCCTGGGCCCCCTGCTGTACGGCGAAGTGGGCGACACACTGCTGATCATCTTC
AAGAACCAGGCCAGCCGGCCCTACAACATCTACCCCACGGCATCACCGACGTGCGGCCCCTGTAC
AGCAGGCGGCTGCCCAAGGGCGTGAAGCACCTGAAGGACTTCCCCATCCTGCCCGGCGAGATCTTC
AAGTACAAGTGGACCGTGACCGTGGAGGACGGCCCCACCAAGAGCGACCCCAGATGCCTGACCCGG
TACTACAGCAGCTTCGTGAACATGGAACGGGACCTGGCCTCCGGGCTGATCGGACCTCTGCTGATC
TGCTACAAAGAAAGCGTGGACCAGCGGGGCAACCAGATCATGAGCGACAAGCGGAACGTGATCCTG
TTCAGCGTGTTCGATGAGAACCGGTCCTGGTATCTGACCGAGAACATCCAGCGGTTTCTGCCCAAC
CCTGCCGGGGTGCAGCTGGAAGATCCCGAGTTCCAGGCCAGCAACATCATGCACTCCATCAATGGC
TACGTGTTCGACAGCCTGCAGCTGTCCGTGTGTCTGCACGAGGTGGCCTACTGGTACATCCTGAGC
ATCGGCGCCCAGACCGACTTCCTGAGCGTGTTCTTCAGCGGCTACACCTTCAAGCACAAGATGGTG
TACGAGGACACCCTGACCCTGTTCCCTTTCAGCGGCGAGACCGTGTTCATGAGCATGGAAAACCCC
GGCCTGTGGATCCTGGGCTGCCACAACAGCGACTTCCGGAACCGGGGCATGACCGCCCTGCTGAAG
GTGTCCAGCTGCGACAAGAACACCGGCGACTACTACGAGGACAGCTACGAGGATATCAGCGCCTAC
CTGCTGTCCAAGAACAACGCCATCGAGCCCAGAAGCTTCAGCCAGAACCCCCTGTGCTGAAGCGG
CACCAGAGAGAGATCACCCGGACCACCCTGCAGTCCGACCAGGAAGAGATCGATTACGACGACACC
```

```
ATCAGCGTGGAGATGAAAAAAGAAGATTTCGACATCTACGACGAGGACGAGAACCAGAGCCCCCGG
TCCTTCCAGAAGAAAACCCGGCACTACTTTATCGCCGCCGTGGAGCGGCTGTGGGACTACGGCATG
AGCAGCAGCCCCCACGTGCTGCGGAACCGGGCCCAGAGCGGCAGCGTGCCCCAGTTCAAGAAAGTG
GTGTTCCAGGAATTCACCGACGGCAGCTTCACCCAGCCCCTGTACCGGGGCGAGCTGAACGAGCAC
CTGGGGCTGCTGGGGCCCTACATCAGGGCCGAAGTGGAGGACAACATCATGGTGACCTTCCGGAAT
CAGGCCAGCAGACCCTACTCCTTCTACAGCAGCCTGATCAGCTACGAAGAGGACCAGCGGCAGGGC
GCTGAACCCCGGAAGAACTTCGTGAAGCCCAATGAGACCAAGACCTACTTCTGGAAAGTGCAGCAC
CACATGGCCCCCACCAAGGACGAGTTCGACTGCAAGGCCTGGGCCTACTTCAGCGACGTGGATCTG
GAAAAGGACGTGCACTCTGGACTGATTGGCCCTCTGCTGGTGTGCCACACCAACACCCTGAACCCC
GCCCACGGCCGGCAGGTGACCGTGCAGGAATTCGCCCTGTTCTTCACCATCTTCGACGAGACCAAG
TCCTGGTACTTCACCGAGAATATGGAACGGAACTGCAGAGCCCCCTGCAACATCCAGATGGAAGAT
CCTACCTTCAAAGAGAACTACCGGTTCCACGCCATCAACGGCTACATCATGGACACCCTGCCTGGC
CTGGTGATGGCCCAGGACCAGAGGATCCGGTGGTATCTGCTGTCCATGGGCAGCAACGAGAATATC
CACAGCATCCACTTCAGCGGCCACGTGTTCACCGTGAGGAAGAAAGAAGAGTACAAGATGGCCCTG
TACAACCTGTACCCCGGCGTGTTCGAGACCGTGGAGATGCTGCCCAGCAAGGCCGGCATCTGGCGG
GTGGAGTGTCTGATCGGCGAGCACCTGCATGCCGGGATGAGCACCCTGTTTCTGGTGTACAGCAAC
AAGTGCCAGACCCCCCTGGGCATGGCCAGCGGCCACATCCGGGACTTCCAGATCACCGCCTCCGGC
CAGTACGGCCAGTGGGCCCCCAAGCTGGCCCGGCTGCACTACAGCGGCAGCATCAACGCCTGGTCC
ACCAAAGAGCCCTTCAGCTGGATCAAGGTGGACCTGCTGGCCCCTATGATCATCCACGGCATTAAG
ACCCAGGGCGCCAGGCAGAAGTTCAGCAGCCTGTACATCAGCCAGTTCATCATCATGTACAGCCTG
GACGGCAAGAAGTGGCAGACCTACCGGGGCAACAGCACCGGCACCCTGATGGTGTTCTTCGGCAAC
GTGGACAGCAGCGGCATCAAGCACAACATCTTCAACCCCCCCATCATCGCCCGGTACATCCGGCTG
CACCCCACCCACTACAGCATCAGATCCACCCTGCGGATGGAACTGATGGGCTGCGACCTGAACTCC
TGCAGCATGCCTCTGGGCATGGAAAGCAAGGCCATCAGCGACGCCCAGATCACAGCCAGCAGCTAC
TTCACCAACATGTTCGCCACCTGGTCCCCCTCCAAGGCCAGGCTGCACCTGCAGGGCCGGTCCAAC
GCCTGGCGGCCTCAGGTGAACAACCCCAAAGAATGGCTGCAGGTGGACTTTCAGAAAACCATGAAG
GTGACCGGCGTGACCACCCAGGGCGTGAAAAGCCTGCTGACCAGCATGTACGTGAAAGAGTTTCTG
ATCAGCAGCAGCCAGGACGGCCACCAGTGGACCCTGTTCTTTCAGAACGGCAAGGTGAAAGTGTTC
CAGGGCAACCAGGACTCCTTCACCCCCGTGGTGAACTCCCTGGACCCCCCCCTGCTGACCCGCTAC
CTGCGGATCCACCCCCAGTCTTGGGTGCACCAGATCGCCCTGAGGATGGAAGTGCTGGGATGTGAG
GCCCAGGATCTGTACTGA (SEQ ID NO:11)
```

FVIII-FL-AA

```
mqielstcff lcllrfcfsa trryylgave lswdymqsdl gelpvdarfp prvpksfpfn
tsvvykktlf veftdhlfni akprppwmgl lgptiqaevy dtvvitlknm ashpvslhav
gvsywkaseg aeyddqtsqr ekeddkvfpg gshtyvwqvl kengpmasdp lcltysylsh
vdlvkdlnsg ligallvcre gslakektqt lhkfillfav fdegkswhse tknslmqdrd
aasarawpkm htvngyvnrs lpgligchrk svywhvigmg ttpevhsifl eghtflvrnh
rqasleispi tfltaqtllm dlgqfllfch isshqhdgme ayvkvdscpe epqlrmknne
eaedydddlt dsemdvvrfd ddnspsfiqi rsvakkhpkt wvhyiaaeee dwdyaplvla
pddrsyksqy lnngpqrigr kykkvrfmay tdetfktrea iqhesgilgp llygevgdtl
liifknqasr pyniyphgit dvrplysrrl pkgvkhlkdf pilpgeifky kwtvtvedgp
tksdprcltr yyssfvnmer dlasgligpl licykesvdq rgnqimsdkr nvilfsvfde
nrswylteni qrflpnpagv qledpefqas nimhsingyv fdslqlsvcl hevaywyils
igaqtdflsv ffsgytfkhk mvyedtltlf pfsgetvfms menpglwilg chnsdfrnrg
mtallkvssc dkntgdyyed syedisayll sknnaieprs fsqnsrhpst rqkqfnatti
pendiektdp wfahrtpmpk iqnvsssdll mllrqspthh glslsdlqea kyetfsddps
pgaidsnnsl semthfrpql hhsgdmvftp esglqlrlne klgttaatel kkldfkvsst
snnlistips dnlaagtdnt sslgppsmpv hydsqldttl fgkkssplte sggplslsee
nndskllesg lmnsqesswg knvsstesgr lfkgkrahgp alltkdnalf kvsisllktn
ktsnnsatnr kthidgpsll ienspsvwqn ilesdtefkk vtplihdrml mdknatalrl
nhmsnkttss knmemvqqkk egpippdaqn pdmsffkmlf lpesarwiqr thgknslnsg
qgpspkqlvs lgpeksvegq nflseknkvv vgkgeftkdv glkemvfpss rnlfltnldn
lhennthnqe kkiqeeiekk et … # GENE THERAPY OF HEMOPHILIA A USING VIRAL VECTORS ENCODING RECOMBINANT FVIII VARIANTS WITH INCREASED EXPRESSION

CROSS REFERENCE TO RELATED APPLICATIONS

This application claims priority to U.S. Provisional Patent Application Ser. No. 62/698,680, filed Jul. 16, 2018, and claims priority to U.S. Provisional Patent Application Ser. No. 62/867,171, filed Jun. 26, 2019, both of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 15, 2019, is named 008073_5202_WO_Sequence_Listing.txt and is 85,000 bytes in size.

BACKGROUND OF THE DISCLOSURE

Blood coagulation proceeds through a complex and dynamic biological pathway of interdependent biochemical reactions, referred to as the coagulation cascade. Coagulation Factor VIII (FVIII) is a key component in the cascade. Factor VIII is recruited to bleeding sites, and forms a Xase complex with activated Factor IX (FIXa) and Factor X (FX). The Xase complex activates FX, which in turn activates prothrombin to thrombin, which then activates other components in the coagulation cascade to generate a stable clot (reviewed in Saenko et al., *Trends Cardiovasc. Med.,* 9:185-192 (1999); Lenting et al., *Blood,* 92:3983-3996 (1998)).

Hemophilia A is a congenital X-linked bleeding disorder characterized by a deficiency in Factor VIII activity. Diminished Factor VIII activity inhibits a positive feedback loop in the coagulation cascade. This causes incomplete coagulation, which manifests as bleeding episodes with increased duration, extensive bruising, spontaneous oral and nasal bleeding, joint stiffness and chronic pain, and possibly internal bleeding and anemia in severe cases (Zhang et al., *Clinic. Rev. Allerg. Immunol.,* 37:114-124 (2009)).

Conventionally, hemophilia A is treated by Factor VIII replacement therapy, which consists of administering Factor VIII protein (e.g., plasma-derived or recombinantly-produced Factor VIII) to an individual with hemophilia A. Factor VIII is administered prophylactically to prevent or reduce frequency of bleeding episodes, in response to an acute bleeding episode, and/or perioperatively to manage bleeding during surgery. However, there are several undesirable features of Factor VIII replacement therapy.

First, Factor VIII replacement therapy is used to treat or manage hemophilia A, but does not cure the underlying Factor VIII deficiency. Because of this, individuals with hemophilia A require Factor VIII replacement therapy for the duration of their lives. Continuous treatment is expensive and requires the individual to maintain strict compliance, as missing only a few prophylactic doses can have serious consequences for individuals with severe hemophilia A.

Second, because Factor VIII has a relatively short half-life in vivo, conventional prophylactic Factor VIII replacement therapy requires administration every second or third day. This places a burden on the individual to maintain compliance throughout their life. While third generation "long-acting" Factor VIII drugs may reduce the frequency of administration, prophylactic Factor FVIII replacement therapy with these drugs still requires monthly, weekly, or more frequent administration in perpetuity. For example, prophylactic treatment with ELOCTATE™ [Antihemophilic Factor (Recombinant), Fc Fusion Protein] requires administration every three to five days (ELOCTATE™ Prescribing Information, Biogen Idec Inc., (2015)). Moreover, the long-term effects of chemically modified biologics (e.g., pegylated polypeptides) are not yet fully understood.

Third, between 15% and 30% of all individuals receiving Factor VIII replacement therapy form anti-Factor VIII inhibitor antibodies, rendering the therapy inefficient. Factor VIII bypass therapy (e.g., administration of plasma-derived or recombinantly-produced prothrombin complex concentrates) can be used to treat hemophilia in individuals that form inhibitor antibodies. However, Factor VIII bypass therapy is less effective than Factor VIII replacement therapy (Mannucci P.M., J Thromb Haemost., 1(7):1349-55 (2003)) and may be associated with an increased risk of cardiovascular complication (Luu and Ewenstein, Haemophilia, 10 Suppl. 2:10-16 (2004)).

Somatic gene therapy holds great promise for the treatment of hemophilia A because it would remedy the underlying under-expression functional Factor VIII activity (e.g., due to missense or nonsense mutations), rather than provide a one-time dose of Factor VIII activity to the individual. Because of this difference in the mechanism of action, as compared to Factor VIII replacement therapy, one-time administration of a Factor VIII gene therapy vector may provide an individual with Factor VIII for several years, reducing the cost of treatment and eliminating the need for continued patient compliance.

Coagulation Factor IX (FIX) gene therapy has been used effectively to treat individuals with hemophilia B, a related blood coagulation condition characterized by diminished Factor IX activity (Manno C. S., et al., Nat Med., 12(3): 342-47 (2006)). However, Factor VIII gene therapy presents several unique challenges. For example, the full-length, wild-type Factor VIII polypeptide (2351 amino acids; UniProt accession number P00451) is five times larger than the full-length, wild-type Factor IX polypeptide (461 amino acids; UniProt accession number P00740). As such, the coding sequence of wild-type Factor VIII is 7053 base pairs, which is too large to be packaged in conventional AAV gene therapy vectors. Further, reported recombinant expression of B-domain deleted variants of Factor VIII (BDD-FVIII) has been poor. As such, several groups have attempted to alter the codon usage of BDD-FVIII constructs, with limited success.

BRIEF SUMMARY OF DISCLOSURE

Accordingly, there is a need for Factor VIII variants whose coding sequences are more efficiently packaged into, and delivered via, gene therapy vectors. There is also a need for synthetic, codon-altered nucleic acids which express Factor VIII more efficiently. Such Factor VIII variants and codon-altered nucleic acids allow for improved treatment of Factor VIII deficiencies (e.g., hemophilia A). The above deficiencies and other problems associated with the treatment of Factor VIII deficiencies (e.g., hemophilia A) are reduced or eliminated by the disclosed codon-altered Factor VIII variants.

In accordance with some embodiments, the present disclosure provides nucleic acids encoding Factor VIII variants that have high sequence identity to the disclosed codon-altered sequences of the Factor VIII heavy chain (e.g., CS04-HC-NA) and light chain (e.g., CS04-LC-NA). In some embodiments, these nucleic acids further include a sequence encoding a linker sequence that replaces the native Factor VIII B-domain (e.g., a linker sequences comprising a furin cleavage site), between the sequences coding for the Factor VIII heavy and light chains.

In one aspect, the disclosure provides a polynucleotide including a nucleotide sequence encoding a Factor VIII polypeptide. The Factor VIII polypeptide includes a light chain, a heavy chain, and a polypeptide linker joining the C-terminus of the heavy chain to the N-terminus of the light chain. The heavy chain of the Factor VIII polypeptide is encoded by a first nucleotide sequence having at least 95% identity to CS04-HC-NA (SEQ ID NO: 3). The light chain of the Factor FVIII polypeptide is encoded by a second nucleotide sequence having at least 95% identity to CS04-LC-NA (SEQ ID NO: 4). The polypeptide linker comprises a furin cleavage site.

In one embodiment of the polynucleotides described above, the polypeptide linker is encoded by a third nucleotide sequence having at least 95% identity to BDLO04 (SEQ ID NO: 5).

In one embodiment of the polynucleotides described above, the first nucleotide sequence encoding the heavy chain of the Factor VIII polypeptide has at least 96% identity to the respective heavy chain sequence (e.g., CS04-HC-NA (SEQ ID NO: 3)), and the second nucleotide sequence encoding the light chain of the Factor FVIII polypeptide has at least 96% identity to the respective light chain sequence (e.g., CS04-LC-NA (SEQ ID NO: 4)).

In one embodiment of the polynucleotides described above, the first nucleotide sequence encoding the heavy chain of the Factor VIII polypeptide has at least 97% identity to the respective heavy chain sequence (e.g., CS04-HC-NA (SEQ ID NO: 3)), and the second nucleotide sequence encoding the light chain of the Factor FVIII polypeptide has at least 97% identity to the respective light chain sequence (e.g., CS04-LC-NA (SEQ ID NO: 4)).

In one embodiment of the polynucleotides described above, the first nucleotide sequence encoding the heavy chain of the Factor VIII polypeptide has at least 98% identity to the respective heavy chain sequence (e.g., CS04-HC-NA (SEQ ID NO: 3)), and the second nucleotide sequence encoding the light chain of the Factor FVIII polypeptide has at least 98% identity to the respective light chain sequence (e.g., CS04-LC-NA (SEQ ID NO: 4)).

In one embodiment of the polynucleotides described above, the first nucleotide sequence encoding the heavy chain of the Factor VIII polypeptide has at least 99% identity to the respective heavy chain sequence (e.g., CS04-HC-NA (SEQ ID NO: 3)), and the second nucleotide sequence encoding the light chain of the Factor FVIII polypeptide has at least 99% identity to the respective light chain sequence (e.g., CS04-LC-NA (SEQ ID NO: 4)).

In one embodiment of the polynucleotides described above, the first nucleotide sequence encoding the heavy chain of the Factor VIII polypeptide has at least 99.5% identity to the respective heavy chain sequence (e.g., CS04-HC-NA (SEQ ID NO: 3)), and the second nucleotide sequence encoding the light chain of the Factor FVIII polypeptide has at least 99.5% identity to the respective light chain sequence (e.g., CS04-LC-NA (SEQ ID NO: 4)).

In one embodiment of the polynucleotides described above, the first nucleotide sequence encoding the heavy chain of the Factor VIII polypeptide has at least 99.9% identity to the respective heavy chain sequence (e.g., CS04-HC-NA (SEQ ID NO: 3)), and the second nucleotide sequence encoding the light chain of the Factor FVIII polypeptide has at least 99.9% identity to the respective light chain sequence (e.g., CS04-LC-NA (SEQ ID NO: 4)).

In one embodiment of the polynucleotides described above, the first nucleotide sequence encoding the heavy chain of the Factor VIII polypeptide is CS04-HC-NA (SEQ ID NO: 3), and the second nucleotide sequence encoding the light chain of the Factor FVIII polypeptide is CS04-LC-NA (SEQ ID NO: 4).

In one aspect, the disclosure provides a polynucleotide comprising a nucleotide sequence having at least 95% identity to CS04-FL-NA, wherein the polynucleotide encodes a Factor VIII polypeptide.

In one embodiment of the polynucleotides described above, the nucleotide sequence has at least 96% identity to the respective full-length polynucleotide sequence (e.g., CS04-FL-NA (SEQ ID NO: 1)).

In one embodiment of the polynucleotides described above, the nucleotide sequence has at least 97% identity to the respective full-length polynucleotide sequence (e.g., CS04-FL-NA (SEQ ID NO: 1)).

In one embodiment of the polynucleotides described above, the nucleotide sequence has at least 98% identity to the respective full-length polynucleotide sequence (e.g., CS04-FL-NA (SEQ ID NO: 1)).

In one embodiment of the polynucleotides described above, the nucleotide sequence has at least 99% identity to the respective full-length polynucleotide sequence (e.g., CS04-FL-NA (SEQ ID NO: 1)).

In one embodiment of the polynucleotides described above, the nucleotide sequence has at least 99.5% identity to the respective full-length polynucleotide sequence (e.g., CS04-FL-NA (SEQ ID NO: 1)).

In one embodiment of the polynucleotides described above, the nucleotide sequence has at least 99.9% identity to the respective full-length polynucleotide sequence (e.g., CS04-FL-NA (SEQ ID NO: 1)).

In one embodiment of the polynucleotides described above, the nucleotide sequence is CS04-FL-NA (SEQ ID NO: 1).

In one embodiment of the polynucleotides described above, the polynucleotide encodes a Factor VIII polypeptide comprising an amino acid sequence having at least 95% identity to CS04-FL-AA (SEQ ID NO: 2).

In one embodiment of the polynucleotides described above, the polynucleotide encodes a Factor VIII polypeptide comprising an amino acid sequence having at least 96% identity to CS04-FL-AA (SEQ ID NO: 2).

In one embodiment of the polynucleotides described above, the polynucleotide encodes a Factor VIII polypeptide comprising an amino acid sequence having at least 97% identity to CS04-FL-AA (SEQ ID NO: 2).

In one embodiment of the polynucleotides described above, the polynucleotide encodes a Factor VIII polypeptide comprising an amino acid sequence having at least 98% identity to CS04-FL-AA (SEQ ID NO: 2).

In one embodiment of the polynucleotides described above, the polynucleotide encodes a Factor VIII polypeptide comprising an amino acid sequence having at least 99% identity to CS04-FL-AA (SEQ ID NO: 2).

In one embodiment of the polynucleotides described above, the polynucleotide encodes a Factor VIII polypeptide comprising an amino acid sequence having at least 99.5% identity to CS04-FL-AA (SEQ ID NO: 2).

In one embodiment of the polynucleotides described above, the polynucleotide encodes a Factor VIII polypeptide comprising an amino acid sequence having at least 99.9% identity to CS04-FL-AA (SEQ ID NO: 2).

In one embodiment of the polynucleotides described above, the polynucleotide encodes a Factor VIII polypeptide comprising the amino acid sequence of CS04-FL-AA (SEQ ID NO: 2).

In one embodiment of the polynucleotides described above, the nucleotide sequence has at least 95% identity to a sequence selected from the group consisting of CS04-FL-NA, CS04-HC-NA, and CS04-LC-NA.

In one embodiment of the polynucleotides described above, the nucleotide sequence has at least 96% identity to a sequence selected from the group consisting of CS04-FL-NA, CS04-HC-NA, and CS04-LC-NA.

In one embodiment of the polynucleotides described above, the nucleotide sequence has at least 97% identity to a sequence selected from the group consisting of CS04-FL-NA, CS04-HC-NA, and CS04-LC-NA.

In one embodiment of the polynucleotides described above, the nucleotide sequence has at least 98% identity to a sequence selected from the group consisting of CS04-FL-NA, CS04-HC-NA, and CS04-LC-NA.

In one embodiment of the polynucleotides described above, the nucleotide sequence has at least 99% identity to a sequence selected from the group consisting of CS04-FL-NA, CS04-HC-NA, and CS04-LC-NA.

In one embodiment of the polynucleotides described above, the nucleotide sequence has at least 99.5% identity to a sequence selected from the group consisting of CS04-FL-NA, CS04-HC-NA, and CS04-LC-NA.

In one embodiment of the polynucleotides described above, the nucleotide sequence has at least 99.5% identity to a sequence selected from the group consisting of CS04-FL-NA, CS04-HC-NA, and CS04-LC-NA.

In one embodiment of the polynucleotides described above, the nucleotide sequence is selected from the group consisting of CS04-FL-NA, CS04-HC-NA, and CS04-LC-NA.

In one embodiment of the polynucleotides described above, the polynucleotide also includes a promoter element operably linked to the polynucleotide encoding the Factor VIII polypeptide.

In one embodiment of the polynucleotides described above, the polynucleotide also includes an enhancer element operably linked to the polynucleotide encoding the Factor VIII polypeptide.

In one embodiment of the polynucleotides described above, the polynucleotide also includes a polyadenylation element operably linked to the polynucleotide encoding the Factor VIII polypeptide.

In one embodiment of the polynucleotides described above, the polynucleotide also includes an intron operatively linked to the nucleotide sequence encoding the Factor VIII polypeptide.

In one embodiment of the polynucleotides described above, the intron is positioned between a promoter element and the translation initiation site (e.g., the first coding ATG) of the nucleotide sequence encoding a Factor VIII polypeptide.

In another aspect, the disclosure provides a mammalian gene therapy vector including a polynucleotide as described above.

In one embodiment of the mammalian gene therapy vector described above, the mammalian gene therapy vector is an adeno-associated virus (AAV) vector.

In one embodiment of the mammalian gene therapy vector described above, the AAV vector is an AAV-8 vector.

In another aspect, the disclosure provides a method for treating hemophilia A including administering, to a patient in need thereof, a mammalian gene therapy vector as described above.

In another aspect, the disclosure provides a mammalian gene therapy vector as described above for treating hemophilia A.

In another aspect, the disclosure provides the use of a mammalian gene therapy vector as described above for the manufacture of a medicament for treating hemophilia A.

BRIEF DESCRIPTION OF DRAWINGS

FIGS. 2A and 2B show the CS04 codon-altered nucleotide sequence (SEQ ID NO: 1) encoding a Factor VIII variant in accordance with some embodiments ("CS04-FL-NA" for full-length coding sequence).

FIG. 3 shows the Factor VIII variant amino acid sequence (SEQ ID NO: 2) encoded by the CS04 codon-altered nucleotide sequence in accordance with some embodiments ("CS04-FL-AA" for full-length amino acid sequence).

FIG. 4 shows the portion of the CS04 codon-altered nucleotide sequence (SEQ ID NO: 3) encoding the heavy chain of a Factor VIII variant in accordance with some embodiments ("CS04-HC-NA").

FIG. 5 shows the portion of the CS04 codon-altered nucleotide sequence (SEQ ID NO: 4) encoding the light chain of a Factor VIII variant in accordance with some embodiments ("CS04-LC-NA").

FIG. 6 shows an exemplary coding sequence (SEQ ID NO: 5) for a B-domain substituted linker in accordance with some embodiments. BDLO04 (SEQ ID NO: 5) is the respective portion of the CS04 codon-altered nucleotide sequence that encodes a B-domain substituted linker.

FIGS. 7A, 7B, and 7C show an AAV vector sequence (SEQ ID NO: 6) containing an CS04 codon-altered nucleotide sequence in accordance with some embodiments ("CS04-AV-NA").

FIGS. 8A and 8B show the CS08 codon-altered nucleotide sequence (SEQ ID NO: 7) encoding a Factor VIII variant in accordance with some embodiments ("CS08-FL-NA").

FIGS. 9A and 9B show the CS10 codon-altered nucleotide sequence (SEQ ID NO: 8) encoding a Factor VIII variant in accordance with some embodiments ("CS10-FL-NA").

FIGS. 10A and 10B show the CS11 codon-altered nucleotide sequence (SEQ ID NO: 9) encoding a Factor VIII variant in accordance with some embodiments ("CS11-FL-NA").

FIGS. 11A and 11B show the CS40 wild-type ReFacto coding sequence (SEQ ID NO: 10), in accordance with some embodiments ("CS40-FL-NA").

FIGS. 12A and 12B show the CH25 codon-altered nucleotide sequence (SEQ ID NO: 11) encoding a Factor VIII variant in accordance with some embodiments ("CH25-FL-NA").

FIG. 13 shows a wild-type human Factor VIII amino acid sequence (SEQ ID NO: 12), in accordance with some embodiments ("FVIII-FL-AA").

Figure 1:
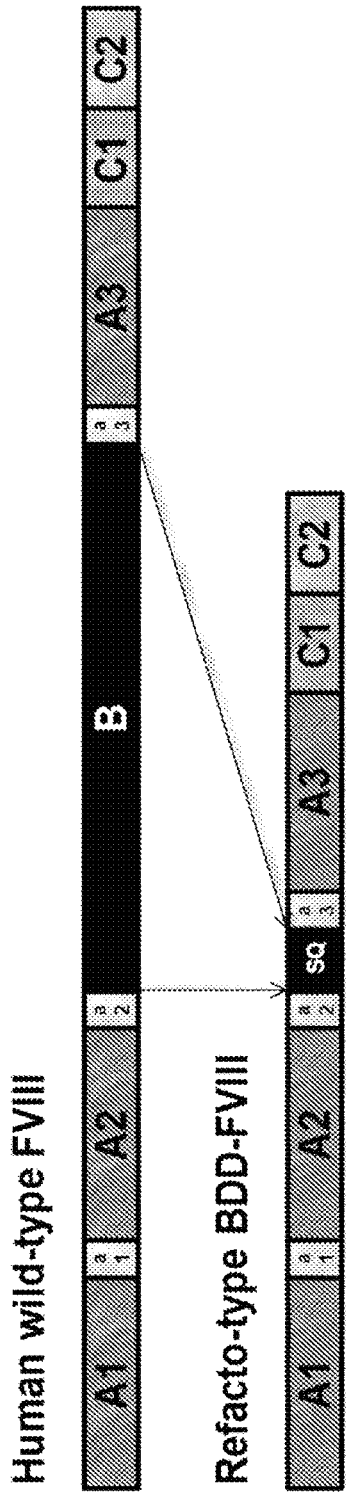
FIG. 1 shows schematic illustrations of the wild-type and ReFacto-type human Factor VIII protein constructs.

FIG. 15 shows the integrity of AAV vector genome preparations, as analyzed by agarose gel electrophoresis. Lane 1, DNA marker; lane 2, vCS40; lane 4, vCS04. The AAV vectors have all the same-sized genomes, migrating at approximately 5 kb (arrow, right side). The scale on the left side indicates size of the DNA fragments in kilobases (kb).

FIG. 16 shows the protein analysis of AAV vector preparations by PAGE and silver staining. Lane 1, protein marker (M); lane 2, vCS40; and lane 4, vCS04. The constructs all have the same AAV8 capsids consisting of VP1, VP2, and VP3 (arrows right side). The scale on the left side indicates size of the protein marker in kilodaltons (kDa).

FIG. 17 shows FVIII activity following systemic administration of a (r)AAV8-based gene therapy vector containing the CS04 Factor VIII codon optimized construct, as described in Example 3. cp, vector capsid particles; FVIII, factor VIII; LLOQ, lower limit of quantification. 14, 28, 42, and 56-day time points are shown left to right in the graph.

FIG. 18 shows reduced blood loss, in a tail-tip bleeding assay, after systemic administration of a (r)AAV8-based gene therapy vector containing the CS04 Factor VIII codon optimized construct, as described in Example 3. cp, vector capsid particles.

FIGS. 19A, 19B, and 19C show biodistribution of the (r)AAV8-based gene therapy vector containing the CS04 Factor VIII codon optimized construct DNA after systemic administration. 1902=liver; 1904=lymph node; 1906=skeletal muscle; 1908=heart; 1910=kidney; 1912=spleen; 1914=lung; 1916=testis; 1918=brain.

DETAILED DESCRIPTION OF DISCLOSURE

I. INTRODUCTION

AAV-based gene therapy holds great promise for the treatment of hemophiliacs. For hemophilia B, first clinical data are encouraging in that FIX levels of about 10% can be maintained in at least some patients for more than 1 year. For hemophilia A however, achieving therapeutic expression levels of 5-10% with AAV vectors remains challenging for various reasons. First, the Factor VIII coding sequence is too large for conventional AAV-based vectors. Second, engineered B-domain deleted or truncated Factor VIII constructs suffer from poor expression in vivo, even when codon-optimized. Third, these B-domain deleted or truncated Factor VIII variant constructs have short half-lives in vivo, exacerbating the effects of poor expression. Fourth, even when expressed, FVIII is not efficiently secreted from cells, as are other coagulation factors, such as Factor IX. Therefore, strategies to improve the expression of FVIII are needed to make FVIII gene therapy a viable therapeutic option for hemophilia A patients.

The present disclosure relates to the discovery of codon-altered Factor VIII variant coding sequences that solve these and other problems associated with Factor VIII gene therapy. For example, the polynucleotides disclosed herein provide markedly improved expression in mammalian cells, and display improved virion packaging due to stabilized packing interactions. In some implementations, these advantages are realized by using coding sequences for the heavy and light chains of Factor VIII with high sequence identity to the codon altered CS04 construct (e.g., with high sequence identity to the CS04-HC heavy chain coding sequence and high sequence identity to the CS04-LC light chain coding sequence).

In some implementations, the Factor VIII molecules encoded by the polynucleotides described herein have been shortened by truncating, deleting, or replacing the wild-type B-domain. As such, the polynucleotides are better suited for expressing Factor VIII via conventional gene therapy vectors, which inefficiently express larger polypeptides, such as the wild-type Factor VIII.

Advantageously, it is shown herein that the CS04 codon-altered Factor VIII variant coding sequence provide superior expression of a B-domain deleted Factor VIII construct in vivo. For example, it is demonstrated in Example 2 and Table 4 that intravenous administration of AAV-based gene therapy vectors having the CS04 (SEQ ID NO: 1) coding sequence provides a 74-fold increase in Factor VIII expression, relative to the corresponding CS40 construct encoded with the wild-type polynucleotide sequence (SEQ ID NO: 10), in Factor VIII knock-out mice (Table 4).

Further, it also shown herein that the CS04 codon-altered Factor VIII variant coding sequence provides superior virion packaging and virus production. For example, it is demonstrated in Example 1 that AAV vector constructs containing the CS04 construct provided 5 to 7-fold greater viral yield, relative to the corresponding CS40 construct encoded with the wild-type polynucleotide sequence, when isolated from the same amount of cell pellet.

II. DEFINITIONS

As used herein, the following terms have the meanings ascribed to them unless specified otherwise.

As used herein, the terms "Factor VIII" and "FVIII" are used interchangeably, and refer to any protein with Factor VIII activity (e.g., active FVIII, often referred to as FVIIIa) or protein precursor (e.g., pro-protein or pre-pro-protein) of a protein with Factor VIII activity, particularly Factor IXa cofactor activity. In an exemplary embodiment, a Factor VIII polypeptide refers to a polypeptide that has sequences with high sequence identity (e.g., at least 70%, 75%, 80%, 85%, 90%, 95%, 99%, or more) to the heavy and light chains of a wild type Factor VIII polypeptide. In some embodiments, the B-domain of a Factor VIII polypeptide is deleted, truncated, or replaced with a linker polypeptide to reduce the size of the polynucleotide encoding the Factor VIII polypeptide. In an exemplary embodiment, amino acids 20-1457 of CS04-FL-AA constitute a Factor VIII polypeptide.

Non-limiting examples of wild type Factor VIII polypeptides include human pre-pro-Factor VIII (e.g., GenBank accession nos. AAA52485, CAA25619, AAA58466, AAA52484, AAA52420, AAV85964, BAF82636, BAG36452, CAI41660, CAI41666, CAI41672, CAI43241, CA003404, EAW72645, AAH22513, AAH64380, AAH98389, AAI11968, AAI11970, or AAB61261), corresponding pro-Factor VIII, and natural variants thereof; porcine pre-pro-Factor VIII (e.g., UniProt accession nos. F1RZ36 or K7GSZ5), corresponding pro-Factor VIII, and natural variants thereof; mouse pre-pro-Factor VIII (e.g., GenBank accession nos. AAA37385, CAM15581, CAM26492, or EDL29229), corresponding pro-Factor VIII, and natural variants thereof; rat pre-pro-Factor VIII (e.g., GenBank accession no. AAQ21580), corresponding pro-Factor VIII, and natural variants thereof; rat pre-pro-Factor VIII; and other mammalian Factor VIII homologues (e.g., monkey, ape, hamster, guinea pig, etc.).

As used herein, a Factor VIII polypeptide includes natural variants and artificial constructs with Factor IX cofactor activity. As used in the present disclosure, Factor VIII encompasses any natural variants, alternative sequences, isoforms, or mutant proteins that retain some basal Factor IX cofactor activity (e.g., at least 5%, 10%, 25%, 50%, 75%, or more of the corresponding wild type activity). Examples of Factor VIII amino acid variations (relative to FVIII-FL-AA (SEQ ID NO: 12)) found in the human population include, without limitation, S19R, R22T, Y24C, Y25C, L26P/R, E30V, W33G, Y35C/H, G41C, R48C/K, K67E/N, L69P, E72K, D75E/V/Y, P83R, G89D/V, G92A/V, A97P, E98K, V99D, D101G/H/V, V104D, K108T, M110V, A111T/V, H113R/Y, L117F/R, G121S, E129V, G130R, E132D, Y133C, D135G/Y, T137A/I, S138R, E141K, D145H, V147D, Y155H, V159A, N163K, G164D/V, P165S, C172W, S176P, S179P, V181E/M, K185T, D186G/N/Y, S189L, L191F, G193R, L195P, C198G, S202N/R, F214V, L217H, A219D/T, V220G, D222V, E223K, G224W, T252I, V253F, N254I, G255V, L261P, P262L, G263S, G266F, C267Y, W274C, H275L, G278R, G280D, E284K, V285G, E291G/K, T294I, F295L, V297A, N299I, R301C/H/L, A303E/P, I307S, S308L, F312S, T314A/I, A315V, G323E, L326P, L327P/V, C329F, I331V, M339T, E340K, V345A/L, C348R/S/Y, Y365C, R391C/H/P, S392L/P, A394S, W401G, I405F/S, E409G, W412G/R, K427I, L431F/S, R437P/W, I438F, G439D/S/V, Y442C, K444R, Y450D/N, T454I, F455C, G466E, P470L/R/T, G474E/R/V, E475K, G477V, D478N, T479R, F484C, A488G, R490G, Y492C/H, Y492H, I494T, P496R, G498R, R503H, G513S/V, I522Y, K529E, W532G, P540T, T541S, D544N, R546W, R550C/G/H, S553P, S554C/G, V556D, R560T, D561G/H/Y, I567T, P569R, S577F, V578A, D579A/H, N583S, Q584H/K/R, I585R/T, M586V, D588G/Y, L594Q, S596P, N601D/K, R602G, S603I/R, W604C, Y605H/S, N609I, R612C, N631K/S, M633I, S635N,N637D/I/S, Y639C, L644V, L650F, V653A/M, L659P, A663V, Q664P, F677L, M681I, V682F, Y683C/N, T686R, F698L, M699T/V, M701I, G705V, G710W, N713I, R717L/W, G720D/S, M721I/L, A723T, L725Q, V727F, E739K, Y742C, R795G, P947R, V1012L, E1057K, H1066Y, D1260E, K1289Q, Q1336K, N1460K, L1481P, A1610S, I1698T, Y1699C/F, E1701K, Q1705H, R1708C/H, T1714S, R1715G, A1720V, E1723K, D1727V, Y1728C, R1740G, K1751Q, F1762L, R1768H, G1769R, L1771P, L1775F/V, L1777P, G1779E/R, P1780L, I1782R, D1788H, M1791T, A1798P, S1799H, R1800C/G/H, P1801A, Y1802C, S1803Y, F1804S, L1808F, M1842I, P1844S, T1845P, E1848G, A1853T/V, S1858C, K1864E, D1865N/Y, H1867P/R, G1869D/V, G1872E, P1873R, L1875P, V1876L, C1877R/Y, L1882P, R1888I, E1894G, I1901F, E1904D/K, S1907C/R, W1908L, Y1909C, A1939T/V, N1941D/S, G1942A, M1945V, L1951F, R1960L/Q, L1963P, S1965I, M1966I/V, G1967D, S1968R, N1971T, H1973L, G1979V, H1980P/Y, F1982I, R1985Q, L1994P, Y1998C, G2000A, T2004R, M2007I, G2013R, W2015C, R2016P/W, E2018G, G2022D, G2028R, S2030N, V2035A, Y2036C, N2038S, 2040Y, G2045E/V, I2051S, I2056N, A2058P, W2065R, P2067L, A2070V, S2082N, S2088F, D2093G/Y, H2101D, T2105N, Q2106E/P/R, G2107S, R2109C, I2117F/S, Q2119R, F2120C/L, Y2124C, R2135P, S2138Y, T2141N, M2143V, F2145C, N2148S, N2157D, P2162L, R2169C/H, P2172L/Q/R, T2173A/I, H2174D, R2178C/H/L, R2182C/H/P, M2183R/V, L2185S/W, S2192I, C2193G, P2196R, G2198V, E2200D, I2204T, I2209N, A2211P, A2220P, P2224L, R2228G/L/P/Q, L2229F, V2242M, W2248C/S, V2251A/E, M2257V, T2264A, Q2265R, F2279C/I, I2281T, D2286G, W2290L, G2304V, D2307A, P2319L/S, R2323C/G/H/L, R2326G/L/P/Q, Q2330P, W2332R, I2336F, R2339T, G2344C/D/S, and C2345S/Y. Factor VIII proteins also include polypeptides containing post-translational modifications.

Generally, polynucleotides encoding Factor VIII encode for an inactive single-chain polypeptide (e.g., a pre-pro-protein) that undergoes post-translational processing to form an active Factor VIII protein (e.g., FVIIIa). For example, referring to FIG. 1, the wild type human Factor VIII pre-pro-protein is first cleaved to release the encoded signal peptide (not shown), forming a first single-chain pro-protein (shown as "human wild-type FVIII"). The pro-protein is then cleaved between the B and A3 domains to form a first polypeptide that includes the Factor VIII heavy chain (e.g., the A1 and A2 domains) and B-domain, and a second polypeptide that includes the Factor VIII light chain (e.g., including the A3, C1, and C3 domains). The first polypeptide is further cleaved to remove the B-domain, and also to separate the A1 and A2 domains, which remain associated with the Factor VIII light chain in the mature Factor VIIIa protein. For review of the Factor VIII maturation process, see Graw et al., Nat Rev Genet., 6(6):488-501 (2005), the content of which is incorporated herein by reference in its entirety for all purposes.

However, in some embodiments, the Factor VIII polypeptide is a single-chain Factor VIII polypeptide. Single-chain Factor VIII polypeptides are engineered to remove natural cleavage sites, and optionally remove, truncate, or replace the B-domain of Factor VIII. As such, they are not matured by cleavage (other than cleavage of an optional signal and/or leader peptide), and are active as a single chain. Non-limiting examples of single-chain Factor VIII polypeptides are described in Zollner et al. (Thromb Res, 134(1):125-31 (2014)) and Donath et al. (Biochem J., 312 (1):49-55 (1995)), the disclosures of which are hereby incorporated by reference in their entireties for all purposes.

As used herein, the terms "Factor VIII heavy chain," or simply "heavy chain," refers to the aggregate of the A1 and A2 domains of a Factor VIII polypeptide. In an exemplary embodiment, amino acids 20-759 of CS04-FL-AA (SEQ ID NO: 2) constitute a Factor VIII heavy chain.

As used herein, the term "Factor VIII light chain," or simply "light chain," refers to the aggregate of the A3, C1, and C2 domains of a Factor VIII polypeptide. In an exemplary embodiment, amino acids 774-1457 CS04-FL-AA (SEQ ID NO: 2) constitute a Factor VIII light chain. In some embodiments, a Factor VIII light chain excludes the acidic a3 peptide, which is released during maturation in vivo.

Generally, Factor VIII heavy and light chains are expressed as a single polypeptide chain, e.g., along with an optional B-domain or B-domain substituted linker. However, in some embodiments, a Factor VIII heavy chain and Factor VIII light chain are expressed as separate polypeptide chains (e.g., co-expressed), and reconstituted to form a Factor VIII protein (e.g., in vivo or in vitro).

As used herein, the terms "B-domain substituted linker" and "Factor VIII linker" are used interchangeably, and refer to truncated versions of a wild type Factor VIII B-domain (e.g., amino acids 760-1667 of FVIII-FL-AA (SEQ ID NO: 12)) or peptides engineered to replace the B-domain of a Factor VIII polypeptide. As used herein, a Factor VIII linker is positioned between the C-terminus of a Factor VIII heavy chain and the N-terminus of a Factor VIII light chain in a Factor VIII variant polypeptide in accordance with some embodiments. Non-limiting examples of B-domain substituted linkers are disclosed in U.S. Pat. Nos. 4,868,112, 5,112,950, 5,171,844, 5,543,502, 5,595,886, 5,610,278, 5,789,203, 5,972,885, 6,048,720, 6,060,447, 6,114,148, 6,228,620, 6,316,226, 6,346,513, 6,458,563, 6,924,365, 7,041,635, and 7,943,374; U.S. Patent Application Publication Nos. 2013/024960, 2015/0071883, and 2015/0158930; and PCT Publication Nos. WO 2014/064277 and WO 2014/127215, the disclosures of which are hereby incorporated by reference, in their entireties, for all purposes.

Unless otherwise specified herein, the numbering of Factor VIII amino acids refers to the corresponding amino acid in the full-length, wild-type human Factor VIII sequence (FVIII-FL-AA), presented as SEQ ID NO: 12 in FIG. 13. As such, when referring to an amino acid substitution in a Factor VIII variant protein disclosed herein, the recited amino acid number refers to the analogous (e.g., structurally or functionally equivalent) and/or homologous (e.g., evolutionarily conserved in the primary amino acid sequence) amino acid in the full-length, wild-type Factor VIII sequence. For example, a T2105N amino acid substitution refers to a T to N substitution at position 2105 of the full-length, wild-type human Factor VIII sequence (FVIII-FL-AA; SEQ ID NO: 12) and a T to N substitution at position 1211 of the Factor VIII variant protein encoded by CS04 (CS04-FL-AA; SEQ ID NO: 2).

As described herein, the Factor VIII amino acid numbering system is dependent on whether the Factor VIII signal peptide (e.g., amino acids 1-19 of the full-length, wild-type human Factor VIII sequence) is included. Where the signal peptide is included, the numbering is referred to as "signal peptide inclusive" or "SPI". Where the signal peptide is not included, the numbering is referred to as "signal peptide exclusive" or "SPE." For example, F328S is SPI numbering for the same amino acid as F309S, in SPE numbering. Unless otherwise indicated, all amino acid numbering refers to the corresponding amino acid in the full-length, wild-type human Factor VIII sequence (FVIII-FL-AA), presented as SEQ ID NO: 12 in FIG. 13.

As described herein, the codon-altered polynucleotides provide increased expression of transgenic Factor VIII in vivo (e.g., when administered as part of a gene therapy vector), as compared to the level of Factor VIII expression provided by a natively-coded Factor VIII construct (e.g., a polynucleotide encoding the same Factor VIII construct using the wild-type human codons). As used herein, the term "increased expression" refers to an increased level of transgenic Factor VIII activity in the blood of an animal administered the codon-altered polynucleotide encoding Factor VIII, as compared to the level of transgenic Factor VIII activity in the blood of an animal administered a natively-coded Factor VIII construct. The activity levels can be measured using any Factor VIII activity known in the art. An exemplary assay for determining Factor VIII activity is the Technochrome FVIII assay (Technoclone, Vienna, Austria).

In some embodiments, increased expression refers to at least 25% greater transgenic Factor VIII activity in the blood of an animal administered the codon-altered Factor VIII polynucleotide, as compared to the level of transgenic Factor VIII activity in the blood of an animal administered a natively coded Factor VIII polynucleotide. In some embodiments, increased expression refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, at least 20-fold greater, at least 25-fold greater, at least 30-fold greater, at least 40-fold greater, at least 50-fold greater, at least 60-fold greater, at least 70-fold greater, at least 80-fold greater, at least 90-fold greater, at least 100-fold greater, at least 125-fold greater, at least 150-fold greater, at least 175-fold greater, at least 200-fold greater, at least 225-fold greater, or at least 250-fold greater transgenic Factor VIII activity in the blood of an animal administered the codon-altered Factor VIII polynucleotide, as compared to the level of transgenic Factor VIII activity in the blood of an animal administered a natively coded Factor VIII polynucleotide.

As described herein, the codon-altered polynucleotides provide increased vector production, as compared to the level of vector production provided by a natively-coded Factor VIII construct (e.g., a polynucleotide encoding the same Factor VIII construct using the wild-type human codons). As used herein, the term "increased virus production" refers to an increased vector yield in cell culture (e.g., titer per liter culture) inoculated with the codon-altered polynucleotide encoding Factor VIII, as compared to the vector yield in cell culture inoculated with a natively-coded Factor VIII construct. The vector yields can be measured using any vector titer assay known in the art. An exemplary assay for determining vector yield (e.g., of an AAV vector) is qPCR targeting the AAV2 inverted terminal repeats (Aurnhammer, Human Gene Therapy Methods: Part B 23:18-28 (2012)).

In some embodiments, increased virus production refers to at least 25% greater codon-altered vector yield, as compared to the yield of a natively-coded Factor VIII construct in the same type of culture. In some embodiments, increased vector production refers to at least 50% greater, at least 75% greater, at least 100% greater, at least 3-fold greater, at least 4-fold greater, at least 5-fold greater, at least 6-fold greater, at least 7-fold greater, at least 8-fold greater, at least 9-fold greater, at least 10-fold greater, at least 15-fold greater, or at least 20-fold greater codon-altered vector yield, as compared to the yield of a natively-coded Factor VIII construct in the same type of culture.

As used herein, the term "hemophilia" refers to a group of disease states broadly characterized by reduced blood clotting or coagulation. Hemophilia may refer to Type A, Type B, or Type C hemophilia, or to the composite of all three diseases types. Type A hemophilia (hemophilia A) is caused by a reduction or loss of factor VIII (FVIII) activity and is the most prominent of the hemophilia subtypes. Type B hemophilia (hemophilia B) results from the loss or reduction of factor IX (FIX) clotting function. Type C hemophilia (hemophilia C) is a consequence of the loss or reduction in factor XI (FXI) clotting activity. Hemophilia A and B are X-linked diseases, while hemophilia C is autosomal. Conventional treatments for hemophilia include both prophylactic and on-demand administration of clotting factors, such as FVIII, FIX, including Bebulin®-VH, and FXI, as well as FEIBA-VH, desmopressin, and plasma infusions.

As used herein, the term "FVIII gene therapy" includes any therapeutic approach of providing a nucleic acid encoding Factor VIII to a patient to relieve, diminish, or prevent the reoccurrence of one or more symptoms (e.g., clinical factors) associated with hemophilia. The term encompasses administering any compound, drug, procedure, or regimen comprising a nucleic acid encoding a Factor VIII molecule, including any modified form of Factor VIII (e.g., Factor VIII variant), for maintaining or improving the health of an individual with hemophilia. One skilled in the art will appreciate that either the course of FVIII therapy or the dose of a FVIII therapeutic agent can be changed, e.g., based upon the results obtained in accordance with the present disclosure.

As used herein, the term "bypass therapy" includes any therapeutic approach of providing non-Factor VIII hemostatic agents, compounds or coagulation factors to a patient to relieve, diminish, or prevent the reoccurrence of one or more symptoms (e.g., clinical factors) associated with hemophilia. Non-Factor VIII compounds and coagulation factors include, but are not limited to, Factor VIII Inhibitor Bypass Activity (FEIBA), recombinant activated factor VII (FVIIa), prothrombin complex concentrates, and activated prothrombin complex concentrates. These non-Factor VIII compounds and coagulation factors may be recombinant or plasma-derived. One skilled in the art will appreciate that either the course of bypass therapy or the dose of bypass therapy can be changed, e.g., based upon the results obtained in accordance with the present disclosure.

As used herein, a "combination therapy" including administration of a nucleic acid encoding a Factor VIII molecule and a conventional hemophilia A therapeutic agent includes any therapeutic approach of providing both a nucleic acid encoding a Factor VIII molecule and a Factor VIII molecule and/or non-Factor VIII hemostatic agent (e.g., bypass therapeutic agent) to a patient to relieve, diminish, or prevent the reoccurrence of one or more symptoms (e.g., clinical factors) associated with hemophilia. The term encompasses administering any compound, drug, procedure, or regimen including a nucleic acid encoding a Factor VIII molecule, including any modified form of factor VIII, which is useful for maintaining or improving the health of an individual with hemophilia and includes any of the therapeutic agents described herein.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy*, 20th Edition, 2003, Gennaro, Ed., Lippincott, Williams & Wilkins).

As used herein, the term "gene" refers to the segment of a DNA molecule that codes for a polypeptide chain (e.g., the coding region). In some embodiments, a gene is positioned by regions immediately preceding, following, and/or intervening the coding region that are involved in producing the polypeptide chain (e.g., regulatory elements such as a promoter, enhancer, polyadenylation sequence, 5'-untranslated region, 3'-untranslated region, or intron).

As used herein, the term "regulatory elements" refers to nucleotide sequences, such as promoters, enhancers, terminators, polyadenylation sequences, introns, etc, that provide for the expression of a coding sequence in a cell.

As used herein, the term "promoter element" refers to a nucleotide sequence that assists with controlling expression of a coding sequence. Generally, promoter elements are located 5' of the translation start site of a gene. However, in certain embodiments, a promoter element may be located within an intron sequence, or 3' of the coding sequence. In some embodiments, a promoter useful for a gene therapy vector is derived from the native gene of the target protein (e.g., a Factor VIII promoter). In some embodiments, a promoter useful for a gene therapy vector is specific for expression in a particular cell or tissue of the target organism (e.g., a liver-specific promoter). In yet other embodiments, one of a plurality of well characterized promoter elements is used in a gene therapy vector described herein. Non-limiting examples of well-characterized promoter elements include the CMV early promoter, the β-actin promoter, and the methyl CpG binding protein 2 (MeCP2) promoter. In some embodiments, the promoter is a constitutive promoter, which drives substantially constant expression of the target protein. In other embodiments, the promoter is an inducible promoter, which drives expression of the target protein in response to a particular stimulus (e.g., exposure to a particular treatment or agent). For a review of designing promoters for AAV-mediated gene therapy, see Gray et al. (Human Gene Therapy 22:1143-53 (2011)), the contents of which are expressly incorporated by reference in their entirety for all purposes.

As used herein, the term "vector" refers to any vehicle used to transfer a nucleic acid (e.g., encoding a Factor VIII gene therapy construct) into a host cell. In some embodiments, a vector includes a replicon, which functions to replicate the vehicle, along with the target nucleic acid. Non-limiting examples of vectors useful for gene therapy include plasmids, phages, cosmids, artificial chromosomes, and viruses, which function as autonomous units of replication in vivo. In some embodiments, a vector is a viral vehicle for introducing a target nucleic acid (e.g., a codon-altered polynucleotide encoding a Factor VIII variant). Many modified eukaryotic viruses useful for gene therapy are known in the art. For example, adeno-associated viruses (AAVs) are particularly well suited for use in human gene therapy because humans are a natural host for the virus, the native viruses are not known to contribute to any diseases, and the viruses illicit a mild immune response.

As used herein, the term "CpG island" refers to a region within a polynucleotide having a statistically elevated density of CpG dinucleotides. As used herein, a region of a polynucleotide (e.g., a polynucleotide encoding a codon-altered Factor VIII protein) is a CpG island if, over a 200-base pair window: (i) the region has GC content of greater than 50%, and (ii) the ratio of observed CpG dinucleotides per expected CpG dinucleotides is at least 0.6, as defined by the relationship:

$$\frac{N[CpG] * N[\text{length of window}]}{N[C] * N[G]} \geq 0.6.$$

For additional information on methods for identifying CpG islands, see Gardiner-Garden M. et al., J Mol Biol., 196(2):261-82 (1987), the content of which is expressly incorporated herein by reference, in its entirety, for all purposes.

As used herein, the term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

The term "amino acid" refers to naturally occurring and non-natural amino acids, including amino acid analogs and amino acid mimetics that function in a manner similar to the naturally occurring amino acids. Naturally occurring amino acids include those encoded by the genetic code, as well as those amino acids that are later modified, e.g., hydroxyproline, y-carboxyglutamate, and O-phosphoserine. Naturally occurring amino acids can include, e.g., D- and L-amino acids. The amino acids used herein can also include non-natural amino acids. Amino acid analogs refer to compounds that have the same basic chemical structure as a naturally occurring amino acid, i.e., any carbon that is bound to a hydrogen, a carboxyl group, an amino group, and an R group, e.g., homoserine, norleucine, methionine sulfoxide, or methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of ordinary skill in the art will recognize that individual substitutions, deletions or additions to a nucleic acid or peptide sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

Conservative amino acid substitutions providing functionally similar amino acids are well known in the art. Dependent on the functionality of the particular amino acid, e.g., catalytic, structural, or sterically important amino acids, different groupings of amino acid may be considered conservative substitutions for each other. Table 1 provides groupings of amino acids that are considered conservative substitutions based on the charge and polarity of the amino acid, the hydrophobicity of the amino acid, the surface exposure/structural nature of the amino acid, and the secondary structure propensity of the amino acid.

TABLE 1

| Groupings of conservative amino acid substitutions based on the functionality of the residue in the protein. | |
|---|---|
| Important Feature | Conservative Groupings |
| Charge/Polarity | 1. H, R, and K |
| | 2. D and E |
| | 3. C, T, S, G, N, Q, and Y |
| | 4. A, P, M, L, I, V, F, and W |
| Hydrophobicity | 1. D, E, N, Q, R, and K |
| | 2. C, S, T, P, G, H, and Y |
| | 3. A, M, I, L, V, F, and W |
| Structural/Surface Exposure | 1. D, E, N, Q, H, R, and K |
| | 2. C, S, T, P, A, G, W, and Y |
| | 3. M, I, L, V, and F |

TABLE 1-continued

| Groupings of conservative amino acid substitutions based on the functionality of the residue in the protein. | |
|---|---|
| Important Feature | Conservative Groupings |
| Secondary Structure Propensity | 1. A, E, Q, H, K, M, L, and R |
| | 2. C, T, I, V, F, Y, and W |
| | 3. S, G, P, D, and N |
| Evolutionary Conservation | 1. D and E |
| | 2. H, K, and R |
| | 3. N and Q |
| | 4. S and T |
| | 5. L, I, and V |
| | 6. F, Y, and W |
| | 7. A and G |
| | 8. M and C |

The terms "identical" or percent "identity," in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using, e.g., a BLAST or BLAST 2.0 sequence comparison algorithms with default parameters described below, or by manual alignment and visual inspection.

As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc, all of which are incorporated by reference.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989), both incorporated by reference. Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403-410, (1990); Altschul et al., Nucleic Acids Res.

25:3389-3402 (1997); and Karlin et al., Proc. Natl. Acad. Sci. U.S.A. 90:5873-5787 (1993), both incorporated by reference. A particularly useful BLAST program is the WU-BLAST-2 program which was obtained from Altschul et al., Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389-3402, incorporated by reference. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). In a similar manner, "percent (%) nucleic acid sequence identity" with respect to the coding sequence of the polypeptides identified is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 2 (SEQ ID NO: 1), it is understood that in one embodiment, the percentage of sequence identity will be determined based on the number of identical amino acids or nucleotides in relation to the total number of amino acids or nucleotides. Thus, for example, sequence identity of sequences shorter than that shown in FIG. 2 (SEQ ID NO: 1), as discussed below, will be determined using the number of nucleotides in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

The term "allelic variants" refers to polymorphic forms of a gene at a particular genetic locus, as well as cDNAs derived from mRNA transcripts of the genes, and the polypeptides encoded by them. The term "preferred mammalian codon" refers a subset of codons from among the set of codons encoding an amino acid that are most frequently used in proteins expressed in mammalian cells as chosen from the following list: Gly (GGC, GGG); Glu (GAG); Asp (GAC); Val (GTG, GTC); Ala (GCC, GCT); Ser (AGC, TCC); Lys (AAG); Asn (AAC); Met (ATG); Ile (ATC); Thr (ACC); Trp (TGG); Cys (TGC); Tyr (TAT, TAC); Leu (CTG); Phe (TTC); Arg (CGC, AGG, AGA); Gln (CAG); His (CAC); and Pro (CCC).

As used herein, the term codon-altered refers to a polynucleotide sequence encoding a polypeptide (e.g., a Factor VIII variant protein), where at least one codon of the native polynucleotide encoding the polypeptide has been changed to improve a property of the polynucleotide sequence. In some embodiments, the improved property promotes increased transcription of mRNA coding for the polypeptide, increased stability of the mRNA (e.g., improved mRNA half-life), increased translation of the polypeptide, and/or increased packaging of the polynucleotide within the vector. Non-limiting examples of alterations that can be used to achieve the improved properties include changing the usage and/or distribution of codons for particular amino acids, adjusting global and/or local GC content, removing AT-rich sequences, removing repeated sequence elements, adjusting global and/or local CpG dinucleotide content, removing cryptic regulatory elements (e.g., TATA box and CCAAT box elements), removing of intron/exon splice sites, improving regulatory sequences (e.g., introduction of a Kozak consensus sequence), and removing sequence elements capable of forming secondary structure (e.g., stem-loops) in the transcribed mRNA.

As discussed herein, there are various nomenclatures to refer to components of the disclosure herein. "CS-number" (e.g. "CS04") refer to codon altered polynucleotides encoding FVIII polypeptides and/or the encoded polypeptides, including variants. For example, CS04-FL refers to the Full Length codon altered CS04 polynucleotide sequence or amino acid sequence (sometimes referred to herein as "CS04-FL-AA" for the Amino Acid sequence and "CS04-FL-NA" for the Nucleic Acid sequence) encoded by the CS04 polynucleotide sequence. Similarly, "CS04-LC" refers to either the codon altered nucleic acid sequence ("CS04-LC-NA") encoding the light chain of a FVIII polypeptide or the amino acid sequence (also sometimes referred to herein as "CS04-LC-AA") of the FVIII light chain encoded by the CS04 polynucleotide sequence. Likewise, CS04-HC, CS04-HC-AA and CS04-HC-NA are the same for the FVIII heavy chain. As will be appreciated by those in the art, for constructs such as CS04, that are only codon-altered (e.g. they do not contain additional amino acid substitutions as compared to Refacto), the amino acid sequences will be identical, as the amino acid sequences are not altered by the codon optimization. Thus, sequence constructs of the disclosure include, but are not limited to, CS04-FL-NA, CS04-FL-AA, CS04-LC-NA, CS04-LC-AA, CS04-HC-AA, and CS04-HC-NA.

III. CODON-ALTERED FACTOR VIII VARIANTS

In some embodiments, the present disclosure provides codon-altered polynucleotides encoding Factor VIII variants. These codon-altered polynucleotides provide markedly improved expression of Factor VIII when administered in an AAV-based gene therapy construct. The codon-altered polynucleotides also demonstrate improved AAV-virion packaging, as compared to conventionally codon-optimized constructs. As demonstrated in Example 2 and Table 4, Applicants have achieve these advantages through the discovery of a codon-altered polynucleotide (CS04-FL-NA) encoding a Factor VIII polypeptide with human wild-type Factor VIII heavy and light chains, and a short, 14 amino acid, B-domain substituted linker (the "SQ" linker) containing a furin cleavage site to facilitate maturation of an active FVIIIa protein in vivo.

In one embodiment, a codon-altered polynucleotide provided herein has nucleotide sequences with high sequence identity to at least the sequences within CS04 (SEQ ID NO: 1) encoding the Factor VIII heavy chain and Factor VIII light chains. As known in the art, the B-domain of Factor VIII is dispensable for activity in vivo. Thus, in some embodiments, the codon-altered polynucleotides provided herein completely lack a Factor VIII B-domain. In some embodiments, the native Factor VIII B-domain is replaced with a short amino acid linker containing a furin cleavage site, e.g., the "SQ" linker consisting of amino acids 760-773 of the CS04 (SEQ ID NOS 2) constructs. The "SQ" linker is also referred to as BDLO04, (-AA for the amino acid sequence and -NA for the nucleotide sequence).

In one embodiment, the Factor VIII heavy and light chains encoded by the codon-altered polynucleotide are human Factor VIII heavy and light chains, respectively. In other embodiments, the Factor VIII heavy and light chains encoded by the codon-altered polynucleotide are heavy and light chain sequences from another mammal (e.g., porcine Factor VIII). In yet other embodiments, the Factor VIII heavy and light chains are chimeric heavy and light chains (e.g., a combination of human and a second mammalian sequence). In yet other embodiments, the Factor VIII heavy and light chains are humanized version of the heavy and light chains from another mammal, e.g., heavy and light chain sequences from another mammal in which human residues are substituted at select positions to reduce the immunogenicity of the resulting peptide when administered to a human.

The GC content of human genes varies widely, from less than 25% to greater than 90%. However, in general, human genes with higher GC contents are expressed at higher levels. For example, Kudla et al. (PLoS Biol., 4(6):80 (2006)) demonstrate that increasing a gene's GC content increases expression of the encoded polypeptide, primarily by increasing transcription and effecting a higher steady state level of the mRNA transcript. Generally, the desired GC content of a codon-optimized gene construct is equal or greater than 60%. However, native AAV genomes have GC contents of around 56%.

Accordingly, in some embodiments, the codon-altered polynucleotides provided herein have a CG content that more closely matches the GC content of native AAV virions (e.g., around 56% GC), which is lower than the preferred CG contents of polynucleotides that are conventionally codon-optimized for expression in mammalian cells (e.g., at or above 60% GC). As outlined in Example 1, CS04-FL-NA (SEQ ID NO: 1), which has a GC content of about 56%, has improved virion packaging as compared to similarly codon-altered coding sequences with higher GC content.

Thus, in some embodiments, the overall GC content of a codon-altered polynucleotide encoding a Factor VIII polypeptide is less than 60%. In some embodiments, the overall GC content of a codon-altered polynucleotide encoding a Factor VIII polypeptide is less than 59%. In some embodiments, the overall GC content of a codon-altered polynucleotide encoding a Factor VIII polypeptide is less than 58%. In some embodiments, the overall GC content of a codon-altered polynucleotide encoding a Factor VIII polypeptide is less than 57%. In some embodiments, the overall GC content of a codon-altered polynucleotide encoding a Factor VIII polypeptide is no more than 56%.

In some embodiments, the overall GC content of a codon-altered polynucleotide encoding a Factor VIII polypeptide is from 54% to 59%. In some embodiments, the overall GC content of a codon-altered polynucleotide encoding a Factor VIII polypeptide is from 55% to 59%. In some embodiments, the overall GC content of a codon-altered polynucleotide encoding a Factor VIII polypeptide is from 56% to 59%. In some embodiments, the overall GC content of a codon-altered polynucleotide encoding a Factor VIII polypeptide is from 54% to 58%. In some embodiments, the overall GC content of a codon-altered polynucleotide encoding a Factor VIII polypeptide is from 55% to 58%. In some embodiments, the overall GC content of a codon-altered polynucleotide encoding a Factor VIII polypeptide is from 56% to 58%. In some embodiments, the overall GC content of a codon-altered polynucleotide encoding a Factor VIII polypeptide is from 54% to 57%. In some embodiments, the overall GC content of a codon-altered polynucleotide encoding a Factor VIII polypeptide is from 55% to 57%. In some embodiments, the overall GC content of a codon-altered polynucleotide encoding a Factor VIII polypeptide is from 56% to 57%. In some embodiments, the overall GC content of a codon-altered polynucleotide encoding a Factor VIII polypeptide is from 54% to 56%. In some embodiments, the overall GC content of a codon-altered polynucleotide encoding a Factor VIII polypeptide is from 55% to 56%.

In some embodiments, the overall GC content of a codon-altered polynucleotide encoding a Factor VIII polypeptide is 56±0.5%. In some embodiments, the overall GC content of a codon-altered polynucleotide encoding a Factor VIII polypeptide is 56±0.4%. In some embodiments, the overall GC content of a codon-altered polynucleotide encoding a Factor VIII polypeptide is 56±0.3%. In some embodiments, the overall GC content of a codon-altered polynucleotide encoding a Factor VIII polypeptide is 56±0.2%. In some embodiments, the overall GC content of a codon-altered polynucleotide encoding a Factor VIII polypeptide is 56±0.1%. In some embodiments, the overall GC content of a codon-altered polynucleotide encoding a Factor VIII polypeptide is 56%.

A. Factor VIII B-Domain Substituted Linkers

In some embodiments, the linkage between the FVIII heavy chain and the light chain (e.g., the B-domain in wild-type Factor VIII) is further altered. Due to size constraints of AAV packaging capacity, B-domain deleted, truncated, and or linker substituted variants should improve the efficacy of the FVIII gene therapy construct. The most conventionally used B-domain substituted linker is that of SQ FVIII, which retains only 14 amino acids of the B domain as linker sequence. Another variant of porcine VIII ("OBI-1," described in U.S. Pat. No. 6,458,563) is well expressed in CHO cells, and has a slightly longer linker of 24 amino acids. In some embodiments, the Factor VIII constructs encoded by the codon-altered polynucleotides described herein include an SQ-type B-domain linker sequence. In other embodiments, the Factor VIII constructs encoded by the codon-altered polynucleotides described herein include an OBI-1-type B-domain linker sequence.

In some embodiments, the encoded Factor VIII polypeptides described herein include an SQ-type B-domain linker (SFSQNPPVLKRHQR; BDL-SQ-AA; SEQ ID NO: 13), including amino acids 760-762/1657-1667 of the wild-type human Factor VIII B-domain (FVIII-FL-AA; SEQ ID NO: 12) (Sandberg et al. Thromb. Haemost. 85:93 (2001)). In some embodiments, the SQ-type B-domain linker has one amino acid substitution relative to the corresponding wild-type sequence. In some embodiments, the SQ-type B-domain linker has two amino acid substitutions relative to the corresponding wild-type sequence.

In some embodiments, the encoded Factor VIII polypeptides described herein include a Greengene-type B-domain linker, including amino acids 760/1582-1667 of the wild-type human Factor VIII B-domain (FVIII-FL-AA; SEQ ID NO: 12) (Oh et al., Biotechnol. Prog., 17:1999 (2001)). In some embodiments, the Greengene-type B-domain linker has one amino acid substitution relative to the corresponding wild-type sequence. In some embodiments, the Greengene-type B-domain linker has two amino acid substitutions relative to the corresponding wild-type sequence.

In some embodiments, the encoded Factor VIII polypeptides described herein include an extended SQ-type B-domain linker, including amino acids 760-769/1657-1667 of the wild-type human Factor VIII B-domain (FVIII-FL-AA; SEQ ID NO: 12) (Thim et al., Haemophilia, 16:349 (2010)). In some embodiments, the extended SQ-type B-domain linker has one amino acid substitution relative to the corresponding wild-type sequence. In some embodiments, the extended SQ-type B-domain linker has two amino acid substitutions relative to the corresponding wild-type sequence.

In some embodiments, the encoded Factor VIII polypeptides described herein include a porcine OBI-1-type B-domain linker, including the amino acids SFAQNSRPP-SASAPKPPVLRRHQR (SEQ ID NO: 14) from the wild-type porcine Factor VIII B-domain (Toschi et al., Curr. Opin. Mol. Ther. 12:517 (2010)). In some embodiments, the porcine OBI-1-type B-domain linker has one amino acid substitution relative to the corresponding wild-type sequence. In some embodiments, the porcine OBI-1-type B-domain linker has two amino acid substitutions relative to the corresponding wild-type sequence.

In some embodiments, the encoded Factor VIII polypeptides described herein include a human OBI-1-type B-domain linker, including amino acids 760-772/1655-1667 of the wild-type human Factor VIII B-domain (FVIII-FL-AA; SEQ ID NO: 12). In some embodiments, the human OBI-1-type B-domain linker has one amino acid substitution relative to the corresponding wild-type sequence. In some embodiments, the human OBI-1-type B-domain linker has two amino acid substitutions relative to the corresponding wild-type sequence.

In some embodiments, the encoded Factor VIII polypeptides described herein include an 08-type B-domain linker, including the amino acids SFSQNSRHQAYRYRRG (SEQ ID NO: 15) from the wild-type porcine Factor VIII B-domain (Toschi et al., Curr. Opin. Mol. Ther. 12:517 (2010)). In some embodiments, the porcine OBI-1-type B-domain linker has one amino acid substitution relative to the corresponding wild-type sequence. In some embodiments, the porcine OBI-1-type B-domain linker has two amino acid substitutions relative to the corresponding wild-type sequence.

B. Codon-Altered Polynucleotides Encoding a Factor VIII Variant with a Cleavable Linker CS04 Codon Altered Polynucleotides In one embodiment, the codon-altered polynucleotides provided herein include a nucleotide sequence encoding a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS04-HC-NA and CS04-LC-NA (SEQ ID NOS 3 and 4), respectively. In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively.

In some embodiments, the polypeptide linker of the Factor VIII construct is encoded by a third nucleotide sequence having high sequence identity to BDLO04 (SEQ ID NO: 5), which encodes the 14-amino acid linker corresponding to amino acids 760-773 of CS04-FL-AA (SEQ ID NO: 2). In some embodiments, the third nucleotide sequence has at least 95% identity to BDLO04 (SEQ ID NO: 5). In some embodiments, the third nucleotide sequence has at least 96% identity to BDLO04 (SEQ ID NO: 5). In some embodiments, the third nucleotide sequence has at least 97% identity to BDLO04 (SEQ ID NO: 5). In some embodiments, the third nucleotide sequence has at least 98% identity to BDLO04 (SEQ ID NO: 5). In some embodiments, the third nucleotide sequence is identical to BDLO04 (SEQ ID NO: 5).

In some embodiments, the codon-altered polynucleotide has a nucleotide sequence with high sequence identity to CS04-FL-NA (SEQ ID NO: 1). In some embodiments, the nucleotide sequence has at least 95% identity to CS04-FL-NA (SEQ ID NO: 1). In some embodiments, the nucleotide sequence has at least 96% identity to CS04-FL-NA (SEQ ID NO: 1). In some embodiments, the nucleotide sequence has at least 97% identity to CS04-FL-NA (SEQ ID NO: 1). In some embodiments, the nucleotide sequence has at least 98% identity to CS04-FL-NA (SEQ ID NO: 1). In some embodiments, the nucleotide sequence has at least 99% identity to CS04-FL-NA (SEQ ID NO: 1). In some embodiments, the nucleotide sequence has at least 99.5% identity to CS04-FL-NA (SEQ ID NO: 1). In some embodiments, the nucleotide sequence has at least 99.9% identity to CS04-FL-NA (SEQ ID NO: 1). In some embodiments, the nucleotide sequence is identical to CS04-FL-NA (SEQ ID NO: 1).

In some embodiments, the Factor VIII variant encoded by the codon-altered polynucleotide has an amino acid sequence with high sequence identity to CS04-FL-AA (SEQ ID NO: 2). In some embodiments, the amino acid sequence has at least 97% identity to CS04-FL-AA (SEQ ID NO: 2). In some embodiments, the amino acid sequence has at least 98% identity to CS04-FL-AA (SEQ ID NO: 2). In some embodiments, the amino acid sequence has at least 99% identity to CS04-FL-AA (SEQ ID NO: 2). In some embodiments, the amino acid sequence has at least 99.5% identity to CS04-FL-AA (SEQ ID NO: 2). In some embodiments, the amino acid sequence has at least 99.9% identity to CS04-FL-AA (SEQ ID NO: 2). In some embodiments, the amino acid sequence is identical to CS04-FL-AA (SEQ ID NO: 2).

C. Factor VIII Expression Vectors

In some embodiments, the codon-altered polynucleotides described herein are integrated into expression vectors. Non-limiting examples of expression vectors include viral vectors (e.g., vectors suitable for gene therapy), plasmid vectors, bacteriophage vectors, cosmids, phagemids, artificial chromosomes, and the like.

Non-limiting examples of viral vectors include: retrovirus, e.g., Moloney murine leukemia virus (MMLV), Harvey murine sarcoma virus, murine mammary tumor virus, and Rous sarcoma virus; adenoviruses, adeno-associated viruses; SV40-type viruses; polyomaviruses; Epstein-Barr viruses; papilloma viruses; herpes viruses; vaccinia viruses; and polio viruses.

In some embodiments, the codon-altered polynucleotides described herein are integrated into a gene therapy vector. In some embodiments, the gene therapy vector is a retrovirus, and particularly a replication-deficient retrovirus. Protocols for the production of replication-deficient retroviruses are known in the art. For review, see Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the gene therapy vector is an adeno-associated virus (AAV) based gene therapy vector. AAV systems have been described previously and are generally well known in the art (Kelleher and Vos, Biotechniques, 17(6):1110-17 (1994); Cotten et al., Proc Natl Acad Sci USA, 89(13):6094-98 (1992); Curiel, Nat Immun, 13(2-3): 141-64 (1994); Muzyczka, Curr Top Microbiol Immunol, 158:97-129 (1992); and Asokan A, et al., Mol. Ther., 20(4): 699-708 (2012), each incorporated herein by reference in their entireties for all purposes). Details concerning the generation and use of rAAV vectors are described, for example, in U.S. Pat. Nos. 5,139,941 and 4,797,368, each incorporated herein by reference in their entireties for all purposes. In a particular embodiment, the AAV vector is an AAV-8 vector.

In some embodiments, the codon-altered polynucleotides described herein are integrated into a retroviral expression vector. These systems have been described previously, and are generally well known in the art (Mann et al., Cell, 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., Science, 272(5259):263-267, 1996; Zufferey et al., Nat Biotechnol, 15(9):871-875, 1997; Blomer et al., J Virol., 71(9):6641-6649, 1997; U.S. Pat. Nos. 6,013,516 and 5,994,136).

A wide variety of vectors can be used for the expression of a Factor VIII polypeptide from a codon-altered polypeptide in cell culture, including eukaryotic and prokaryotic expression vectors. In certain embodiments, a plasmid vector is contemplated for use in expressing a Factor VIII polypeptide in cell culture. In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will include the codon-altered polynucleotide encoding the Factor VIII polypeptide, operably linked to one or more control sequences, for example, a promoter.

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

D. Dosing

The invention provides the administration of the codon-optimized constructs of the invention to human patients that have been diagnosed with hemophilia A (a "hemophilia A patient" or "patient"). In general, as outlined herein, the administration is done using AAV particles that contain the codon-optimized constructs of the invention. Furthermore, as is more fully described below, the administration of the constructs of the invention can be augmented by the administration of prednisolone or prednisone as well.

$2 \times 10^{12}$ adeno-associated virus (AAV) particles per kilogram body weight In one aspect, the disclosure provides a method for treating hemophilia A including intravenously infusing (e.g., by peripheral intravenous infusion), to a hemophilia A patient, a dose of $2 \times 10^{12}$ adeno-associated virus (AAV) particles per kilogram body weight of the human patient, where the AAV particles include a codon-altered polynucleotide encoding a Factor VIII polypeptide, having high sequence identity to SEQ ID NO: 1 (CS04-FL-NA).

In one embodiment, the codon-altered polynucleotide having high sequence identity to SEQ ID NO: 1 (CS04-FL-NA), that is administered to the human patient at a dose of $2 \times 10^{12}$ adeno-associated virus (AAV) particles per kilogram body weight of the human patient, encodes a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS04-HC-NA and CS04-LC-NA (SEQ ID NOS 3 and 4), respectively. In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively. In these embodiments, the amino acid sequence encoded by these nucleotide sequences are identical to CS04-HC-AA and CS04-LC-AA.

In some embodiments, the polypeptide linker of the Factor VIII construct is encoded by a third nucleotide sequence having high sequence identity to BDLO04 (SEQ ID NO: 5), which encodes the 14-amino acid linker corresponding to amino acids 760-773 of CS04-FL-AA (SEQ ID NO: 2). In some embodiments, the third nucleotide sequence has at least 95% identity to BDLO04 (SEQ ID NO: 5). In some embodiments, the third nucleotide sequence has at least 96% identity to BDLO04 (SEQ ID NO: 5). In some embodiments, the third nucleotide sequence has at least 97% identity to BDLO04 (SEQ ID NO: 5). In some embodiments, the third nucleotide sequence has at least 98% identity to BDLO04 (SEQ ID NO: 5). In some embodiments, the third nucleotide sequence is identical to BDLO04 (SEQ ID NO: 5). In these embodiments, the amino acid sequence encoded by these nucleotide sequences are identical to amino acids 760-773 of CS04-FL-AA (SEQ ID NO: 2). In some embodiments, the codon-altered polynucleotide), that is administered to the human patient at a dose of 2×10 adeno-associated virus (AAV) particles per kilogram body weight of the human patient, has a nucleotide sequence with high sequence identity to CS04-FL-NA (SEQ ID NO: 1). In some embodiments, the nucleotide sequence has at least 95% identity to CS04-FL-NA (SEQ ID NO: 1). In some embodiments, the nucleotide sequence has at least 96% identity to CS04-FL-NA (SEQ ID NO: 1). In some embodiments, the nucleotide sequence has at least 97% identity to CS04-FL-NA (SEQ ID NO: 1). In some embodiments, the nucleotide sequence has at least 98% identity to CS04-FL-NA (SEQ ID NO: 1). In some embodiments, the nucleotide sequence has at least 99% identity to CS04-FL-NA (SEQ ID NO: 1). In some embodiments, the nucleotide sequence has at least 99.5% identity to CS04-FL-NA (SEQ ID NO: 1). In some embodiments, the nucleotide sequence has at least 99.9% identity to CS04-FL-NA (SEQ ID NO: 1). In some embodiments, the nucleotide sequence is identical to CS04-FL-NA (SEQ ID NO: 1). In these embodiments, the amino acid sequence encoded by these nucleotide sequences is identical to CS04-FL-AA.

In some embodiments, the Factor VIII variant encoded by the codon-altered polynucleotide has an amino acid sequence with high sequence identity to CS04-FL-AA (SEQ ID NO: 2). In some embodiments, the amino acid sequence has at least 97% identity to CS04-FL-AA (SEQ ID NO: 2). In some embodiments, the amino acid sequence has at least 98% identity to CS04-FL-AA (SEQ ID NO: 2). In some embodiments, the amino acid sequence has at least 99% identity to CS04-FL-AA (SEQ ID NO: 2). In some embodiments, the amino acid sequence has at least 99.5% identity to CS04-FL-AA (SEQ ID NO: 2). In some embodiments, the amino acid sequence has at least 99.9% identity to CS04-FL-AA (SEQ ID NO: 2). In some embodiments, the amino acid sequence is identical to CS04-FL-AA (SEQ ID NO: 2).

Accordingly, in one embodiment, the disclosure provides a method for treating hemophilia A that includes intravenously infusing, to a hemophilia A patient, a dose of 2×10 adeno-associated virus (AAV) particles per kilogram body weight of the human patient, where the AAV particles include a polynucleotide having a nucleic acid sequence of SEQ ID NO: 1 (CS04-FL-NA).

In some embodiments, the AAV particles are administered in a single dose by intravenous infusion (e.g., into a vein in the patient's arm). In some embodiments, a portion of the single dose is administered, the patient is monitored for signs of an adverse reaction to the administration for a brief period of time (e.g., 30 minutes), and then (e.g., if no signs of an adverse reaction appear) the remaining portion of the single dose is administered to the patient.

In some embodiments, the human patient administered the AAV particles has severe hemophilia A. For example, in some embodiments, the patient has a level of Factor VIII activity in their blood stream, when not receiving Factor VIII replacement therapy, that is less than 2% of the amount of Factor VIII activity found in a reference blood sample, e.g., a blood sample with normal Factor VIII activity (e.g., a blood sample from a subject determined not to have hemophilia A), or an average Factor VIII activity found in the blood samples of a plurality of subjects determining not to have hemophilia A. In some embodiments, the subject has a level of Factor VIII activity in their blood stream, when not receiving Factor VIII replacement therapy, that is less than 2% of the amount of Factor VIII activity found in a reference blood sample.

In some embodiments, the human patient administered the AAV particles does not have inhibitors to FVIII (e.g., Factor VIII inhibitor antibodies), does not have haemostatic defects other than severe hemophilia A, does not have chronic hepatic dysfunction, and/or does not have severe renal impairment.

Accordingly, in some embodiments, the methods described herein include a step of qualifying a patient for administration of a dose of $2 \times 10^{12}$ adeno-associated virus (AAV) particles per kilogram body weight of the human patient, where the AAV particles include a codon-altered polynucleotide encoding a Factor VIII polypeptide, having high sequence identity to SEQ ID NO: 1 (CS04-FL-NA). The method includes determining a level of Factor VIII activity in the blood stream of the patient, when the patient is not receiving a Factor VIII replacement therapy, and qualifying the patient for administration of the AAV particles when the level of Factor VIII activity in the patient's blood stream is less than about 2%, or less than about 1%, of the level of Factor VIII in a reference samples. In some embodiments, the method includes determining whether the patient has one or more of inhibitors to FVIII (e.g., Factor VIII inhibitor antibodies), a haemostatic defect other than severe hemophilia A, chronic hepatic dysfunction, and severe renal impairment, and disqualifying the patient if they have any of the enumerated conditions.

$6 \times 10^{12}$ adeno-associated virus (AAV) particles per kilogram body weight In one aspect, the disclosure provides a method for treating hemophilia A including intravenously infusing (e.g., by peripheral intravenous infusion), to a hemophilia A patient, a dose of 6×10 adeno-associated virus (AAV) particles per kilogram body weight of the human patient, where the AAV particles include a codon-altered polynucleotide encoding a Factor VIII polypeptide, having high sequence identity to SEQ ID NO: 1 (CS04-FL-NA).

In one embodiment, the codon-altered polynucleotide having high sequence identity to SEQ ID NO: 1 (CS04-FL-NA), that is administered to the human patient at a dose of 6×10 adeno-associated virus (AAV) particles per kilogram body weight of the human patient, encodes a Factor VIII variant polypeptide with a linker that is cleavable in vivo. The Factor VIII polypeptide includes a Factor VIII light chain, a Factor VIII heavy chain, and a polypeptide linker joining the C-terminus of the heavy chain to the N-terminus of the light chain. The heavy chain of the Factor VIII polypeptide is encoded by a first nucleotide sequence having high sequence identity to CS04-HC-NA (SEQ ID NO: 3), which is the portion of CS04-FL-NA (SEQ ID NO: 1) encoding for a Factor VIII heavy chain. The light chain of the Factor VIII polypeptide is encoded by a second nucleotide sequence with high sequence identity to CS04-LC-NA (SEQ ID NO: 4), which is the portion of CS04-FL-NA (SEQ ID NO: 1) encoding for a Factor VIII light chain. The polypeptide linker includes a furin cleavage site, which allows for maturation in vivo (e.g., after expression in vivo or administration of the precursor polypeptide).

In some embodiments, the first and second nucleotide sequences have at least 95% sequence identity to CS04-HC-NA and CS04-LC-NA (SEQ ID NOS 3 and 4), respectively. In some embodiments, the first and second nucleotide sequences have at least 96% sequence identity to CS04-HC-NA and CS04-LC-NA (SEQ ID NOS 3 and 4), respectively. In some embodiments, the first and second nucleotide sequences have at least 97% sequence identity to CS04-HC-NA and CS04-LC-NA (SEQ ID NOS 3 and 4), respectively. In some embodiments, the first and second nucleotide sequences have at least 98% sequence identity to CS04-HC-NA and CS04-LC-NA (SEQ ID NOS 3 and 4), respectively. In some embodiments, the first and second nucleotide sequences have at least 99% sequence identity to CS04-HC-NA and CS04-LC-NA (SEQ ID NOS 3 and 4), respectively. In some embodiments, the first and second nucleotide sequences have at least 99.5% sequence identity to CS04-HC-NA and CS04-LC-NA (SEQ ID NOS 3 and 4), respectively. In some embodiments, the first and second nucleotide sequences have at least 99.9% sequence identity to CS04-HC-NA and CS04-LC-NA (SEQ ID NOS 3 and 4), respectively. In some embodiments, the first and second nucleotide sequences are identical to CS04-HC-NA and CS04-LC-NA (SEQ ID NOS 3 and 4), respectively. In these embodiments, the amino acid sequence encoded by these nucleotide sequences are identical to CS04-HC-AA and CS04-LC-AA.

In some embodiments, the polypeptide linker of the Factor VIII construct is encoded by a third nucleotide sequence having high sequence identity to BDLO04 (SEQ ID NO: 5), which encodes the 14-amino acid linker corresponding to amino acids 760-773 of CS04-FL-AA (SEQ ID NO: 2). In some embodiments, the third nucleotide sequence has at least 95% identity to BDLO04 (SEQ ID NO: 5). In some embodiments, the third nucleotide sequence has at least 96% identity to BDLO04 (SEQ ID NO: 5). In some embodiments, the third nucleotide sequence has at least 97% identity to BDLO04 (SEQ ID NO: 5). In some embodiments, the third nucleotide sequence has at least 98% identity to BDLO04 (SEQ ID NO: 5). In some embodiments, the third nucleotide sequence is identical to BDLO04 (SEQ ID NO: 5). In these embodiments, the amino acid sequence encoded by these nucleotide sequences are identical to amino acids 760-773 of CS04-FL-AA (SEQ ID NO: 2).

In some embodiments, the codon-altered polynucleotide), that is administered to the human patient at a dose of 6×10 adeno-associated virus (AAV) particles per kilogram body weight of the human patient, has a nucleotide sequence with high sequence identity to CS04-FL-NA (SEQ ID NO: 1). In some embodiments, the nucleotide sequence has at least 95% identity to CS04-FL-NA (SEQ ID NO: 1). In some embodiments, the nucleotide sequence has at least 96% identity to CS04-FL-NA (SEQ ID NO: 1). In some embodiments, the nucleotide sequence has at least 97% identity to CS04-FL-NA (SEQ ID NO: 1). In some embodiments, the nucleotide sequence has at least 98% identity to CS04-FL-NA (SEQ ID NO: 1). In some embodiments, the nucleotide sequence has at least 99% identity to CS04-FL-NA (SEQ ID NO: 1). In some embodiments, the nucleotide sequence has at least 99.5% identity to CS04-FL-NA (SEQ ID NO: 1). In some embodiments, the nucleotide sequence has at least 99.9% identity to CS04-FL-NA (SEQ ID NO: 1). In some embodiments, the nucleotide sequence is identical to CS04-FL-NA (SEQ ID NO: 1). In these embodiments, the amino acid sequence encoded by these nucleotide sequences is identical to CS04-FL-AA.

In some embodiments, the Factor VIII variant encoded by the codon-altered polynucleotide has an amino acid sequence with high sequence identity to CS04-FL-AA (SEQ ID NO: 2). In some embodiments, the amino acid sequence has at least 97% identity to CS04-FL-AA (SEQ ID NO: 2). In some embodiments, the amino acid sequence has at least 98% identity to CS04-FL-AA (SEQ ID NO: 2). In some embodiments, the amino acid sequence has at least 99% identity to CS04-FL-AA (SEQ ID NO: 2). In some embodiments, the amino acid sequence has at least 99.5% identity to CS04-FL-AA (SEQ ID NO: 2). In some embodiments, the amino acid sequence has at least 99.9% identity to CS04-FL-AA (SEQ ID NO: 2). In some embodiments, the amino acid sequence is identical to CS04-FL-AA (SEQ ID NO: 2).

Accordingly, in one embodiment, the disclosure provides a method for treating hemophilia A that includes intravenously infusing, to a hemophilia A patient, a dose of 6×10 adeno-associated virus (AAV) particles per kilogram body weight of the human patient, where the AAV particles include a polynucleotide having a nucleic acid sequence of SEQ ID NO: 1 (CS04-FL-NA).

In some embodiments, the AAV particles are administered in a single dose by intravenous infusion (e.g., into a vein in the patient's arm). In some embodiments, a portion of the single dose is administered, the patient is monitored for signs of an adverse reaction to the administration for a brief period of time (e.g., 30 minutes), and then (e.g., if no signs of an adverse reaction appear) the remaining portion of the single dose is administered to the patient.

In some embodiments, the human patient administered the AAV particles has severe hemophilia A. For example, in some embodiments, the patient has a level of Factor VIII activity in their blood stream, when not receiving Factor VIII replacement therapy, that is less than 2% of the amount of Factor VIII activity found in a reference blood sample, e.g., a blood sample with normal Factor VIII activity (e.g., a blood sample from a subject determined not to have hemophilia A), or an average Factor VIII activity found in the blood samples of a plurality of subjects determining not to have hemophilia A. In some embodiments, subject has a level of Factor VIII activity in their blood stream, when not receiving Factor VIII replacement therapy, that is less than 2% of the amount of Factor VIII activity found in a reference blood sample.

In some embodiments, the human patient administered the AAV particles does not have inhibitors to FVIII (e.g., Factor VIII inhibitor antibodies), does not have haemostatic defects other than severe hemophilia A, does not have chronic hepatic dysfunction, and/or does not have severe renal impairment.

Accordingly, in some embodiments, the methods described herein include a step of qualifying a patient for administration of a dose of 6×10 adeno-associated virus (AAV) particles per kilogram body weight of the human patient, where the AAV particles include a codon-altered polynucleotide encoding a Factor VIII polypeptide, having high sequence identity to SEQ ID NO: 1 (CS04-FL-NA). The method includes determining a level of Factor VIII activity in the blood stream of the patient, when the patient is not receiving a Factor VIII replacement therapy, and qualifying the patient for administration of the AAV particles when the level of Factor VIII activity in the patient's blood stream is less than about 2%, or less than about 1%, of the level of Factor VIII in a reference samples. In some embodiments, the method includes determining whether the patient has one or more of inhibitors to FVIII (e.g., Factor VIII inhibitor antibodies), a haemostatic defect other than severe hemophilia A, chronic hepatic dysfunction, and severe renal impairment, and disqualifying the patient if they have any of the enumerated conditions.

Co-Administration with Prednisolone or Prednisone

In some embodiments, the methods described above for treating hemophilia A by administering AAV particles at either dose also include administering, to the human patient, a course of prednisolone or prednisone, e.g., to reduce the level of an inflammatory response, for example, by lowering the subject's production of cytokines and/or chemokines. Example methods for co-administering prednisolone or prednisone with a gene therapy are described, for example, in International Patent Application Publication No. WO 2008/069942, the content of which is incorporated herein by reference, in its entirety, for all purposes.

In some embodiments, prednisolone or prednisone is administered to the human patient prior to administering the adeno-associated virus (AAV) particles, with the polynucleotide encoding the Factor VIII polypeptide, having high sequence identity to SEQ ID NO: 1 (CS04-FL-NA). For example, in some embodiments, prednisolone or prednisone is administered about a week, or about one or two days, before the AAV particles are administered to the patient. In some embodiments, a course of prednisolone or prednisone is administered starting about a week, or about one or two days, before the AAV particles are administered, and is continued after administration of the AAV particles.

In some embodiments, prednisolone or prednisone is co-administered to the human subject when administering the adeno-associated virus (AAV) particles with the polynucleotide encoding the Factor VIII polypeptide, having high sequence identity to SEQ ID NO: 1 (CS04-FL-NA). For example, in some embodiments, prednisolone or prednisone is administered on the same day, e.g., directly before or after administration of the AAV particles. In some embodiments, a course of prednisolone or prednisone is administered on the same day as the AAV particles are administered, and is continued after administration of the AAV particles.

In some embodiments, prednisolone or prednisone is administered to the patient after administering the adeno-associated virus (AAV) particles with the polynucleotide encoding the Factor VIII polypeptide, having high sequence identity to SEQ ID NO: 1 (CS04-FL-NA). For example, in some embodiments, prednisolone or prednisone is first administered about one or two days after AAV particles are administered to the patien.

It should be noted that prednisolone or prednisone is a small molecule drug that is administered orally (although it can also be administered intravenously), and thus "co-administration" in this context does not require that a single solution contains both drugs.

In some embodiments, the course of prednisolone or prednisone is administered to the patient over a period of at least two weeks, e.g., daily or every two days. In some embodiments, the course of prednisolone or prednisone is administered over a period of at least three weeks. In some embodiments, the dose of prednisolone or prednisone decreases during the course. For example, in one embodiment, the course begins with administration of about 60 mg of prednisolone or prednisone per day, and is reduced as the course progresses.

In one embodiment, the course includes administration of about 60 mg of prednisolone or prednisone per day to the human patient, during the first week of the course, administration of about 40 mg of prednisolone or prednisone per day to the patient, during the second week of the course, and administration of about 30 mg of prednisolone or prednisone per day to the patient, during the third week immediately following infusion of the AAV particles.

In some embodiments, the course includes further tapering administration of prednisolone or prednisone after the third week, e.g., administration of a tapering dose of prednisolone or prednisone. In one embodiment, the tapering dose of prednisolone or prednisone includes successively administering doses (e.g., one or more doses at each concentration) of about 20 mg prednisolone or prednisone per day, about 15 mg prednisolone or prednisone per day, about 10 mg prednisolone or prednisone per day, and about 5 mg prednisolone or prednisone per day.

In one embodiment, the tapering dose of prednisolone or prednisone includes administration of about 20 mg of prednisolone or prednisone per day to the patient, for 5 consecutive days (e.g., immediately) following completion of the initial course of prednisolone or prednisone, administration of about 15 mg of prednisolone or prednisone per day to the patient, for 3 consecutive days (e.g., immediately) following the 5 days on which the patient was administered 20 mg of prednisolone or prednisone, administration of about 10 mg of prednisolone or prednisone per day to the patient, for 3 consecutive days (e.g., immediately) following the 3 days on which the patient was administered 15 mg of prednisolone or prednisone, and administration of about 5 mg of prednisolone or prednisone per day to the patient, for 3 consecutive days (e.g., immediately) following the 3 days on which the patient was administered 10 mg of prednisolone or prednisone.

In one embodiment, the tapering dose of prednisolone or prednisone includes administration of about 30 mg of prednisolone or prednisone per day to the patient, for 7 consecutive days immediately following completion of the initial course of prednisolone or prednisone, administration of about 20 mg of prednisolone or prednisone per day to the patient, for 7 consecutive days immediately following the 7 days on which the patient was administered 30 mg of prednisolone or prednisone, administration of about 15 mg of prednisolone or prednisone per day to the patient, for 5 consecutive days immediately following the 7 days on which the human subject was administered 20 mg of prednisolone or prednisone, administration of about 10 mg of prednisolone or prednisone per day to the patient, for 5 consecutive days immediately following the 5 days on which the patient was administered 15 mg of prednisolone or prednisone, and administration of about 5 mg of prednisolone or prednisone per day to the patient, for 5 consecutive days immediately following the 5 days on which the patient was administered 10 mg of prednisolone or prednisone.

In some embodiments, the length of a tapering dose of prednisolone or prednisone administered to the patient is determined based on whether the patient is still exhibiting signs of liver inflammation at the end of the initial course of prednisolone or prednisone (e.g., as indicated by a reduction in Factor VIII levels, e.g., Factor VIII titer or Factor VIII activity, or increase in liver enzymes).

For example, in one embodiment, a first level of Factor VIII (e.g., titer or activity) in the blood stream of the patient (e.g., in a blood sample collected from a patient) is determined following administration of adeno-associated virus (AAV) particles including a polynucleotide encoding a Factor VIII protein to the patient, and while the patient is receiving an initial course of glucocorticoid steroid treatment. A second level of Factor VIII (e.g., titer or activity) in the blood stream of the patient is determined after completion of the initial course of glucocorticoid steroid treatment. The second level of Factor VIII is then compared to the first level of Factor VIII. The patient is administered a first tapering dose of the glucocorticoid steroid over a time period of no more than three weeks when the second level of Factor VIII is not decreasing (e.g., when the second level of Factor VIII is not less than the first level of Factor VIII, or not less than a threshold amount below the first level of Factor VIII). The patient is administered a second tapering dose of the glucocorticoid steroid over a time period exceeding three weeks when the second level of Factor VIII is decreasing (e.g., when the second level of Factor VIII is less than the first level of Factor VIII, or less than a threshold amount below the first level of Factor VIII).

Similarly, in some embodiments, a first level of liver enzymes (e.g., a liver enzyme titer or activity) in the blood stream of the patient is determined prior to (e.g., or shortly after) administration of adeno-associated virus (AAV) particles including a polynucleotide encoding a Factor VIII protein to the patient. A second level of level of liver enzymes (e.g., a liver enzyme titer or activity) in the blood stream of the patient is determined after completion of the initial course of glucocorticoid steroid treatment. The second level of liver enzymes is then compared to the first level of liver enzymes. The patient is administered a first tapering dose of the glucocorticoid steroid over a time period of no more than three weeks when the second level of liver enzymes is not increasing (e.g., when the second level of liver enzymes is not greater than the first level of liver enzymes, or not more than a threshold amount above the first level of liver enzymes). The patient is administered a second tapering dose of the glucocorticoid steroid over a time period exceeding three weeks when the second level of liver enzymes is increasing (e.g., when the second level of liver enzymes is greater than the first level of liver enzymes, or more than a threshold amount above the first level of liver enzymes).

In some embodiments, the first tapering dose of prednisolone or prednisone includes administration of about 20 mg of prednisolone or prednisone per day to the patient, for 5 consecutive days (e.g., immediately) following completion of the initial course of prednisolone or prednisone, administration of about 15 mg of prednisolone or prednisone per day to the patient, for 3 consecutive days (e.g., immediately) following the 5 days on which the patient was administered 20 mg of prednisolone or prednisone, administration of about 10 mg of prednisolone or prednisone per day to the patient, for 3 consecutive days (e.g., immediately) following the 3 days on which the human subject was administered 15 mg of prednisolone or prednisone, and administration of about 5 mg of prednisolone or prednisone per day to the patient, for 3 consecutive days (e.g., immediately) following the 3 days on which the patient was administered 10 mg of prednisolone or prednisone.

In some embodiments, the second tapering dose of prednisolone or prednisone includes administration of about 30 mg of prednisolone or prednisone per day to the patient, for 7 consecutive days immediately following completion of the initial course of prednisolone or prednisone, administration of about 20 mg of prednisolone or prednisone per day to the patient, for 7 consecutive days immediately following the 7 days on which the patient was administered 30 mg of prednisolone or prednisone, administration of about 15 mg of prednisolone or prednisone per day to the patient, for 5 consecutive days immediately following the 7 days on which the patient was administered 20 mg of prednisolone or prednisone, administration of about 10 mg of prednisolone or prednisone per day to the patient, for 5 consecutive days immediately following the 5 days on which the patient was administered 15 mg of prednisolone or prednisone, and administration of about 5 mg of prednisolone or prednisone per day to the patient, for 5 consecutive days immediately following the 5 days on which the patient was administered 10 mg of prednisolone or prednisone.

In some embodiments, the course of prednisolone or prednisone is administered after detecting an indication of an immune reaction in the patient, following administration of the AAV particles. In some embodiments, the course of prednisolone or prednisone is administered after detecting an indication of liver inflammation in the patient. For example, in some embodiments, the patient is monitored for liver inflammation following administration of the AAV particles, and the patient is administered a course of prednisolone or prednisone upon detecting liver inflammation.

In some embodiments, a rapid or large decrease in Factor VIII expression or Factor VIII activity in the blood stream of the patient indicates liver inflammation in the subject. In some embodiments, it is possible that an early peak of Factor VIII activity may be observed followed by a small and/or gradual decrease, after which the Factor VIII protein may be made at a somewhat lower level, which does not require administration of a course of prednisolone or prednisone. For example, in some embodiments, the amount of Factor VIII (e.g., a Factor VIII titer or Factor VIII activity level) in the patientblood stream is monitored following administration of the AAV particles, and the subject is administered a course of prednisolone or prednisone if a rapid or large decrease in the amount of Factor VIII (e.g., more than a threshold decrease in the Factor VIII titer or Factor VIII activity level, as compared to a level in the patient blood stream following administration of the AAV particles) is detected.

In some embodiments, an increase in the level of liver enzymes in the patient indicates liver inflammation in the subject. For example, in some embodiments, the level of liver enzymes in the patient is monitored following administration of the AAV particles, and the subject patient is administered a course of prednisolone or prednisone if an increase in the level of liver enzymes (e.g., more than a threshold increase in the amount of liver enzymes, e.g., as compared to a baseline level of liver enzymes in the patient before administration of the AAV particles or shortly after administration of the AAV particles) is detected.

Post-Administration Monitoring

In some embodiments, methods are provided for monitoring a patient for adverse reactions and/or treatment efficacy, following administration of adeno-associated virus (AAV) particles with a polynucleotide encoding a Factor VIII polypeptide, e.g., polynucleotides having high sequence identity to SEQ ID NO: 1 (CS04-FL-NA). In some embodiments, the patient is monitored for one or more of (a) an indication of liver inflammation (e.g., via rapid or large decreases in Factor VIII levels (e.g., titer or activity) and/or increases in liver enzymes (e.g., titer or activity)), (b) an increase in Factor VIII inhibitor antibodies in the patient s blood stream, (c) an increase in capsid proteins in the patient's blood stream, (d) an increase in anti-capsid protein antibodies in the patient s blood stream, and (e) an increase in polynucleotides, or fragments thereof, encoding the Factor VIII polypeptide in the patient s blood stream. In some embodiments, the subject is further treated upon detection of one or more adverse reaction and/or inefficacy of the treatment.

For example, in one embodiment, a method is provided for monitoring the efficacy of Factor VIII gene therapy of hemophilia A using adeno-associated virus (AAV) particles that include a polynucleotide encoding a Factor VIII polypeptide. The method includes determining whether Factor VIII inhibitor antibodies are present in the blood stream of the patient (e.g., in a blood sample collected from the patient) after administration of the AAV particles to the patient. In some embodiments, when Factor VIII inhibitor antibodies are detected in the blood stream of the patient (e.g., when an increase in the level of Factor VIII inhibitor antibodies is detected, as compared to a level in the patient prior to administration of the AAV particles), the method includes administering an alternative agent for treatment of hemophilia A to the patient.

In some embodiments, the alternative agent for treatment of hemophilia A is an alternative form of Factor VIII (e.g., one that does not include, or masks, one of more epitopes targeted by the detected Factor VIII inhibitor antibodies). In some embodiments, the alternative form of Factor VIII is a chemically-modified Factor VIII protein (e.g., a chemically-modified human or porcine Factor VIII protein). In some embodiments, the alternative form of Factor VIII is a Factor VIII protein derived from a non-human Factor VIII protein, e.g., a porcine Factor VIII protein. In some embodiments, the alternative agent for treatment of hemophilia A is a Factor VIII bypass therapy, e.g., a therapeutic agent that includes Factor II, Factor IX, and Factor X. For example, in some embodiments, the Factor VIII bypass therapy is a Factor VIII Inhibitor Bypass Activity (FEIBA) complex, recombinant activated factor VII (FVIIa), a prothrombin complex concentrate, or an activated prothrombin complex concentrate.

In one embodiment, a method is provided for monitoring the level of polynucleotide encoding a Factor VIII polypeptide, or a fragment thereof, in the blood stream of the patient following administration of the AAV particles. In one embodiment, the method includes administering to a hemophilia A patient a dose of adeno-associated virus (AAV) particles per kilogram body weight of the patient, where the AAV particles include a polynucleotide encoding a Factor VIII protein at a first time point. The method also includes measuring the level polynucleotide encoding the Factor VIII protein, or fragments thereof, in the patient's blood stream at a later time point, where the later time point is 7 days or longer. In one embodiment, the method includes administering to a hemophilia A patient a dose of 2×10 adeno-associated virus (AAV) particles per kilogram body weight of the patient, where the AAV particles include a polynucleotide having a nucleic acid sequence of SEQ ID NO: 1 (CS04-FL-NA) at a first time point. The method also includes measuring the level nucleic acids of SEQ ID NO: 1, or fragments thereof, in the patient's blood stream at a later time point, where the later time point is 7 days or longer. In one embodiment, the method includes administering to a hemophilia A patient a dose of 6×10 adeno-associated virus (AAV) particles per kilogram body weight of the patient, where the AAV particles include a polynucleotide having a nucleic acid sequence of SEQ ID NO: 1 (CS04-FL-NA) at a first time point. The method also includes measuring the level nucleic acids of SEQ ID NO: 1, or fragments thereof, in the patient's blood stream at a later time point, where the later time point is 7 days or longer. In some embodiments of the method, the later time point is at least 14 days later or at least 21 days later. In some embodiments, the later time point is at 7 days, 14 days, or 21 days after administration of the AAV particles.

In one embodiment, a method is provided for monitoring the level of capsid protein in the blood stream of the patient following administration of the AAV particles. In one embodiment, the method includes administering to a hemophilia A patient a dose of 2×10 adeno-associated virus (AAV) particles per kilogram body weight of said patient, where the AAV particles include a capsid protein and a polynucleotide that includes a nucleic acid sequence of SEQ ID NO: 1 (CS04-FL-NA) at a first time point. The method also includes measuring the level of the capsid protein in said patient's blood stream at a later time point, where the later time point is 7 days or longer. In one embodiment, the method includes administering to a hemophilia A patient a dose of 6×10 adeno-associated virus (AAV) particles per kilogram body weight of the patient, where the AAV particles include a capsid protein and a polynucleotide that includes a nucleic acid sequence of SEQ ID NO: 1 (CS04-FL-NA) at a first time point. The method also includes measuring the level of the capsid protein in said patient's blood stream at a later time point, where the later time point is 7 days or longer. In one embodiment, the method includes administering to a hemophilia A patient a dose of adeno-associated virus (AAV) particles per kilogram body weight of said patient, where the AAV particles include a capsid protein and a polynucleotide that encodes a Factor VIII protein at a first time point. The method also includes measuring the level of the capsid protein in said patient's blood stream at a later time point, where the later time point is 7 days or longer. In some embodiments of the method, the later time point is at least 14 days later or at least 21 days later. In some embodiments, the later time point is at 7 days, 14 days, or 21 days after administration of the AAV particles.

In one embodiment, a method is provided for monitoring the level of Factor VIII inhibitor antibodies in the blood stream of the patient following administration of the AAV particles. In one embodiment, the method includes administering to a hemophilia A patient a dose of 2×10 adeno-associated virus (AAV) particles per kilogram body weight of the patient, where the AAV particles include a polynucleotide that includes a nucleic acid sequence of SEQ ID NO: 1 (CS04-FL-NA) at a first time point. The method also includes measuring the level of anti-Factor VIII antibodies in the patient's blood stream at a later time point, wherein the later time point is 7 days or longer. In one embodiment, the method includes administering to a hemophilia A patient a dose of 6×10 adeno-associated virus (AAV) particles per kilogram body weight of the patient, where the AAV particles include a polynucleotide that includes a nucleic acid sequence of SEQ ID NO: 1 (CS04-FL-NA) at a first time point. The method also includes measuring the level of anti-Factor VIII antibodies in the patient's blood stream at a later time point, wherein said later time point is 7 days or longer. In one embodiment, the method includes administering to a hemophilia A patient a dose of adeno-associated virus (AAV) particles, where the AAV particles include a polynucleotide that encodes a Factor VIII protein at a first time point. The method also includes measuring the level of anti-Factor VIII antibodies in the patient's blood stream at a later time point, wherein said later time point is 7 days or longer. In some embodiments of the method, the later time point is at least 14 days later or at least 21 days later. In some embodiments, the later time point is at 7 days, 14 days, or 21 days after administration of the AAV particles.

In one embodiment, a method is provided for monitoring the level of anti-capsid protein antibodies in the blood stream of the subject following administration of the AAV particles. In one embodiment, the method includes administering to a hemophilia A patient a dose of 2×10 adeno-associated virus (AAV) particles per kilogram body weight of said patient, where the AAV particles include a capsid protein and a polynucleotide that includes a nucleic acid sequence of SEQ ID NO: 1 (CS04-FL-NA) at a first time point. The method also includes measuring the level of anti-capsid protein antibodies in the patient's blood stream at a later time point, where the later time point is 7 days or longer. In one embodiment, the method includes administering to a hemophilia A patient a dose of 6×10 adeno-associated virus (AAV) particles per kilogram body weight of the patient, where the AAV particles include a capsid protein and a polynucleotide that includes a nucleic acid sequence of SEQ ID NO: 1 (CS04-FL-NA) at a first time point. The method also includes measuring the level of anti-capsid protein antibodies in said patient's blood stream at a later time point, where the later time point is 7 days or longer. In one embodiment, the method includes administering to a hemophilia A patient a dose of adeno-associated virus (AAV) particles per kilogram body weight of the patient, where the AAV particles include a capsid protein and a polynucleotide that encodes a Factor VIII protein at a first time point. The method also includes measuring the level of anti-capsid protein antibodies in said patient's blood stream at a later time point, where the later time point is 7 days or longer. In some embodiments of the method, the later time point is at least 14 days later or at least 21 days later. In some embodiments, the later time point is at 7 days, 14 days, or 21 days after administration of the AAV particles.

IV. EXAMPLES

Example 1

Construction of a Codon Altered Factor VIII Variant Expression Sequence

Two hurdles had to be overcome in order to create a Factor VIII coding sequence that is effective for gene therapy of hemophilia A. First, because of the genomic size limitations of conventional gene therapy delivery vectors (e.g., AAV virions), the encoded Factor VIII polypeptide had to be shortened considerably. Second, the coding sequence had to be altered to: (i) stabilize packaging interactions within the delivery vector, (ii) stabilize the mRNA intermediary, and (iii) improve the robustness of transcription/translation of the mRNA.

To achieve the first objective, Applicants started with a B-domain deleted Factor VIII variant construct, referred to herein as "FVIII-BDD-SQ." In this construct, the B-domain is replaced with a fourteen amino acid sequence referred to as the "SQ" sequence. Recombinant FVIII-BDD-SQ is sold under the trade name REFACTO®, and has been shown to be effective for the management of hemophilia A. However, the native coding sequence for FVIII-BDD-SQ, which includes human wild-type nucleic acid sequences for the Factor VIII heavy and light chains, is ineffectively expressed in gene therapy vectors.

To address the poor expression of the native FVIII-BDD-SQ, the codon optimization algorithm described in Fath et al. (PLoS ONE, 6:e17596 (2011)), modified as described in Ward et al. (Blood, 117:798 (2011)) and in McIntosh et al. (Blood, 121, 3335-3344 (2013)) was applied to the FVIII-BDD-SQ sequence to create first intermediate coding sequence CS04a. However, Applicants recognized that the CS04a sequence created using the modified algorithm could be improved by further modifying the sequence. Accordingly, Applicants re-introduced CpG dinucleotides, re-introduced the CGC codon for arginine, changed the leucine and serine codon distributions, re-introduced highly conserved codon pairs, and removed cryptic TATA box, CCAAT box, and splice site elements, while avoiding CpG islands and local overrepresentation of AT-rich and GC-rich stretches.

First, the modified algorithm systematically replaces codons containing CpG-dinucleotides (e.g., arginine codons) with non-CpG-dinucleotide codons, and eliminates/avoids CpG-dinucleotides created by neighboring codons. This strict avoidance of CpG dinucleotides is usually done to prevent TLR-induced immunity after intramuscular injection of DNA vaccines. However, doing so limits the codon optimization possibilities. For example, the modified algorithm excludes use of the complete set of CGX arginine codons. This is particularly disruptive in the coding of genes for expression in human cells, because CGC is the most frequently used arginine codon in highly expressed human genes. Additionally, avoiding the creation of CpGs by neighboring codons further limits the optimization possibilities (e.g., limits the number of codon pairs that may be used together).

Because TLR-induced immunity is not expected to be a problem associated with liver-directed, AAV-based gene therapy, codons including CpGs, and neighboring codons creating CpGs, were re-introduced into intermediate coding sequence CS04a, preferentially in the sequence coding for the Factor VIII light chain (e.g., at the 3' end of the FVIII-BDD-SQ coding sequence). This allowed for more frequent use of preferred human codons, particularly those for arginine. Care was taken, however, to avoid creation of CpG islands, which are regions of coding sequence having a high frequency of CpG sites. This is contrary to the teachings of Krinner et al. (Nucleic Acids Res., 42(6):3551-64 (2014)), which suggests that CpG domains downstream of transcriptional start sites promote high levels of gene expression.

Second, the modified algorithm applies certain codons exclusively, such as CTG for leucine, GTG for valine, and CAG for glutamine. However, this offends the principles of balanced codon use, for example, as proposed in Haas et al. (Current Biology, 6(3):315-24 (1996)). To account for the overuse of preferred codons by the modified algorithm, alternate leucine codons were re-introduced where allowed by the other rules applied to the codon alteration (e.g., CpG frequency and GC content).

Third, the modified algorithm replaces codon pairs without regard to how conserved they are in nature, when certain criteria (e.g., the presence of CG-dinucleotides) are met. To account for beneficial properties which may have been conserved by evolution, the most conserved codon pairs that were replaced by the algorithm and the most conserved preferred codon pairs, e.g., as described in Tats et al. (BMC Genomics 9:463 (2008)), were analyzed and adjusted where allowed by the other rules applied to the codon alteration (e.g., CpG frequency and GC content).

Fourth, serine codons used in the intermediate coding sequence were also re-engineered. Specifically, AGC, TCC, and TCT serine codons were introduced into the modified coding sequence with higher frequency, to better match overall for human codon usage (Haas et al., supra).

Fifth, TATA box, CCAAT box elements, and intron/exon splice sites were screened and removed from the modified coding sequence. When modifying the coding sequence, care was taken to avoid local overrepresentation of AT-rich or GC rich stretches.

Finally, in addition to optimizing the codon usage within the coding sequence, the structural requirements of the underlying AAV virion were considered when further refining the intermediate coding sequence CS04a. AAV vectors (e.g., the nucleic acid portion of an AAV virion) are packaged as single stranded DNA molecules into their capsids (for review, see, Daya and Berns, Clin. Microbiol Rev., 21(4):583-93 (2008)). The GC content of the vector is therefore likely to influence packaging of the genome and, thus, vector yields during production. Like many algorithms, the modified algorithm used here creates an optimized gene sequence with a GC content of at least 60% (see, Fath et al., PLoS One, 6(3):e17596 (2011) (erratum in: PLoS One, (6)3 (2011)). However, the AAV8 capsid protein is encoded by a nucleotide sequence having a lower GC content of about 56%. Thus, to better mimic the native AAV8 capsid protein coding sequence, the GC content of the intermediate coding sequence CS04a was reduced to 56%.

The resulting CS04 coding sequence, shown in FIG. 2, has an overall GC content of 56%. The CpG-dinucleotide content of the sequence is moderate. However, CpG dinucleotides are predominantly in the downstream portion of the coding sequence, e.g., the portion coding for the Factor VIII light chain. The CS04 sequence has 79.77% nucleotide sequence identity to the corresponding coding sequences in wild-type Factor VIII (Genbank accession M14113).

For comparison purposes, several other codon-optimized, ReFacto constructs were prepared. The CS08 ReFacto construct was codon-optimized as described in Radcliff P. M. et al., Gene Therapy, 15:289-97 (2008), the content of which is hereby expressly incorporated by reference herein, in its entirety, for all purposes. The CS10 codon-optimized ReFacto construct was obtained from Eurofins Genomics (Ebersberg, Germany). The CS11 codon-optimized ReFacto construct was obtained from Integrated DNA Technologies, Inc. (Coralville, USA). The CH25 codon-optimized ReFacto construct was obtained from ThermoFischer Scientific's GeneArt services (Regensburg, Germany). The CS40 ReFacto construct consists of the wild type Factor VIII coding sequence. The sequence identities shared between each of the ReFacto coding sequences is shown in Table 2, below.

TABLE 2

Percent identity matrix for codon-altered Factor VIII constructs.

|  | CS04 | CS08 | CS10 | CS11 | CS40 | CH25 |
|---|---|---|---|---|---|---|
| CS04 | 100% |  |  |  |  |  |
| CS08 | 82.2% | 100% |  |  |  |  |
| CS10 | 79.4% | 78.4% | 100% |  |  |  |
| CS11 | 78.3% | 78.1% | 77.5% | 100% |  |  |
| CS40 | 79.8% | 76.7% | 77.6% | 75.4% | 100% |  |
| CH25 | 85.1% | 85.0% | 79.9% | 79.4% | 75.8% | 100% |

Figure 14:
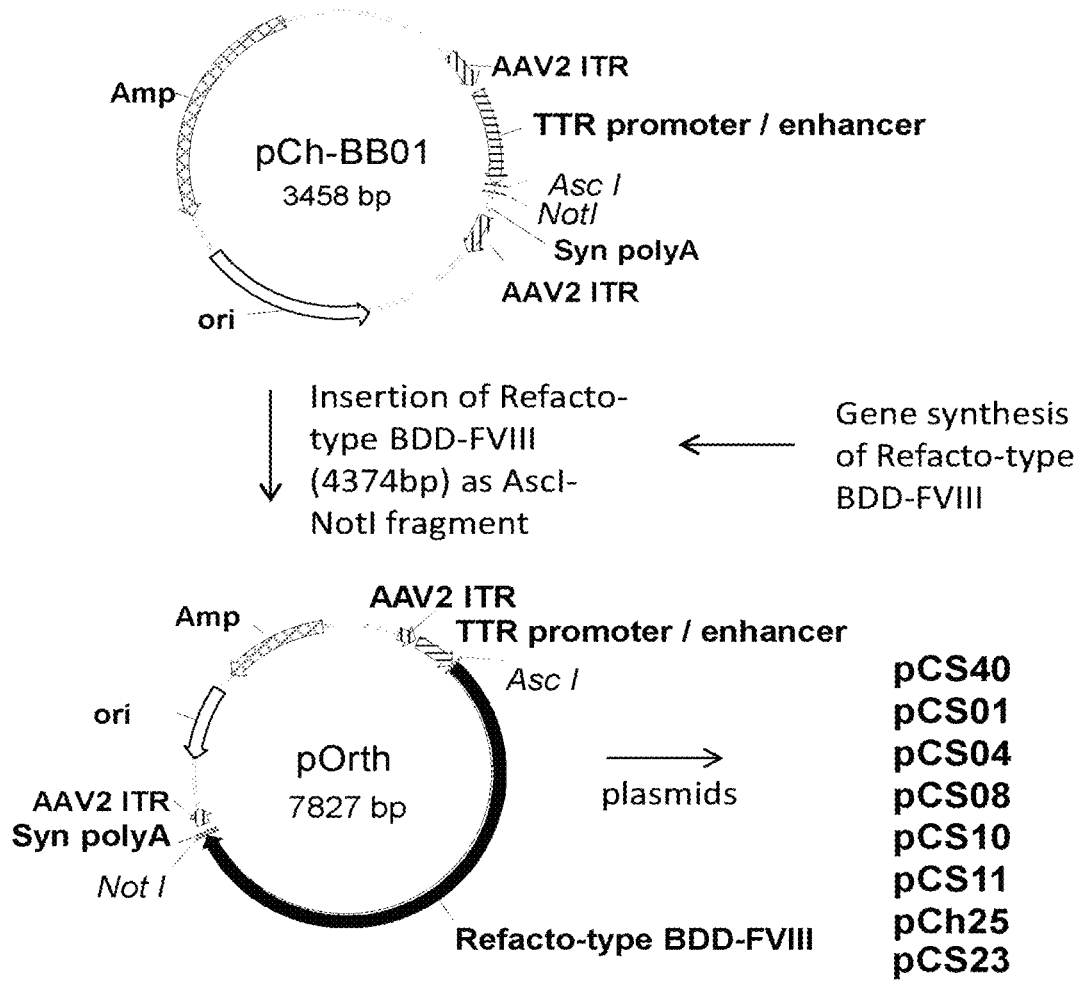
FIG. 14 illustrates the scheme for cloning the pCS40, pCS04, pCS08, pCS10, pCS11, and pCh25 constructs, by inserting synthetic Refacto-type BDD-FVIII DNA sequences into the vector backbone pCh-BB01 via AscI and NotI restriction sites.

Plasmids of each construct were constructed by cloning different synthetic DNA fragments into the same vector backbone plasmid (pCh-BB01). DNA synthesis of the Refacto-type BDD-FVIII fragments with flanking AscI and NotI enzyme restriction sites were done by ThermoFischer Scientific (Regensburg, Germany). The vector backbone contains two flanking AAV2-derived inverted terminal repeats (ITRs) that encompass a promoter/enhancer sequence derived from the liver-specific murine transthyretin gene, AscI and NotI enzyme restriction sites for insertion of the respective Refacto-type BDD-FVIII and a synthetic polyA site. After ligation of the prepared vector backbone and inserts via the AscI and NotI sites, the resulting plasmids were amplified in milligram scale. The Refacto-type BDD-FVIII sequences of the constructs were verified by direct sequencing (Microsynth, Balgach, Switzerland). The cloning resulted in seven different plasmid constructs named pCS40, pCS04, pCS08, pCS10, pCS11, and pCh25 (FIG. 14). The constructs have the same vector backbone and encode the same B-domain deleted FVIII protein (Refacto-type BDD-FVIII), but differ in their FVIII coding sequence.

AAV8-based vectors were prepared by the three plasmid transfection method, as described in Grieger JC, et al. (Virus Vectors Using Suspension HEK293 Cells and Continuous Harvest of Vector From the Culture Media for GMP FIX and FLT1 Clinical Vector, Mol Ther., Oct 6. (2015) doi: 10.1038/mt.2015.187. [Epub ahead of print]), the content of which is hereby expressly incorporated by reference herein, in its entirety, for all purposes. HEK293 suspensions cells were used for plasmid transfections using the corresponding FVIII vector plasmid, the helper plasmid pXX6-80 (carrying adenoviral helper genes), and the packaging plasmid pGSK2/8 (contributing the rep2 and cap8 genes). To isolate the AAV8 constructs, the cell pellets of one liter cultures were processed using iodixanol gradients, as described in Grieger et al. (2015, Supra). The procedure resulted in vector preparations called vCS04, vCS08, vCS10, vCS11, and vCH25. Vectors were quantified by qPCR using the universal qPCR procedure targeting the AAV2 inverted terminal repeats (Aurnhammer, Human Gene Therapy Methods: Part B 23:18-28 (2012)). A control vector plasmid carrying AAV2 inverted terminal repeats served for preparing the standard curve. The resulting vCS04 construct is presented as SEQ ID NO: 8 in FIGS. 7A-7C.

Figure 15:
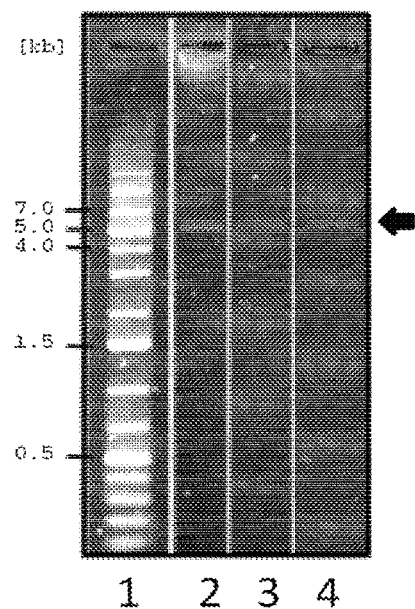

The integrity of the vector genomes was analyzed by AAV agarose gel electrophoresis. The electrophoresis was performed as described in Fagone et al., Human Gene Therapy Methods 23:1-7 (2012). Briefly, AAV vector preparations were incubated at 75° C. for 10 minutes in the presence of 0.5% SDS and then cooled down to room temperature. Approximately 1.5E10 vector genomes (vg) were loaded per lane on a 1% 1×TAE agarose gel and electrophoresed for 60 min at 7 V/cm of gel length. The gel was then stained in 2×GelRed (Biotium Cat#41003) solution and imaged by ChemiDocTMMP (Biorad). The results shown in FIG. 15 demonstrate that the vCS04 and vCS40 viral vectors have the same-sized genome, indicated by a distinct band in the 5kb range (FIG. 15, lanes 2-4). Despite a vector size of approx. 5.2 kb, the genome is a homogenous band confirming correct packaging of the somewhat oversized genome (relative to an AAV wild-type genome of 4.7 kb). All other vCS vector preparations show the same genomic size (data not shown).

Figure 16:
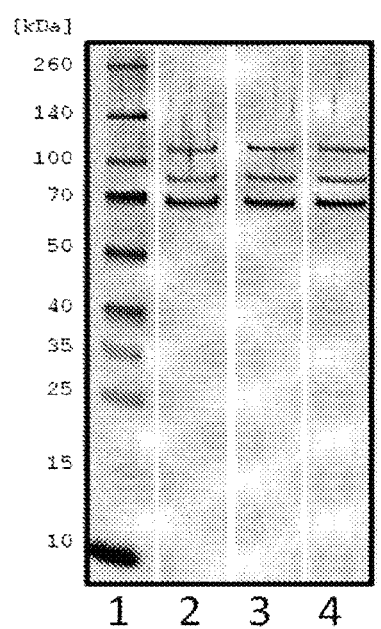

In order to confirm the expected pattern of capsid proteins, SDS PAGE followed by silver staining was performed with the vectors vCS04 and vCS40 (FIG. 16). As shown in the figure, the downstream purification procedure resulted in highly purified material displaying the expected protein pattern of VP1, VP2 and VP3 (FIG. 16, lanes 2-4). The same pattern was seen with all other viral preparations (not shown). The SDS-PAGE procedure of AAV preparations was done according to standard procedures. Each lane contained 1E10 vg of the respective viral construct, and were separated on a 4-12% Bis-Tris (NuPAGE® Novex, Life Technologies) gel as per manufacturer's instructions. Silver staining was performed with a SilverQuest™ kit (Novex, Life Technologies) according to the manufacturer's instructions.

Surprisingly, AAV vector vCS04 had higher virion packaging, measured by higher yields in AAV virus production, as compared to the vCS40 wild-type coding construct and the other codon-optimized constructs. As shown in Table 3, the vCS04 vector replicated substantially better than vCS40, providing a 5-7 fold yield increase in AAV titer.

TABLE 3

Yields per liter cell culture obtained with AAV vector constructs vCS04 and vCD40, as purified from cell pellets.

| Construct | Vector concentration [vg/ml] ×10E12 | Yields [vg/liter] ×10E12 | Fold increase vs wt |
| --- | --- | --- | --- |
| vCS40 | 2.0 | 11.0 | — |
| vCS04-Sample 1 | 17.6 | 79.2 | 7.2 |
| vCS04-Sample 2 | 15.9 | 58.8 | 5.4 |

Example 2

In Vivo Expression of Codon-Altered Factor VIII Variant Expression Sequences

To test the biological potency of the codon-altered Factor VIII variant sequences, the ReFacto-type FVIII constructs described in Example 1 were administered to mice lacking Factor VIII. Briefly, the assays were performed in C57B1/6 FVIII knock-out (ko) mice (with 6-8 animals per group) by tail vein injection of 4E12 vector genomes (vg) per kilogram body weight of mouse. Blood was drawn 14 days after injection by retroorbital puncture and plasma was prepared and frozen using standard procedures. Expression levels at day 14 were chosen because there is minimal influence of inhibitory antibodies at this time, which are seen in some animals of this mouse model at later times. FVIII activity in the mouse plasma was determined using the Technochrome FVIII assay performed, with only minor modifications, as suggested by the manufacture (Technoclone, Vienna, Austria). For the assay, the plasma samples were appropriately diluted and mixed with assay reagents, containing thrombin, activated factor IX (FIXa), phospholipids, factor X and calcium. Following FVIII activation by thrombin a complex with FIXa, phospholipids and calcium is formed. This complex activates FX to activated FX (FXa) which in turn cleaves para-nitroanilide (pNA) from the chromogenic substrate. The kinetics of pNA formation is measured at 405 nm. The rate is directly proportional to the FVIII concentration in the sample. FVIII concentrations are read from a reference curve and results are given in IU FVIII/milliliter.

The results, presented in Table 4 below, demonstrate that the codon-altered sequences designed using commercial algorithms (CS10, CS11, and CH25) provided only a modest increase in BDD-Factor VIII (3-4 fold) as compared to the wild-type BDD-Factor VIII construct (CS40). Similarly, the codon-altered BDD-Factor VIII construct prepared as described in Radcliffe et al. (CS08), only provided a 3-4 fold increase in BDD-FVIII expression. This result is consistent with the results reported in Radcliff et al. Surprisingly, the CS04 construct provided much higher BDD-FVIII expression in the in-vivo biopotency assays (e.g., a 74-fold increase).

TABLE 4

Expression of FVIII in the plasma of FVIII-knock-out mice induced by the different AAV vector constructs.

| Construct | Codon Algorithm | Average FVIII Expression at Day 14 [IU/ml] | Standard deviation | Number of mice | Fold increase vs wt |
| --- | --- | --- | --- | --- | --- |
| vCS40 | Human wild-type | 0.03 | 0.03 | 12 | — |
| vCS04 | Applicants' | 2.21 | 1.20 | 55 | 73.7 |
| vCS08 | Radcliffe et al. | 0.11 | 0.01 | 6 | 3.6 |
| vCS10 | Eurofins | 0.09 | 0.01 | 7 | 3.0 |
| vCS11 | IDT | 0.08 | 0.02 | 8 | 2.7 |
| vCH25 | GeneArt | 0.13 | 0.12 | 18 | 4.3 |

Example 3

Non-Clinical Efficacy and Toxicology Evaluation of a Human FVIII Gene Therapy Vector in Mice Hemophilia A is an inherited bleeding disorder caused by missing or defective factor VIII (FVIII) and treated with plasma-derived or recombinant factor concentrates. These concentrates need to be infused on a regular basis to maintain adequate FVIII levels to control and prevent bleeding events. Given the challenges of protein replacement therapy, gene therapy may offer an alternative therapeutic approach for patients with hemophilia A. By introducing a functional F8 gene copy into the target hepatic cells to induce endogenous FVIII expression, frequent infusions of clotting factor may no longer be necessary.

Adeno-associated virus (AAV)-based gene therapy has the potential to provide clinical benefit in patients with hemophilia A. A recombinant (r)AAV8-based gene therapy vector containing the CS04 Factor VIII codon optimized construct is designed to deliver a human codon-optimized B-domain-deleted FVIII (BDDFVIII) transgene under the control of a liver-specific transthyretin promoter. This construct was used to examine the dose-response relationship for FVIII activity in F8 knockout (ko) mice and to evaluate toxicity following a single intravenous administration.

Briefly, to test the efficacy of the treatment, 12 male FVIII knock-out mice per group were administered a single intravenous dose of $3.0 \times 10^{11}$, $1.2 \times 10^{12}$, or $3.0 \times 10^{12}$ of the vector capsid particles (cp)/kg or 10 mL/kg buffer. Retro-orbital blood samples were taken every other week over 8 weeks and analyzed for FVIII using a chromogenic assay. The plasma samples obtained from the final in-life blood sampling were also used for the analysis of FVIII binding and neutralizing antibodies. At the end of the observation period, hemostatic control was assessed using a tail-tip bleeding assay.

Figure 17:
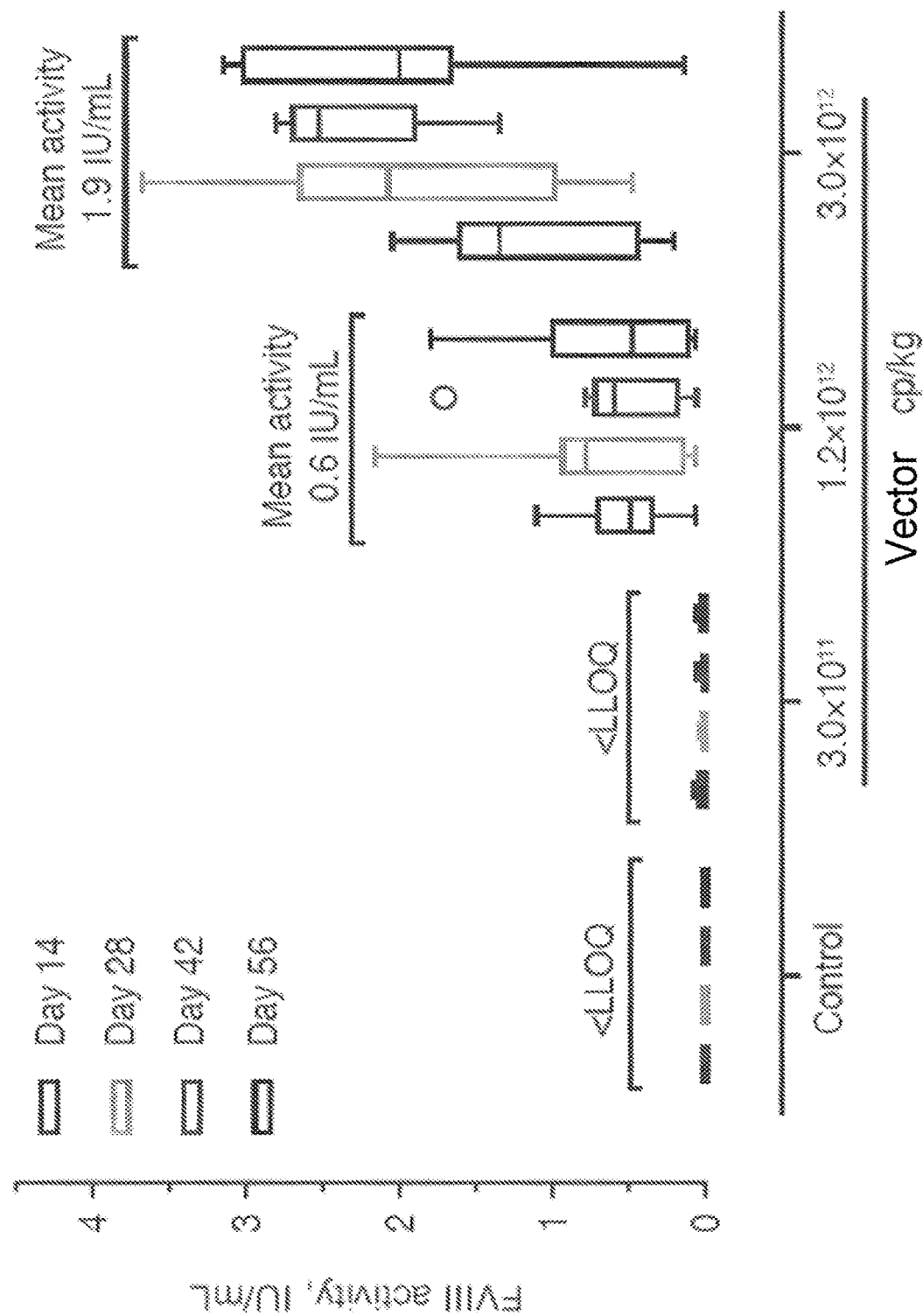

At study end, all samples were negative for anti-BDD-FVIII binding antibodies with the exception of 4 animals (treated with $3.0 \times 10^{12}$ cp/kg vector) that tested positive for binding and neutralizing antibodies. These animals were excluded from statistical analysis of FVIII activity levels and blood loss in the tail-tip bleeding assay. The administration of $1.2 \times 10^{12}$ or $3.0 \times 10^{12}$ cp/kg vector resulted in a dose-dependent increase in mean plasma FVIII activity to 0.6 and 1.9 IU/mL, respectively, calculated over the period of investigation, but FVIII activity was below the lower limit of quantification (LLOQ) in mice treated with buffer or $3.0 \times 10^{11}$ cp/kg vector (FIG. 17).

Figure 18:
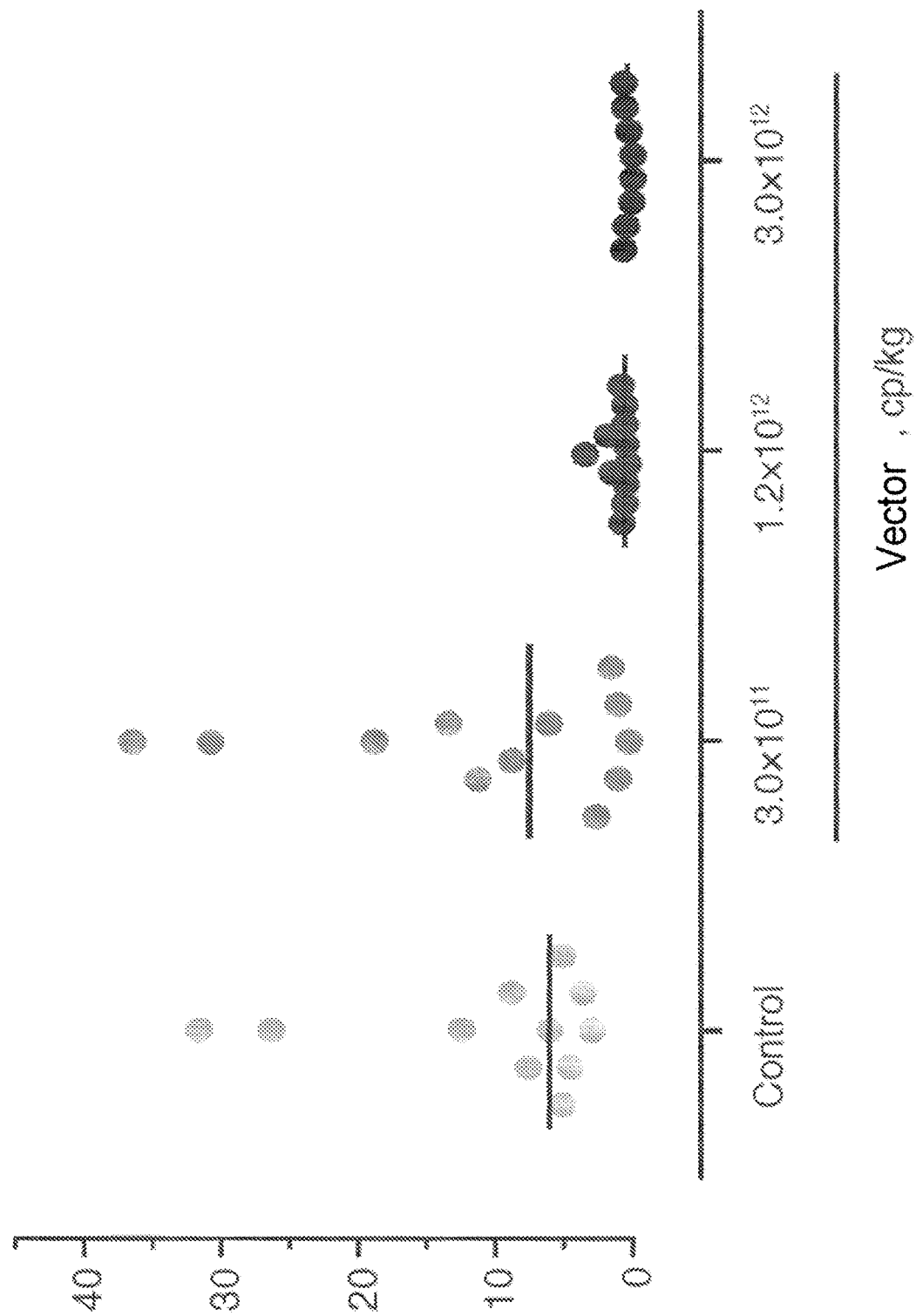

Efficacy was assessed in a tail-tip bleeding assay on Day 63. Blood loss over 60 minutes in mg/g body weight is presented in FIG. 18. Animals treated with buffer or $3.0 \times 10^{11}$ cp/kg of the gene therapy vector showed similar blood loss (6.1 mg/g and 7.5 mg/g, respectively), consistent with the absence of detectable FVIII activity. Higher doses of the gene therapy vector significantly reduced blood loss in a dose-dependent manner ($1.2 \times 10^{12}$: 0.6 mg/g, $3.0 \times 10^{12}$: 0.4 mg/g; Jonckheere-Terpstra test: 1-sided P value <0.001).

To test the toxicology of the construct, Male C57BL/6J mice (n=20/group) were intravenously injected with a single bolus dose of $1 \times 10^{13}$, $3 \times 10^{13}$, or $5 \times 10^{13}$ cp/kg vector or formulation buffer (Table 5). Assessment of toxicity was based on clinical signs, body weight, food consumption, ophthalmology, and clinical and anatomical pathology. Complete necropsies were performed on 5 animals from each cohort, and macroscopic findings, organ weights, and the results of microscopic examinations were recorded. Tissues were collected for biodistribution assessment by quantitative polymerase chain reaction from a further 5 animals from each cohort. Blood was collected before dosing and at necropsy. FVIII activity, BDD-FVIII antigen, binding anti-BDD-FVIII antibodies, neutralizing anti-BDD-FVIII antibodies, and binding anti-AAV8 antibodies were analyzed.

TABLE 5

Design of the toxicity study.

| Test item | Dose cp/mg | Group size | | |
|---|---|---|---|---|
| | | Termination Day 3 | Termination Week 3 | Termination Week 18 |
| Buffer (controls) | 0 | 20 | 20 | 20 |
| vCS04 | $1 \times 10^{13}$ | 20 | 20 | 20 |
| vCS04 | $3 \times 10^{13}$ | 20 | 20 | 20 |
| vCS04 | $5 \times 10^{13}$ | 20 | 20 | 20 |

It was found that a single intravenous bolus administration of the gene therapy vector at up to $5 \times 10^{13}$ cp/kg was well tolerated. No deaths occurred during the study and no clinical signs or post-dosing observations were considered to be related to administration of the vector. No negative ophthalmic findings were observed. No effects on body weight or food consumption were observed. No changes in clinical chemistry, hematology, or urinalysis parameters were observed. And no toxicologically relevant macroscopic or microscopic findings were related to the administration of the gene therapy vector.

Figure 19A:
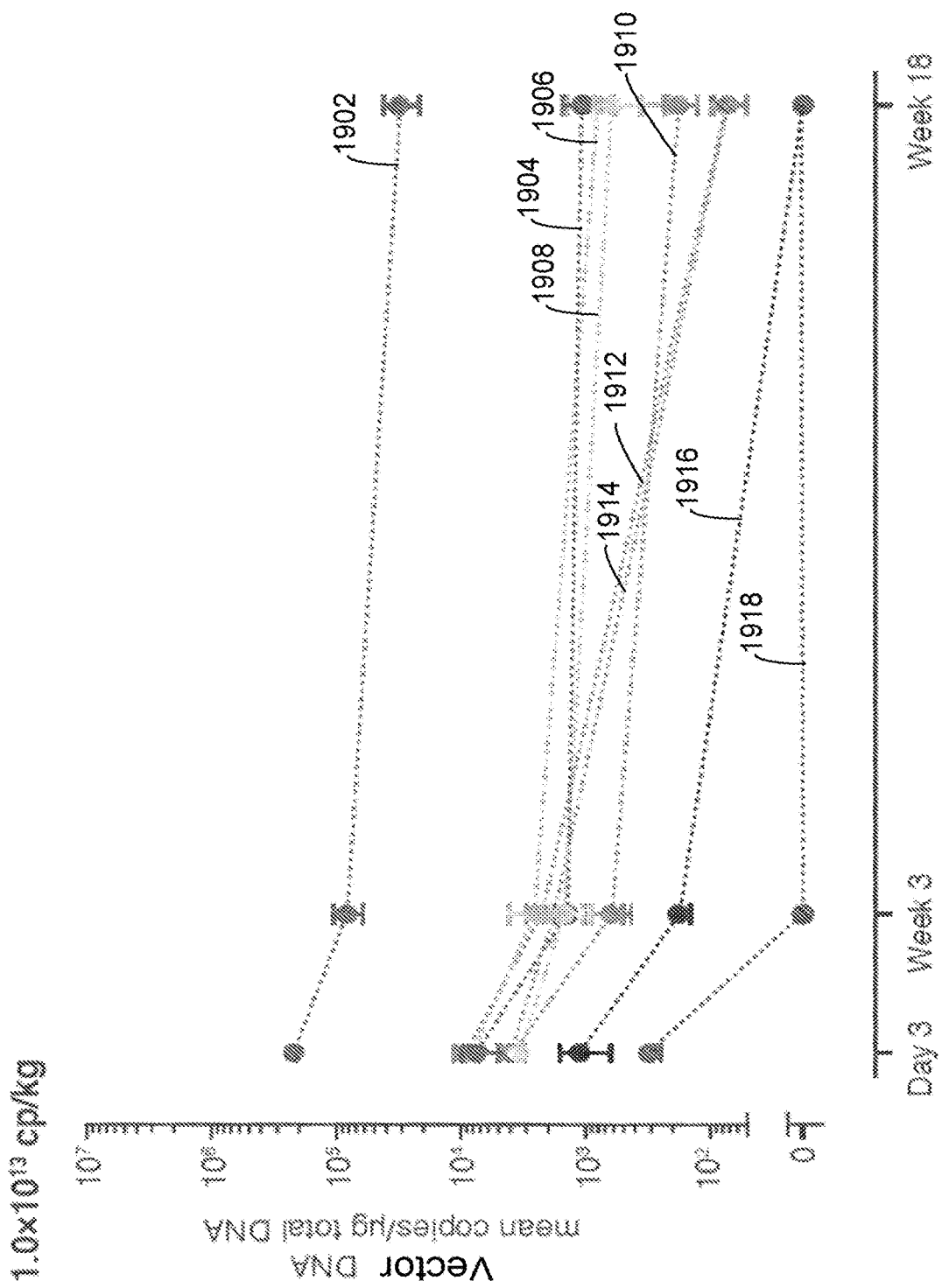
Figure 19B:
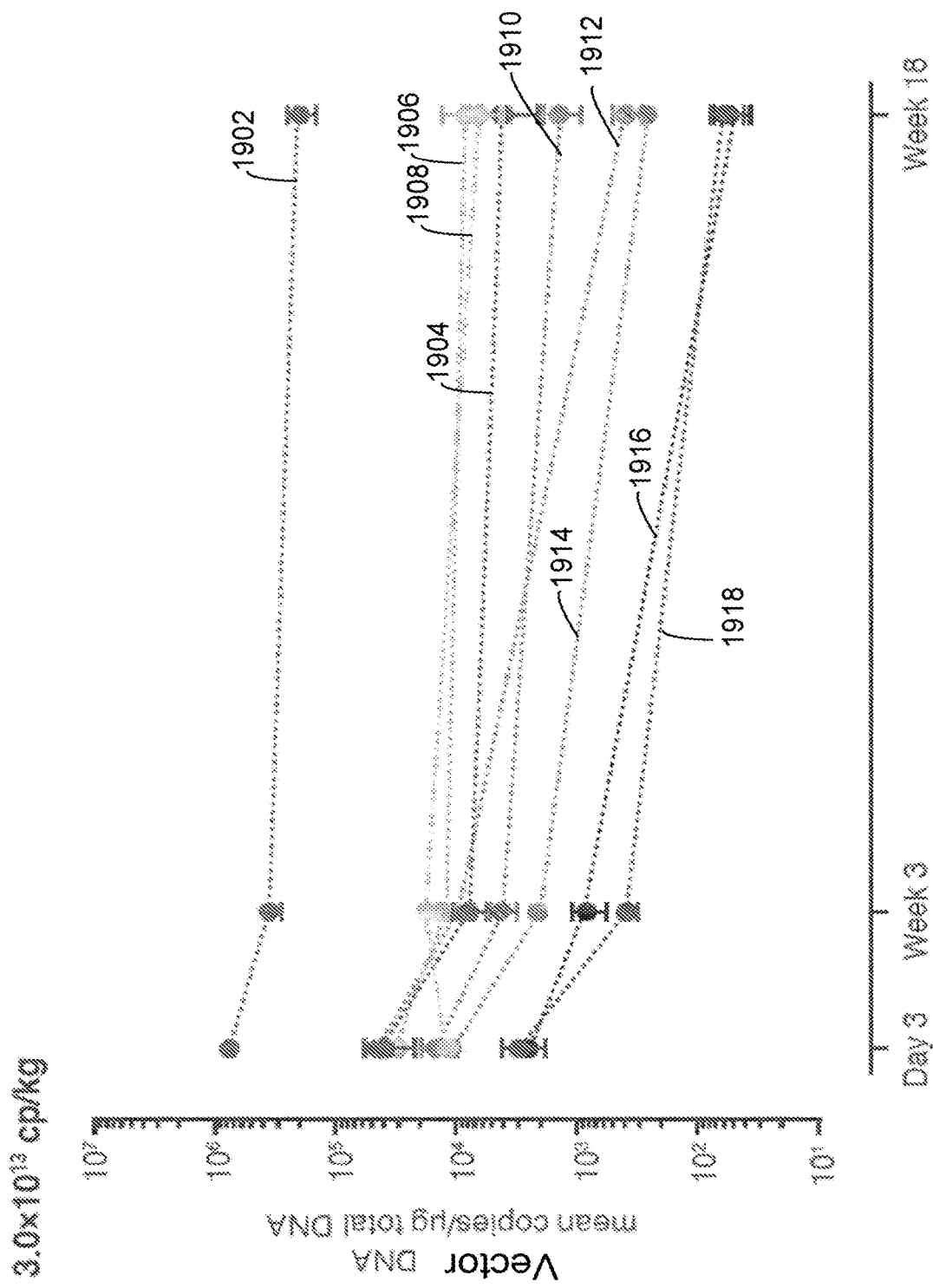
Figure 19C:
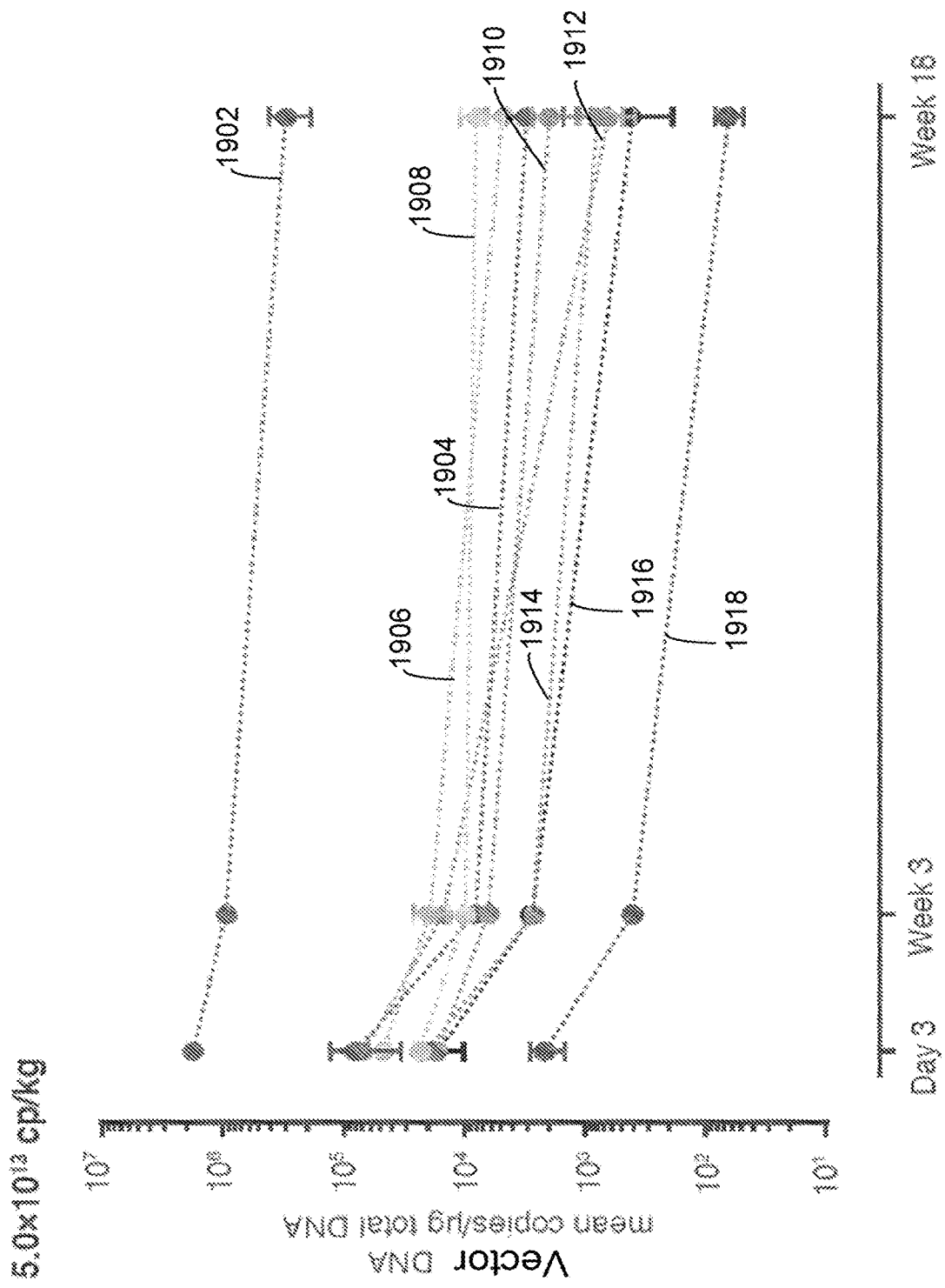

FVIII activity and BDD-FVIII antigen evaluations were prone to wide variability, most likely as a result of the generation of neutralizing antibodies to human BDD-FVIII. However, individual animals in all vector groups had activities above the general baseline levels at Day 3 and Weeks 3 and 18 (data not shown). In the harvested tissue samples, vector DNA was detected predominantly in the liver. Biodistribution to the liver and other tissues was dose related, and was generally highest at the earliest time point, and decreased over time. The presence of vector DNA in brain and testis decreased significantly over time and, in many animals, was below the LLOQ of the assay by Week 18 (FIG. 19).

Taken together, there results show that the codon-optimized BDD-FVII gene therapy is efficacious when administered to FVIII knock-out mice at doses ≥$1.2 \times 10^{12}$ cp/kg. The no-observed-adverse-effect level was considered to be $5.0 \times 10^{13}$ cp/kg, the highest dose tested in the toxicity study.

In some embodiments, dosages administered to mice can be converted to human dosages according to the guidance provided in "Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), July 2005, Pharmacology and Toxicology, the content of which is hereby incorporated by reference, in its entirety, for all purposes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

<160> NUMBER OF SEQ ID NOS: 15

<210> SEQ ID NO 1
<211> LENGTH: 4374

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

| | | | | | | |
|---|---|---|---|---|---|---|
| atgcagattg | agctgagcac | ctgcttcttc | ctgtgcctgc | tgaggttctg | cttctctgcc | 60 |
| accaggagat | actacctggg | ggctgtggag | cttctttggg | actacatgca | gtctgacctg | 120 |
| ggggagctgc | ctgtggatgc | caggttccca | cccagagtgc | ccaaatcctt | cccattcaac | 180 |
| acctctgtgg | tctacaagaa | gaccctcttt | gtggagttca | ctgaccacct | gttcaacatt | 240 |
| gccaaaccca | ggccaccctg | gatgggactc | ctgggaccca | ccattcaggc | tgaggtgtat | 300 |
| gacactgtgg | tcatcaccct | caagaacatg | gcctcccacc | ctgtgagcct | gcatgctgtg | 360 |
| ggggtcagct | actggaaggc | ctctgagggg | gctgagtatg | atgaccagac | ctcccagagg | 420 |
| gagaaggagg | atgacaaagt | gttccctggg | ggcagccaca | cctatgtgtg | gcaggtcctc | 480 |
| aaggagaatg | gccccatggc | ctctgaccca | ctctgcctga | cctactccta | cctttctcat | 540 |
| gtggacctgg | tcaaggacct | caactctgga | ctgattgggg | ccctgctggt | gtgcagggag | 600 |
| ggctccctgg | ccaaagagaa | gacccagacc | tgcacaagt | tcattctcct | gtttgctgtc | 660 |
| tttgatgagg | gcaagagctg | gcactctgaa | accaagaact | ccctgatgca | ggacagggat | 720 |
| gctgcctctg | ccagggcctg | gcccaagatg | cacactgtga | atggctatgt | gaacaggagc | 780 |
| ctgcctggac | tcattggctg | ccacaggaaa | tctgtctact | ggcatgtgat | tggcatgggg | 840 |
| acaacccctg | aggtgcactc | cattttcctg | gagggccaca | ccttcctggt | caggaaccac | 900 |
| agacaggcca | gcctggagat | cagcccccatc | accttcctca | ctgcccagac | cctgctgatg | 960 |
| gacctcggac | agttcctgct | gttctgccac | atcagctccc | accagcatga | tggcatggag | 1020 |
| gcctatgtca | aggtggacag | ctgccctgag | gagccacagc | tcaggatgaa | gaacaatgag | 1080 |
| gaggctgagg | actatgatga | tgacctgact | gactctgaga | tggatgtggt | ccgctttgat | 1140 |
| gatgacaaca | gccatccctt | cattcagatc | aggtctgtgg | ccaagaaaca | ccccaagacc | 1200 |
| tgggtgcact | acattgctgc | tgaggaggag | gactgggact | atgccccact | ggtcctggcc | 1260 |
| cctgatgaca | ggagctacaa | gagccagtac | ctcaacaatg | gcccacagag | gattggacgc | 1320 |
| aagtacaaga | aagtcaggtt | catggcctac | actgatgaaa | ccttcaagac | cagggaggcc | 1380 |
| attcagcatg | agtctggcat | cctgggccca | ctcctgtatg | ggaggtggg | ggacaccctg | 1440 |
| ctcatcatct | tcaagaacca | ggcctccagg | ccctacaaca | tctacccaca | tggcatcact | 1500 |
| gatgtcaggc | ccctgtacag | ccgcaggctg | ccaaaggggg | tgaaacacct | caaggacttc | 1560 |
| cccattctgc | ctggggagat | cttcaagtac | aagtggactg | tcactgtgga | ggatggacca | 1620 |
| accaaatctg | accccaggtg | cctcaccaga | tactactcca | gctttgtgaa | catggagagg | 1680 |
| gacctggcct | ctgcctgat | tggcccactg | ctcatctgct | acaaggagtc | tgtggaccag | 1740 |
| aggggaaacc | agatcatgtc | tgacaagagg | aatgtgattc | tgttctctgt | ctttgatgag | 1800 |
| aacaggagct | ggtacctgac | tgagaacatt | cagcgcttcc | tgcccaaccc | tgctggggtg | 1860 |
| cagctggagg | accctgagtt | ccaggccagc | aacatcatgc | actccatcaa | tggctatgtg | 1920 |
| tttgacagcc | tccagctttc | tgtctgcctg | catgaggtgg | cctactggta | cattctttct | 1980 |
| attggggccc | agactgactt | cctttctgtc | ttcttctctg | gctacacctt | caaacacaag | 2040 |
| atggtgtatg | aggacaccct | gacectcttc | ccattctctg | gggagactgt | gttcatgagc | 2100 |
| atggagaacc | ctggcctgtg | gattctggga | tgccacaact | ctgacttccg | caacaggggc | 2160 |

```
atgactgccc tgctcaaagt ctcctcctgt gacaagaaca ctggggacta ctatgaggac    2220
agctatgagg acatctctgc ctacctgctc agcaagaaca atgccattga gcccaggagc    2280
ttcagccaga atccacctgt cctgaaacgc caccagaggg agatcaccag gaccaccctc    2340
cagtctgacc aggaggagat tgactatgat gacaccattt ctgtggagat gaagaaagag    2400
gactttgaca tctatgacga ggacgagaac cagagcccaa ggagcttcca gaagaagacc    2460
aggcactact tcattgctgc tgtggagcgc ctgtgggact atggcatgag ctccagcccc    2520
catgtcctca ggaacagggc ccagtctggc tctgtgccac agttcaagaa agtggtcttc    2580
caagagttca ctgatggcag cttcacccag cccctgtaca gggggagct gaatgagcac    2640 ctgggactcc tgggcccata catcagggct gaggtggagg acaacatcat ggtgaccttc    2700
cgcaaccagg cctccaggcc ctacagcttc tacagctccc tcatcagcta tgaggaggac    2760
cagaggcagg gggctgagcc acgcaagaac tttgtgaaac ccaatgaaac caagacctac    2820
ttctggaaag tccagcacca catggccccc accaaggatg agtttgactg caaggcctgg    2880
gcctacttct ctgatgtgga cctggagaag gatgtgcact ctggcctgat tggcccactc    2940
ctggtctgcc acaccaacac cctgaaccct gcccatggaa ggcaagtgac tgtgcaggag    3000
tttgccctct tcttcaccat cttttgatgaa accaagagct ggtacttcac tgagaacatg    3060
gagcgcaact gcagggcccc atgcaacatt cagatggagg accccacctt caaagagaac    3120
taccgcttcc atgccatcaa tggctacatc atggacaccc tgcctgggct tgtcatggcc    3180
caggaccaga ggatcaggtg gtacctgctt tctatgggct ccaatgagaa cattcactcc    3240
atccacttct ctgggcatgt cttcactgtg cgcaagaagg aggagtacaa gatggcactg    3300
tacaacctct accctgggt ctttgagact gtggagatgc tgccctccaa agctggcatc    3360
tggagggtgg agtgcctcat tggggagcac ctgcatgctg catgagcac cctgttcctg    3420 gtctacagca acaagtgcca gaccccctg ggaatggcct ctggccacat cagggacttc    3480
cagatcactg cctctggcca gtatggccag tgggccccca agctggccag gctccactac    3540
tctggatcca tcaatgcctg gagcaccaag gagccattca gctggatcaa agtggacctg    3600
ctggccccca tgatcatcca tggcatcaag acccaggggg ccaggcagaa gttctccagc    3660
ctgtacatca gccagttcat catcatgtac agcctggatg caagaaatg gcagacctac    3720 agaggcaact ccactggaac actcatggtc ttctttggca atgtggacag ctctggcatc    3780
aagcacaaca tcttcaaccc cccaatcatc gccagataca tcaggctgca ccccacccac    3840
tacagcatcc gcagcaccct caggatggag ctgatgggct gtgacctgaa ctcctgcagc    3900
atgcccctgg gcatggagag caaggccatt tctgatgccc agatcactgc ctccagctac    3960
ttcaccaaca tgtttgccac ctggagccca agcaaggcca ggctgcacct ccagggaagg    4020
agcaatgcct ggaggcccca ggtcaacaac ccaaaggagt ggctgcaggt ggacttccag    4080
aagaccatga aggtcactgg ggtgaccacc aggggggtca gagcctgct caccagcatg    4140 tatgtgaagg agttcctgat cagctccagc aggatggcc accagtggac cctcttcttc    4200
cagaatggca aggtcaaggt gttccagggc aaccaggaca gcttcacccc tgtggtgaac    4260
agcctggacc cccccctcct gaccagatac ctgaggattc accccagag ctgggtccac    4320 cagattgccc tgaggatgga ggtcctggga tgtgaggccc aggacctgta ctga          4374
```

<210> SEQ ID NO 2
<211> LENGTH: 1457
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380
```

-continued

```
Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
            405                 410                 415

Leu Val Leu Ala Pro Asp Asp Arg Ser Tyr Lys Ser Gln Tyr Leu Asn
        420                 425                 430

Asn Gly Pro Gln Arg Ile Gly Arg Lys Tyr Lys Lys Val Arg Phe Met
    435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
```

-continued

```
                805                 810                 815
Gln Lys Lys Thr Arg His Tyr Phe Ile Ala Ala Val Glu Arg Leu Trp
                820                 825                 830

Asp Tyr Gly Met Ser Ser Pro His Val Leu Arg Asn Arg Ala Gln
            835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
            885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
            965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
        1010                1015                1020

Cys Arg Ala Pro Cys Asn Ile Gln Met Glu Asp Pro Thr Phe Lys
        1025                1030                1035

Glu Asn Tyr Arg Phe His Ala Ile Asn Gly Tyr Ile Met Asp Thr
        1040                1045                1050

Leu Pro Gly Leu Val Met Ala Gln Asp Gln Arg Ile Arg Trp Tyr
        1055                1060                1065

Leu Leu Ser Met Gly Ser Asn Glu Asn Ile His Ser Ile His Phe
        1070                1075                1080

Ser Gly His Val Phe Thr Val Arg Lys Lys Glu Glu Tyr Lys Met
        1085                1090                1095

Ala Leu Tyr Asn Leu Tyr Pro Gly Val Phe Glu Thr Val Glu Met
        1100                1105                1110

Leu Pro Ser Lys Ala Gly Ile Trp Arg Val Glu Cys Leu Ile Gly
        1115                1120                1125

Glu His Leu His Ala Gly Met Ser Thr Leu Phe Leu Val Tyr Ser
        1130                1135                1140

Asn Lys Cys Gln Thr Pro Leu Gly Met Ala Ser Gly His Ile Arg
        1145                1150                1155

Asp Phe Gln Ile Thr Ala Ser Gly Gln Tyr Gly Gln Trp Ala Pro
        1160                1165                1170

Lys Leu Ala Arg Leu His Tyr Ser Gly Ser Ile Asn Ala Trp Ser
        1175                1180                1185

Thr Lys Glu Pro Phe Ser Trp Ile Lys Val Asp Leu Leu Ala Pro
        1190                1195                1200

Met Ile Ile His Gly Ile Lys Thr Gln Gly Ala Arg Gln Lys Phe
        1205                1210                1215
```

Ser Ser Leu Tyr Ile Ser Gln Phe Ile Ile Met Tyr Ser Leu Asp
1220                1225                1230

Gly Lys Lys Trp Gln Thr Tyr Arg Gly Asn Ser Thr Gly Thr Leu
1235                1240                1245

Met Val Phe Phe Gly Asn Val Asp Ser Ser Gly Ile Lys His Asn
1250                1255                1260

Ile Phe Asn Pro Pro Ile Ile Ala Arg Tyr Ile Arg Leu His Pro
1265                1270                1275

Thr His Tyr Ser Ile Arg Ser Thr Leu Arg Met Glu Leu Met Gly
1280                1285                1290

Cys Asp Leu Asn Ser Cys Ser Met Pro Leu Gly Met Glu Ser Lys
1295                1300                1305

Ala Ile Ser Asp Ala Gln Ile Thr Ala Ser Ser Tyr Phe Thr Asn
1310                1315                1320

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr
1445                1450                1455

<210> SEQ ID NO 3
<211> LENGTH: 2220
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 3
gccaccagga gatactacct gggggctgtg gagctttctt gggactacat gcagtctgac        60
ctgggggagc tgcctgtgga tgccaggttc cacccagag tgcccaaatc cttcccattc        120
aacacctctg tggtctacaa gaagacccTc tttgtggagt tcactgacca cctgttcaac       180
attgccaaac ccaggccacc ctggatggga ctcctgggac ccaccattca ggctgaggtg       240
tatgacactg tggtcatcac cctcaagaac atggcctccc accctgtgag cctgcatgct      300 gtggggtca gctactggaa ggcctctgag gggctgagt atgatgacca gacctcccag         360
agggagaagg aggatgacaa agtgttccct gggggcagcc acacctatgt gtggcaggtc       420
ctcaaggaga atggccccat ggcctctgac ccactctgcc tgacctactc ctacctttct     480
catgtggacc tggtcaagga cctcaactct ggactgattg ggcccctgct ggtgtgcagg       540
gagggctccc tggccaaaga gaagacccag accctgcaca gttcattct cctgtttgct       600

-continued

```
gtctttgatg agggcaagag ctggcactct gaaaccaaga actccctgat gcaggacagg    660
gatgctgcct ctgccagggc ctggcccaag atgcacactg tgaatggcta tgtgaacagg    720
agcctgcctg gactcattgg ctgccacagg aaatctgtct actggcatgt gattggcatg    780
gggacaaccc ctgaggtgca ctccattttc ctggagggcc acaccttcct ggtcaggaac    840
cacagacagg ccagcctgga gatcagcccc atcaccttcc tcactgccca gaccctgctg    900
atggacctcg gacagttcct gctgttctgc cacatcagct cccaccagca tgatggcatg    960
gaggcctatg tcaaggtgga cagctgccct gaggagccac agctcaggat gaagaacaat   1020
gaggaggctg aggactatga tgatgacctg actgactctg agatggatgt ggtccgcttt   1080
gatgatgaca acagcccatc cttcattcag atcaggtctg tggccaagaa acaccccaag   1140
acctgggtgc actacattgc tgctgaggag gaggactggg actatgcccc actggtcctg   1200
gcccctgatg acaggagcta caagagccag tacctcaaca atgcccacac gaggattgga   1260
cgcaagtaca agaaagtcag gttcatggcc tacactgatg aaaccttcaa gaccagggag   1320
gccattcagc atgagtctgg catcctgggc ccactcctgt atgggaggt ggggacacc   1380 ctgctcatca tcttcaagaa ccaggcctcc aggccctaca acatctaccc acatggcatc   1440
actgatgtca ggcccctgta cagccgcagg ctgccaaagg gggtgaaaca cctcaaggac   1500
ttccccattc tgcctgggga gatcttcaag tacaagtgga ctgtcactgt ggaggatgga   1560
ccaaccaaat ctgaccccag gtgcctcacc agatactact ccagctttgt gaacatggag   1620
agggacctgg cctctggcct gattggccca ctgctcatct gctacaagga gtctgtggac   1680
cagaggggaa accagatcat gtctgacaag aggaatgtga ttctgttctc tgtctttgat   1740
gagaacagga ctggtacct gactgagaac attcagcgct tcctgcccaa ccctgctggg   1800
gtgcagctgg aggaccctga gttccaggcc agcaacatca tgcactccat caatggctat   1860
gtgtttgaca gcctccagct ttctgtctgc ctgcatgagg tggcctactg gtacattctt   1920
tctattgggg cccagactga cttcctttct gtcttcttct ctggctacac cttcaaacac   1980
aagatggtgt atgaggacac cctgaccctc ttcccattct ctggggagac tgtgttcatg   2040
agcatggaga accctggcct gtggattctg ggatgccaca ctctgacttt ccgcaacagg   2100
ggcatgactg ccctgctcaa agtctcctcc tgtgacaaga acactgggga ctactatgag   2160
gacagctatg aggacatctc tgcctacctg ctcagcaaga caatgccat tgagcccagg   2220
```

<210> SEQ ID NO 4
<211> LENGTH: 2052
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gagatcacca ggaccaccct ccagtctgac caggaggaga ttgactatga tgacaccatt     60
tctgtggaga tgaagaaaga ggactttgac atctatgacg aggacgagaa ccagagccca    120
aggagcttcc agaagaagac caggcactac ttcattgctg ctgtggagcg cctgtgggac    180
tatggcatga gctccagccc ccatgtcctc aggaacaggg cccagtctgg ctctgtgcca    240
cagttcaaga agtggtcttc caagagttc actgatggca gcttcaccca gccctgtac    300 agagggagc tgaatgagca cctgggactc ctgggcccat acatcagggc tgaggtggag    360
gacaacatca tggtgacctt ccgcaaccag gcctccaggc cctacagctt ctacagctcc    420
```

-continued

```
ctcatcagct atgaggagga ccagaggcag ggggctgagc cacgcaagaa ctttgtgaaa      480
cccaatgaaa ccaagaccta cttctggaaa gtccagcacc acatggcccc caccaaggat      540
gagtttgact gcaaggcctg ggcctacttc tctgatgtgg acctggagaa ggatgtgcac      600
tctggcctga ttggcccact cctggtctgc cacaccaaca ccctgaaccc tgcccatgga      660
aggcaagtga ctgtgcagga gtttgccctc ttcttcacca tctttgatga aaccaagagc      720
tggtacttca ctgagaacat ggagcgcaac tgcagggccc catgcaacat tcagatggag      780
gaccccacct tcaaagagaa ctaccgcttc catgccatca atggctacat catggacacc      840
ctgcctgggc ttgtcatggc ccaggaccag aggatcaggt ggtacctgct ttctatgggc      900
tccaatgaga acattcactc catccacttc tctgggcatg tcttcactgt gcgcaagaag      960
gaggagtaca gatggccct gtacaacctc taccctgggg tctttgagac tgtggagatg     1020
ctgccctcca agctggcat ctggagggtg gagtgcctca ttggggagca cctgcatgct     1080
ggcatgagca ccctgttcct ggtctacagc aacaagtgcc agaccccct gggaatggcc     1140 tctggccaca tcagggactt ccagatcact gcctctggcc agtatggcca gtgggccccc     1200
aagctggcca ggctccacta ctctggatcc atcaatgcct ggagcaccaa ggagccattc     1260
agctggatca aagtggacct gctggccccc atgatcatcc atggcatcaa gacccagggg     1320
gccaggcaga agttctccag cctgtacatc agccagttca tcatcatgta cagcctggat     1380
ggcaagaaat ggcagaccta cagaggcaac tccactggaa cactcatggt cttctttggc     1440
aatgtggaca gctctggcat caagcacaac atcttcaacc ccccaatcat cgccagatac     1500
atcaggctgc accccaccca ctacagcatc cgcagcaccc tcaggatgga gctgatgggc     1560
tgtgacctga actcctgcag catgcccctg ggcatggaga gcaaggccat ttctgatgcc     1620
cagatcactg cctccagcta cttcaccaac atgtttgcca cctggagccc aagcaaggcc     1680
aggctgcacc tccagggaag gagcaatgcc tggaggcccc aggtcaacaa cccaaaggag     1740
tggctgcagg tggacttcca gaagaccatg aaggtcactg gggtgaccac ccaggggggtc     1800 aagagcctgc tcaccagcat gtatgtgaag gagttcctga tcagctccag ccaggatggc     1860
caccagtgga cectcttctt ccagaatggc aaggtcaagg tgttccaggg caaccaggac     1920
agcttcaccc ctgtggtgaa cagcctggac ccccccctcc tgaccagata cctgaggatt     1980
cacccccaga gctgggtcca ccagattgcc ctgaggatgg aggtcctggg atgtgaggcc     2040
caggacctgt ac                                                       2052
```

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
agcttcagcc agaatccacc tgtcctgaaa cgccaccaga gg                         42
```

<210> SEQ ID NO 6
<211> LENGTH: 7827
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgccagct ggcgaaaggg ggatgtgctg caaggcgatt aagttgggta acgccagggt       360
tttcccagtc acgacgttgt aaaacgacgg ccagtgaatt cctcgagatt taaatgacgt       420
tggccactcc ctctctgcgc gctcgctcgc tcactgaggc cgggcgacca aggtcgccc        480
gacgcccggg ctttgcccgg cgggcctcag tgagcgagcg agcgcgcaga gagggagtgg       540
ccaactccat cactaggggt tcctgagttt aaacttcgtc gacgattcga gcttgggctg       600
caggtcgagg gcactgggag gatgttgagt aagatggaaa actactgatg acccttgcag       660
agacagagta ttaggacatg tttgaacagg ggccgggcga tcagcaggta gctctagagg       720
atccccgtct gtctgcacat ttcgtagagc gagtgttccg atactctaat ctccctaggc       780
aaggttcata tttgtgtagg ttacttattc tccttttgtt gactaagtca ataatcagaa       840
tcagcaggtt tggagtcagc ttggcaggga tcagcagcct gggttggaag gaggggtat        900
aaaagccccct tcaccaggag aagccgtcac acagactagg cgcgccaccg ccaccatgca       960
gattgagctg agcacctgct tcttcctgtg cctgctgagg ttctgcttct ctgccaccag      1020
gagatactac ctgggggctg tggagctttc ttgggactac atgcagtctg acctggggga      1080
gctgcctgtg gatgccaggt tcccacccag agtgcccaaa tccttcccat caacacctc       1140
tgtggtctac aagaagaccc tctttgtgga gttcactgac cacctgttca acattgccaa      1200
acccaggcca ccctggatgg gactcctggg acccaccatt caggctgagg tgtatgacac      1260
tgtggtcatc accctcaaga acatggcctc ccaccctgtg agcctgcatg ctgtgggggt      1320
cagctactgg aaggcctctg aggggctga gtatgatgac cagacctccc agagggagaa      1380
ggaggatgac aaagtgttcc ctggggggcag ccacacctat gtgtggcagg tcctcaagga      1440
gaatggcccc atggcctctg acccactctg cctgacctac tcctaccttt ctcatgtgga      1500
cctggtcaag gacctcaact ctggactgat tggggccctg ctggtgtgca gggagggctc      1560
cctggccaaa gagaagaccc agaccctgca caagttcatt ctcctgtttg ctgtctttga      1620
tgagggcaag agctggcact ctgaaaccaa gaactccctg atgcaggaca gggatgctgc      1680
ctctgccagg gcctggccca agatgcacac tgtgaatggc tatgtgaaca ggagcctgcc      1740
tggactcatt ggctgccaca ggaaatctgt ctactggcat gtgattggca tgggggacaac      1800
ccctgaggtg cactccattt tcctggaggg ccacaccttc ctggtcagga accacagaca      1860
ggccagcctg gagatcagcc ccatcacctt cctcactgcc cagaccctgc tgatggacct      1920
cggacagttc ctgctgttct gccacatcag ctcccaccag catgatggca tggaggccta      1980
tgtcaaggtg gacagctgcc ctgaggagcc acagctcagg atgaagaaca atgaggaggc      2040
tgaggactat gatgatgacc tgactgactc tgagatggat gtggtccgct tgatgatga       2100
caacagccca tccttcattc agatcaggtc tgtggccaag aaacacccca agacctgggt      2160
gcactacatt gctgctgagg aggaggactg ggactatgcc ccactggtcc tggcccctga      2220
tgacaggagc tacaagagcc agtacctcaa caatggccca cagaggattg gacgcaagta      2280
caagaaagtc aggttcatgg cctacactga tgaaaccttc aagaccaggg aggccattca      2340
```

```
gcatgagtct ggcatcctgg gcccactcct gtatggggag gtgggggaca ccctgctcat    2400
catcttcaag aaccaggcct ccaggcccta caacatctac ccacatggca tcactgatgt    2460
caggcccctg tacagccgca ggctgccaaa ggggtgaaa cacctcaagg acttccccat     2520
tctgcctggg gagatcttca agtacaagtg gactgtcact gtggaggatg gaccaaccaa    2580
atctgacccc aggtgcctca ccagatacta ctccagcttt gtgaacatgg agagggacct    2640
ggcctctggc ctgattggcc cactgctcat ctgctacaag gagtctgtgg accagagggg    2700
aaaccagatc atgtctgaca gaggaatgt gattctgttc tctgtctttg atgagaacag     2760
gagctggtac ctgactgaga acattcagcg cttcctgccc aaccctgctg gggtgcagct    2820
ggaggaccct gagttccagg ccagcaacat catgcactcc atcaatggct atgtgtttga    2880
cagcctccag ctttctgtct gcctgcatga ggtggcctac tggtacattc tttctattgg    2940
ggcccagact gacttccttt ctgtcttctt ctctggctac accttcaaac acaagatggt    3000
gtatgaggac accctgaccc tcttcccatt ctctggggag actgtgttca tgagcatgga    3060
gaaccctggc ctgtggattc tgggatgcca caactctgac ttccgcaaca ggggcatgac    3120
tgccctgctc aaagtctcct cctgtgacaa gaacactggg gactactatg aggacagcta    3180
tgaggacatc tctgcctacc tgctcagcaa gaacaatgcc attgagccca ggagcttcag    3240
ccagaatcca cctgtcctga aacgccacca gagggagatc accaggacca ccctccagtc    3300
tgaccaggag gagattgact atgatgacac catttctgtg gagatgaaga agaggacttt    3360
tgacatctat gacgaggacg agaaccagag cccaaggagc ttccagaaga agaccaggca    3420
ctacttcatt gctgctgtgg agcgcctgtg ggactatggc atgagctcca gcccccatgt    3480
cctcaggaac agggcccagt ctggctctgt gccacagttc aagaaagtgg tcttccaaga    3540
gttcactgat ggcagcttca cccagcccct gtacagaggg gagctgaatg agcacctggg    3600
actcctgggc ccatacatca gggctgaggt ggaggacaac atcatggtga ccttccgcaa    3660
ccaggcctcc aggccctaca gcttctacag ctccctcatc agctatgagg aggaccagag    3720
gcagggggct gagccacgca agaactttgt gaaacccaat gaaaccaaga cctacttctg    3780
gaaagtccag caccacatgg ccccaccaa ggatgagttt gactgcaagg cctgggccta    3840
cttctctgat gtggacctgg agaaggatgt gcactctggc ctgattggcc cactcctggt    3900
ctgccacacc aacaccctga accctgccca tggaaggcaa gtgactgtgc aggagtttgc    3960
cctcttcttc accatctttg atgaaaccaa gagctggtac ttcactgaga acatggagcg    4020
caactgcagg gccccatgca acattcagat ggaggacccc accttcaaag agaactaccg    4080
cttccatgcc atcaatggct acatcatgga caccctgcct gggcttgtca tggcccagga    4140
ccagaggatc aggtggtacc tgctttctat gggctccaat gagaacattc actccatcca    4200
cttctctggg catgtcttca ctgtgcgcaa gaaggaggag tacaagatgg ccctgtacaa    4260
cctctaccct ggggtctttg agactgtgga gatgctgccc tccaaagctg gcatctggag    4320
ggtggagtgc ctcattgggg agcacctgca tgctggcatg agcaccctgt tcctggtcta    4380
cagcaacaag tgccagaccc ccctgggaat ggcctctggc cacatcaggg acttccagat    4440
cactgcctct ggccagtatg gccagtgggc cccaagctg ccaggctcc actactctgg     4500 atccatcaat gcctggagca ccaaggagcc attcagctgg atcaaagtgg acctgctggc    4560
ccccatgatc atccatggca tcaagaccca ggggcagg cagaagttct ccagcctgta     4620
catcagccag ttcatcatca tgtacagcct ggatggcaag aaatggcaga cctacagagg    4680
```

-continued

```
caactccact ggaacactca tggtcttctt tggcaatgtg acagctctg gcatcaagca      4740 caacatcttc aacccccaa tcatcgccag atacatcagg ctgcaccca cccactacag       4800 catccgcagc accctcagga tggagctgat gggctgtgac ctgaactcct gcagcatgcc    4860
cctgggcatg gagagcaagg ccatttctga tgcccagatc actgcctcca gctacttcac   4920
caacatgttt gccacctgga gcccaagcaa ggccaggctg cacctccagg aaggagcaa    4980 tgcctggagg ccccaggtca acaacccaaa ggagtggctg caggtggact tccagaagac   5040
catgaaggtc actggggtga ccacccaggg ggtcaagagc ctgctcacca gcatgtatgt   5100
gaaggagttc ctgatcagct ccagccagga tggccaccag tggaccctct tcttccagaa   5160
tggcaaggtc aaggtgttcc agggcaacca ggacagcttc accctgtgg tgaacagcct    5220 ggaccccccc ctcctgacca gatacctgag gattcacccc cagagctggg tccaccagat   5280
tgccctgagg atggaggtcc tgggatgtga ggcccaggac ctgtactgat gacgagcggc   5340
cgctcttagt agcagtatcg ataataaaag atctttattt tcattagatc tgtgtgttgg   5400
ttttttgtgt gttaattaag ctcgcgaagg aaccctagt gatggagttg ccactccct     5460 ctctgcgcgc tcgctcgctc actgaggccg gcgaccaaa ggtcgcccga cgcccgggct    5520
ttgcccgggc ggcctcagtg agcgagcgag cgcgcagaga gggagtggcc aagacgattt   5580
aaatgacaag cttggcgtaa tcatggtcat agctgtttcc tgtgtgaaat tgttatccgc   5640
tcacaattcc acacaacata cgagccggaa gcataaagtg taaagcctgg ggtgcctaat   5700
gagtgagcta actcacatta attgcgttgc gctcactgcc cgctttccag tcgggaaacc   5760
tgtcgtgcca gctgcattaa tgaatcggcc aacgcgcggg gagaggcggt ttgcgtattg   5820
ggcgctcttc cgcttcctcg ctcactgact cgctgcgctc ggtcgttcgg ctgcggcgag   5880
cggtatcagc tcactcaaag gcggtaatac ggttatccac agaatcaggg gataacgcag   5940
gaaagaacat gtgagcaaaa ggccagcaaa aggccaggaa ccgtaaaaag gccgcgttgc   6000
tggcgttttt ccataggctc cgcccccctg acgagcatca caaaaatcga cgctcaagtc   6060
agaggtggcg aaacccgaca ggactataaa gataccaggc gtttccccct ggaagctccc   6120
tcgtgcgctc tcctgttccg accctgccgc ttaccggata cctgtccgcc tttctccctt   6180
cgggaagcgt ggcgctttct catagctcac gctgtaggta tctcagttcg gtgtaggtcg   6240
ttcgctccaa gctgggctgt gtgcacgaac cccccgttca gcccgaccgc tgcgccttat   6300
ccggtaacta tcgtcttgag tccaacccgg taagacacga cttatcgcca ctggcagcag   6360
ccactggtaa caggattagc agagcgaggt atgtaggcgg tgctacagag ttcttgaagt   6420
ggtggcctaa ctacggctac actagaagaa cagtatttgg tatctgcgct ctgctgaagc   6480
cagttacctt cggaaaaaga gttggtagct cttgatccgg caaacaaacc accgctggta   6540
gcggtggttt ttttgtttgc aagcagcaga ttacgcgcag aaaaaaagga tctcaagaag   6600
atcctttgat cttttctacg ggtctgacg ctcagtggaa cgaaaactca cgttaaggga    6660
ttttggtcat gagattatca aaaaggatct tcacctagat ccttttaaat taaaaatgaa   6720
gttttaaatc aatctaaagt atatatgagt aaacttggtc tgacagttac caatgcttaa   6780
tcagtgaggc acctatctca gcgatctgtc tatttcgttc atccatagtt gcctgactcc   6840
ccgtcgtgta gataactacg atacgggagg gcttaccatc tggccccagt gctgcaatga   6900
taccgcgaga cccacgctca ccggctccag atttatcagc aataaaccag ccagccggaa   6960
gggccgagcg cagaagtggt cctgcaactt tatccgcctc catccagtct attaattgtt   7020
gccgggaagc tagagtaagt agttcgccag ttaatagttt gcgcaacgtt gttgccattg   7080
```

```
ctacaggcat cgtggtgtca cgctcgtcgt ttggtatggc ttcattcagc tccggttccc    7140
aacgatcaag gcgagttaca tgatccccca tgttgtgcaa aaaagcggtt agctccttcg    7200
gtcctccgat cgttgtcaga agtaagttgg ccgcagtgtt atcactcatg gttatggcag    7260
cactgcataa ttctcttact gtcatgccat ccgtaagatg cttttctgtg actggtgagt    7320
actcaaccaa gtcattctga gaatagtgta tgcggcgacc gagttgctct tgcccggcgt    7380
caatacggga taataccgcg ccacatagca gaactttaaa agtgctcatc attggaaaac    7440
gttcttcggg gcgaaaactc tcaaggatct taccgctgtt gagatccagt tcgatgtaac    7500
ccactcgtgc acccaactga tcttcagcat cttttacttt caccagcgtt tctgggtgag    7560
caaaaacagg aaggcaaaat gccgcaaaaa agggaataag ggcgacacgg aaatgttgaa    7620
tactcatact cttccttttt caatattatt gaagcattta tcagggttat tgtctcatga    7680
gcggatacat atttgaatgt atttagaaaa ataaacaaat aggggttccg cgcacatttc    7740
cccgaaaagt gccacctgac gtctaagaaa ccattattat catgacatta acctataaaa    7800
ataggcgtat cacgaggccc tttcgtc                                       7827
```

<210> SEQ ID NO 7
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgcagatcg aactgagcac ttgcttcttc ctgtgtctcc tgcgcttttg cttctccgcc     60
acaaggagat actatctcgg tgccgtggag ctcagctggg actacatgca gagcgacttg    120
ggtgaactgc ctgtggacgc caggtttcca ccccgcgtgc ccaagagttt cccgttcaac    180
accagtgtcg tgtacaagaa aaccctcttc gtggaattca ccgaccacct gttcaacatc    240
gccaaaccgc gccctccctg gatggggctg ctcggcccga cgatccaggc tgaggtctat    300
gacacggtgg tgattaccct caagaacatg gctagccacc cggtgagcct gcacgccgtg    360
ggcgtgtcct attggaaagc gtccgagggt gcggagtacg atgaccagac ttcacagcgg    420
gagaaggaag acgacaaagt gttccccggg ggttcccaca cctatgtctg gcaggtcctg    480
aaggagaatg gtcctatggc ctccgaccca ttgtgcctca cctactctta cctaagccat    540
gtggatctcg tcaaggacct gaactcgggg ctgatcggcg ccctgctcgt gtgccgggag    600
ggctcactgg ccaaggagaa gacccaaaact ctgcacaagt tcatcctgct gttcgcggta    660
ttcgacgagg ggaagtcctg gcactccgag accaagaaca gcctgatgca ggaccgcgac    720
gcagcctcgg cccgtgcgtg gccaaagatg cacaccgtga acggctacgt aacaggagc     780 ctacccggcc tgatcggctg ccaccgcaaa tcggtctact ggcatgtgat cggaatgggc    840
acaacgcccg aggtccacag tatcttcctc gagggccaca ctttcctggt ccggaatcac    900
cgccaggcca gctggagat cagccccata acctttctga cggcgcagac cttactcatg    960
gatctcggcc agttcctcct gttctgccac atttcgtccc accagcacga tgggatggaa   1020
gcatatgtga agtggactc ctgccccgag gaaccccagc ttaggatgaa gaacaatgag    1080
gaggccgagg actacgacga tgaccttacc gattcagaaa tggacgtagt acgctttgac    1140
gacgacaact ctccatcctt catacagatt cgctccgtcg ccaagaagca cctaagact    1200 tgggtgcact acatcgcggc cgaggaggag gactgggatt atgctcccct ggtgctggcc    1260
```

```
cccgacgacc gcagctacaa gagccagtac ctgaataacg ggccccagcg catcggccgg   1320
aagtacaaga aagtgcggtt catggcttac acggacgaga ccttcaagac ccgggaggct   1380
atccagcatg agagcggcat cttggggccc ctcctgtacg gcgaagttgg agacacactg   1440
ctgatcatct tcaagaacca ggcgagcagg ccctacaaca tctacccca cggcattacc     1500 gatgtccggc cgttgtacag ccgacggctg cccaagggcg tgaagcacct gaaggacttt   1560
ccgatcctgc cgggcgagat cttcaagtac aagtggactg taccgtgga ggatgggccg    1620 accaagagcg atccgcgctg cctgacccgt tactactcca gctttgtcaa tatggagcgc   1680
gacctcgcta gcggcttgat tggccctctg ctgatctgct acaaggagtc cgtggaccag   1740 aggggggaatc agatcatgag tgacaagagg aacgtgatcc tgttctccgt gttcgacgaa   1800
aaccgcagct ggtatctcac cgagaatatc cagcgcttcc tgcccaaccc ggccggtgtg   1860
cagctggagg accccgagtt tcaggccagc aacatcatgc attctatcaa cggatatgtg   1920
tttgattccc tgcagctctc agtgtgtctg cacgaggtcg cctactggta tatcctcagc   1980
attggggcac agaccgactt cctgagcgtg ttcttctccg ggtataccctt caagcacaag   2040 atggtgtacg aggataccct gaccctgttc cccttttagcg gcgaaaccgt gtttatgtct   2100
atggagaacc ccgggctctg gatccttggc tgccataact ccgacttccg caaccgcgga   2160
atgaccgcgc tcctgaaagt gtcgagttgt gacaagaaca ccggcgacta ttacgaggac   2220
agttacgagg acatctctgc gtacctcctt agcaagaata cgccatcga gccaagatcc   2280 ttcagccaga accccccagt gctgaagagg catcagcggg agatcacccg cacgaccctg   2340
cagtcggatc aggaggagat tgattacgac gacacgatca gtgtggagat gaagaaggag   2400
gacttcgaca tctacgacga agatgaaaac cagtcccctc ggtccttcca aaagaagacc   2460
cggcactact tcatcgccgc tgtggaacgc ctgtgggact atggaatgtc ttctagccct   2520
cacgttttga ggaaccgcgc ccagtcgggc agcgtgcccc agttcaagaa agtggtgttc   2580
caggagttca ccgacggctc cttcacccag ccactttacc ggggcgagct caatgaacat   2640
ctgggcctgc tgggaccctta catcagggct gaggtggagg acaacatcat ggtgacattc   2700
cggaatcagg ccagcagacc atacagttc tacagttcac tcatctccta cgaggaggac     2760
cagcgccagg gggctgaacc ccgtaagaac ttcgtgaagc caaacgaaac aaagacctac   2820
ttctggaagg tccagcacca catggcacct accaaggacg agttcgattg caaggcctgg   2880
gcctacttct ccgacgtgga cctggagaaa gatgtgcaca gcggcctgat tggccctctg   2940
ctggtgtgtc acacgaacac actcaaccct gcacacgggc ggcaggtcac tgtgcaggaa   3000
ttcgccctgt tctttaccat cttgatgag acgaagtcct ggtatttcac cgaaaacatg     3060
gagaggaact gccgcgcacc ctgcaacatc cagatgaag atccgacatt caaggagaac    3120
taccggttcc atgccatcaa tggctacatc atggacaccc tgcctggcct cgtgatggcc   3180
caagaccagc gtatccgctg gtatctgctg tcgatgggct ccaacgagaa catccatagt   3240
atccacttca gcgggcatgt cttcacggtg aggaaaaagg aggagtacaa gatggcactg   3300
tacaacctct atcccggcgt gttcgagacc gtggagatgc tgccctccaa ggccggcatc   3360
tggagagtgg aatgcctgat cggcgagcac ctccacgctg gatgtccac gctgttcctc      3420 gtttacagca ataagtgcca gacccctctg ggcatggcga gcggccacat ccgcgacttc   3480
cagattacag ccgcggcca gtacggtcag tgggctccaa agctggcccg tctgcactac    3540 tccgatcca tcaacgcctg gtccaccaag gaaccgttct cctggatcaa agtagacctg   3600
```

-continued

| | |
|---|---|
| ctagccccca tgatcattca cggcatcaag acacaaggcg cccgacagaa gttctcgagc | 3660 |
| ctctatatct cccagttcat catcatgtat agcctggacg gaaagaagtg gcagacttac | 3720 |
| cgcggaaact cgacagggac cctgatggta ttcttcggta acgtggacag ctccggaatc | 3780 |
| aagcacaaca tcttcaaccc acccattatc gcccgctaca tccgcctgca ccccactcac | 3840 |
| tatagcatta ggtccaccct gcgaatggag ctcatgggct gtgacctgaa cagctgtagc | 3900 |
| atgcccctcg gcatggagtc taaggcgatc tccgacgcac agataacggc atcatcctac | 3960 |
| tttaccaaca tgttcgctac ctggtccccc tccaaggccc gactccacct gcaagggaga | 4020 |
| tccaacgcct ggcggccaca ggtcaacaat cccaaggagt ggctgcaagt ggactttcag | 4080 |
| aaaactatga aagtcaccgg agtgaccaca cagggagtga agtctctgct gaccagcatg | 4140 |
| tacgtgaagg agttcctcat ctccagttcg caggatggcc accagtggac gttgttcttc | 4200 |
| caaaacggta aagtcaaagt cttccaaggg aaccaggaca gctttacacc cgtcgtgaac | 4260 |
| tccctggacc ccccgcttct cactagatac ctccgcatcc accctcagag ctgggtgcac | 4320 |
| cagattgccc tgcgcatgga ggttctgggg tgtgaagccc aggacctgta ctaa | 4374 |

<210> SEQ ID NO 8
<211> LENGTH: 4374
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 8

| | |
|---|---|
| atgcagattg agctctccac ctgcttcttt ctctgccttc ttcgcttctg cttttctgcc | 60 |
| acacgcaggt actatttggg agcagtggaa ctgagctggg attacatgca gagtgacctt | 120 |
| ggtgaacttc ctgtggacgc tcgttttcca cctagagttc ccaagtcctt ccccttcaac | 180 |
| acctcagtgg tctacaagaa aacgctgttt gtggagttca ctgaccacct cttcaacatt | 240 |
| gccaaaccaa gaccccttg atgggattg ctggaccca aatacaagc agaagtctac | 300 |
| gacacggtgg tgattaccct gaagaacatg gcgtcacacc ctgtttcact tcacgctgtt | 360 |
| ggggtcagtt attggaaagc tcagagggt gcggaatacg atgatcaaac cagccagagg | 420 |
| gagaaggaag atgacaaggt cttttcctggg ggtagccata cctatgtttg gcaggtgctg | 480 |
| aaagagaatg ggcctatggc ctctgatccc ttgtgcctca catactctta cctgagtcac | 540 |
| gtcgacctgg tgaaagacct gaatagcggt ctgattggtg cactgcttgt ttgtagagag | 600 |
| gggagtttgg ccaaggagaa aactcagact ctccacaagt ttatcctcct gtttgctgtg | 660 |
| ttcgacgagg gcaagtcttg gcactctgaa acaagaact ccctgatgca ggacagagat | 720 |
| gctgcatctg caagggcttg gccaaaaatg cacacagtga acggctatgt gaatcgatca | 780 |
| ctgccaggac tgataggctg tcatcgcaag tcagtgtatt ggcacgttat cgggatggga | 840 |
| acaactccag aagtgcacag catcttcctt gagggccaca cttttcctgg tcggaatcat | 900 |
| agacaggcca gccttgagat cagcccaatc acctttctga ctgcccaaac cttgctgatg | 960 |
| gatctgggac agttcctcct gttttgtcac atctcctccc accaacatga cgggatggag | 1020 |
| gcttatgtga aggtcgatag ctgtccggag gaaccacaac tgaggatgaa gaacaacgaa | 1080 |
| gaggcagagg actatgacga cgatctgact gacagtgaaa tggacgtggt tcggttcgac | 1140 |
| gatgacaatt ctccttcatt tatccagatc cgttccgtgg ccaagaagca ccccaagact | 1200 |
| tgggttcatt acatcgctgc tgaggaggag gattgggact acgcgccctt ggtgttggcc | 1260 |

```
ccagacgatc gctcatacaa gagccagtac cttaacaatg gtccacaaag gatcggccgg      1320
aagtacaaga aggttagatt tatggcttat accgacgaga cttttaaaac tagggaagca      1380
attcagcatg aaagtggcat tcttggaccc ctgctgtatg gcgaggttgg cgacaccctg      1440
ctgattatct ttaagaacca ggcaagccgg ccctacaaca tctacccgca cggcataacc      1500
gatgtacgac ccctgtacag tcgcagactt cctaaagggg tgaaacacct gaaggacttc      1560
ccaattctgc ccggggagat cttcaagtat aaatggaccg tgacggttga ggatggtccc      1620
acaaagtccg atccgagatg ccttacccga tattattcca gcttcgtgaa catggaaagg      1680
gacctggcca gcgggctgat tggcccactg ctgatttgtt acaaggagtc tgtcgatcaa      1740
agaggaaacc aaataatgag cgacaaacgt aacgtcatcc tgttcagcgt ctttgatgag      1800
aatagaagct ggtacctcac agaaaatatt cagcggtttc tgcctaaccc cgcaggcgtc      1860
cagctggaag atcccgagtt ccaagcctca acatcatgc atagcatcaa cggatacgta       1920
ttcgatagcc tgcagctgtc cgtctgtctc catgaagtgg catattggta catcctgagt      1980 atcgggcgc agaccgactt cctgagcgtg ttctttctg gatacacgtt caaacacaaa        2040
atggtctatg aagataccct gactctgttt ccattctcag agagacagt ctttatgagt       2100 atggaaaatc tggactgtg gatcctgggc tgtcacaatt ctgattttcg gaacagaggc       2160
atgacagccc tgcttaaagt gagctcatgc gacaagaaca ccggtgatta ctacgaagat     2220
agctatgagg acatcagtgc gtatttgctc tccaagaaca acgctatcga gccacggtct     2280
ttcagtcaga atcctcccgt tctgaagcgg catcagcgcg aaataacacg cacaacccttt    2340 cagtcagacc aagaggaaat cgactacgat gatactatct ctgtggagat gaagaaggag    2400
gatttcgaca tttacgacga ggacgagaat cagtccccaa ggagctttca gaagaaaaca    2460
agacactatt tcattgccgc cgtggagcga ctgtgggact acggcatgtc tagctctccg    2520
catgtactta gaaatagggc acaaagcgga tccgtgcctc agtttaagaa agttgtcttt    2580 caggagtttta cagatggctc cttcacccag cccttgtatc gcggggaact caatgaacac   2640
ctgggcctcc tgggtcctta tattagggcc gaagtcgagg acaatatcat ggtgaccttt    2700
aggaaccagg catctagacc ttactctttc tactcctccc tgatatccta tgaggaggac   2760
cagcggcaag gcgctgagcc tcggaagaac tttgtgaagc caaatgaaac caaaacatac   2820
ttttggaaag ttcagcacca catggctccc acgaaggacg aatttgactg taaagcctgg   2880
gcctacttct cagatgtaga tctcgagaaa gacgtgcact cagggctcat tggtccctc    2940 ctggtctgtc atactaatac cctcaatcca gcacacggac gtcaggtaac cgtccaggaa   3000
tttgccctgt tctttaccat tttcgatgag actaaatcct ggtactttac cgaaaacatg   3060
gagaggaatt gcagagcccc atgcaacatc cagatggagg accctaccttc aaagagaac   3120 tatcgcttcc atgccattaa cggttacatt atggatactc tcccaggact tgtgatggca   3180
caggatcagc ggataagatg gtatctgttg agcatgggct ccaacgagaa tattcacagc   3240
atccatttct ccgtcacgt gtttacagtg agaaagaaag aagagtacaa gatggctctg   3300
tataatctct atccaggcgt attcgaaacg gtggagatgt tgcctagcaa ggccggcatt   3360
tggcgagtag aatgccttat cggggaacat ctgcatgccg gaatgagcac gctcttcctg   3420
gtgtatagta acaagtgcca gactccgctg ggcatggcat ctggccatat acgggacttt   3480
cagattacgg ctagcgggca gtatgggcag tgggcaccca aacttgcgcg actgcactat   3540
tcaggctcta tcaatgcatg gtccaccaag gaacccttct cttggattaa ggtggacctt   3600
ttggcgccca tgataatcca tgggatcaaa acccagggcg ctcgtcagaa attctcatca   3660
```

```
ctctacatct ctcagttcat aataatgtat tcactggatg ggaagaaatg gcagacttac    3720
agaggaaaca gcaccgggac gctgatggtg ttctttggca acgtggacag cagcggcatc    3780
aaacacaaca tcttcaatcc tcccattatt gcccgttata ttagactgca tcccactcac    3840
tactctatac gcagcacact taggatggag ctcatgggat gcgacctgaa cagttgtagt    3900
atgcccttgg ggatggagtc caaagctata agcgacgcac aaattacagc tagctcttac    3960
tttacgaata tgttcgccac gtggagccca agcaaagccc ggctgcattt gcagggtcgg    4020
agtaatgctt ggcgcccaca ggtgaataac cctaaggaat ggttgcaagt agatttccag    4080
aaaactatga aggtaaccgg cgtcactaca cagggagtca agtccctctt gacctctatg    4140
tacgtcaagg agttcctgat tagcagcagt caggatgggc accaatggac actgttcttc    4200
cagaatggga aagttaaagt atttcagggt aaccaggact cctttacacc tgtggtgaat    4260
agcctcgacc caccccctgct gacacgatac ctccgcatcc accctcagtc ttgggtgcat    4320
caaattgccc tgcgaatgga ggtgttggga tgcgaagctc aggacctcta ctga          4374
```

<210> SEQ ID NO 9
<211> LENGTH: 4374
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 9

```
atgcagatcg aactctctac ttgcttcttc ctgtgccttc tgaggttctg cttctctgcc     60
actcgccgat attacctcgg ggccgtggag ttgagttggg actacatgca atcagatctg    120
ggcgaactcc ctgtggatgc ccgattccca ccgcgcgtgc ccaagtcttt cccatttaat    180
acttctgtgg tgtacaagaa gacattgttt gtggagttta ccgatcacct gttcaacatc    240
gccaaaccgc ggcccccatg gatgggtctg cttgggccca ccattcaagc ggaggtctat    300
gatacagtgg tgataacgct taagaacatg gcgagccacc cagtgtctct gcatgccgtt    360
ggtgtatcat attggaaggc cagcgaagga gcggagtacg atgaccagac tctcagagaa    420
gagaaggaag acgataaggt tttcctggc ggaagtcata catatgtatg gcaggtcctg    480
aaagagaatg ggccgatggc ttctgacccc ctttgtctta cctatagtta tctgagccac    540
gtggacctgg tcaaggacct caacagtggt ctgattgggg ctctgcttgt ttgtagagag    600
ggtagcttgg ctaaggagaa aacccaaaca ctccataagt tcattttgct gttcgcggtg    660
ttcgacgagg gaaagagttg gcacagcgaa acaaagaatt cactgatgca agacagggac    720
gccgcttccg caagggcttg gcctaagatg catacggtga atgggtatgt gaaccggagc    780
ctccccgggc tgatcgggtg ccatcgcaag tctgtttact ggcacgtcat tggaatgggg    840
acaacgccag aggtacatag tatatttctt gaaggccaca cgttcctcgt acggaaccac    900
cgacaggctt ccctggagat aagccccatt acctttctga ccgctcagac tctgctgatg    960
gaccttggcc agtttctcct gttctgccat attagcagcc accagcacga cggtatggaa    1020
gcatacgtga aagtcgatag ctgtcctgag gagcctcagc tcagaatgaa gaacaacgag    1080
gaggccgaag actatgacga tgaccttaca gattccgaga tggacgtggt gcgctttgac    1140
gacgataaca gtcctagttt cattcaaatc agatccgtag ccaaaaagca tccaaagaca    1200
tgggtgcatt acattgcagc cgaagaggag gattgggatt atgcgcccct tgttctggct    1260
ccagatgaca ggagctataa gtcccagtac ttgaacaacg gccacagcg aatcggtaga    1320
```

```
aaatataaga aggtaagatt catggcctac actgacgaaa catttaaaac cagggaagct   1380
atccaacacg aatctggaat tctcggccct ctgctctacg gtgaggtggg ggacaccttg   1440
ctgatcattt tcaaaaatca ggcatccagg ccttacaaca tatacccca tggcatcacc    1500
gatgtccgcc cgctgtattc cagaagactc cccaagggga tgaaacatct gaaagatttt   1560
cccatcctgc cgggcgagat cttaaaatac aaatggactg tgactgtaga ggacgggcct   1620
acaaaatcag acccacggtg cctgacaagg tattacagta gcttcgtcaa catggaacgc   1680
gacctcgcca gcggactcat tggcccactg ttgatctgtt acaaagagtc agtggatcag   1740
aggggaaatc agatcatgag cgataagaga acgttatcc tgtttagtgt cttcgacgag    1800
aaccggtctt ggtaccttac tgagaacatc cagaggttcc tgccgaatcc ggctggcgtt   1860
cagctcgagg acccagagtt ccaggccagt aatataatgc actcaatcaa cggttatgtg   1920
ttcgatagcc tgcagctgag cgtctgcctc cacgagtag cctattggta catattgtcc    1980
atcgggctc agaccgattt tctgtccgtg ttctttagcg gtataccctt taaacataaa    2040
atggtctatg aagacaccct gaccctgttc ccattctccg gtgagactgt gttcatgtcc   2100
atggagaacc cagggctgtg gatcctgggg tgtcacaata gtgactttag gaatcgggga   2160
atgacggcac tgctgaaggt gagttcttgc gataaaaata caggagatta ctatgaggat   2220
agttacgagg atatcagtgc ctatctgctt tcaaaaaaca cgcaattga gccccggtct    2280
ttctcacaaa acccccggt gctgaagcgc caccagcgcg aaattacccg acaaccttg     2340
cagtccgacc aggaggaaat cgattatgac gatactatca gtgtagaaat gaaaaaggag   2400
gattttgata tttacgacga agacgagaac cagtctccgc gaagttttca aagaaaacg    2460
cgacactact ttatagctgc cgtggaacga ctctgggatt atggcatgtc ctccagccct   2520
catgtcctta ggaatcgagc gcagagtggc tctgtgcctc agttcaaaaa ggttgtgttc   2580
caggaattca ccgacggctc atttacccag ccgctgtaca gaggcgaact caacgaacac   2640
cttgggctgc ttgggccata tattcgagca gaggtggaag ataatatcat ggtaaccttt   2700
agaaaccagg cgtcaagacc ctattccttc tacagttctc tgatcagcta cgaggaggac   2760
caaagacagg gagctgaacc caggaagaac tttgtgaaac ctaatgagac caagacctac   2820
ttctggaagg tccagcacca tatggcccca actaaagatg aattcgattg caaggcctgg   2880
gcttatttca cgacgtgga tctcgaaaag gatgtgcaca cgggttgat cggaccgctt     2940
ttggtgtgcc acacaaatac cctcaatcct gcccacgggc ggcaggtcac agttcaagag   3000
tttgcactct tctttacaat atttgacgag acaaagtcat ggtattttac agagaatatg   3060
gagagaaatt gtcgcgcacc ttgcaacatt cagatggagg accccacatt taaggagaat   3120
tacagatttc atgctatcaa tgggtacatt atggatactc tgcctggtct ggtcatggcc   3180
caggatcagc gcataaggtg gtacttgctg agcatgggat ctaatgagaa tatacacagc   3240
attcacttca gtggccacgt ttttactgtt agaaagaagg aggagtacaa aatgcgcgctc   3300
tacaaccttt acccgggtgt gtttgagaca gtggagatgc tgccaagcaa ggcaggcatc   3360
tggagggttg agtgtcttat tggggagcat ctgcatgctg aatgtccac cctctttctt    3420
gtgtacagca ataagtgcca gacaccgctt ggcatggcca cggccacat tagggacttt   3480
cagataactg ccagtggaca gtacggccag tgggctccca agcttgcaag actccactac   3540
tccggaagca taaacgcatg gagcaccaag gaacccttct cttggattaa ggtggacctg   3600
ctggcgccaa tgatcattca cggcataaaa acccaagggg cacgacagaa attttcatct   3660
```

| | |
|---|---|
| ttgtatatta gtcagtttat catcatgtac agcttggatg aaagaagtg gcagacgtac | 3720 |
| agggcaatt ctacaggaac acttatggtg tttttggga atgtcgattc cagcgggatc | 3780 |
| aaacataaca tcttcaatcc tcctattatc gcccgatata tccgcctgca ccctacgcat | 3840 |
| tactccatca ggtccacatt gagaatgaaa ctgatggggt gcgacctgaa tagttgtagt | 3900 |
| atgccactgg gcatggagtc taaagccatc agcgatgcac agatcactgc cagctcttac | 3960 |
| ttcaccaaca tgtttgcaac ttggtcccccc tctaaagctc gcctgcatct gcagggacgc | 4020 |
| tcaaatgcat ggcgaccaca ggtgaacaat ccaaaagagt ggctccaggt cgactttcag | 4080 |
| aagacaatga aggtaacagg agtgacaacc cagggtgtaa aaagcctcct tacgagtatg | 4140 |
| tacgttaagg agtttctgat tctagctcc caggacggac accagtggac tctgttcttc | 4200 |
| cagaacggca aagtgaaggt atttcaggga accaggatt cttttacccc ggtagtgaat | 4260 |
| agcctggatc caccgttgct gacccgctat ctgagaattc atccacaatc ctgggtgcat | 4320 |
| cagattgccc tccggatgga agtgctcggc tgtgaagctc aggatctgta ttag | 4374 |

<210> SEQ ID NO 10
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | |
|---|---|
| atgcaaatag agctctccac ctgcttcttt ctgtgccttt tgcgattctg ctttagtgcc | 60 |
| accagaagat actacctggg tgcagtggaa ctgtcatggg actatatgca aagtgatctc | 120 |
| ggtgagctgc ctgtggacgc aagatttcct cctagagtgc caaatctttt tccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaagacttt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggataggat | 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca catttcttgt gaggaaccat | 900 |
| cgccaggcgt cctggaaat ctcgccaata acttctccta ctgctcaaac actcttgatg | 960 |
| gaccttggac agtttctact gttttgtcat atctcttccc accaacatga tggcatggaa | 1020 |
| gcttatgtca agtagacag ctgtccagag aaccccaac tacgaatgaa aaataatgaa | 1080 |
| gaagcggaag actatgatga tgatcttact gattctgaaa tggatgtggt caggtttgat | 1140 |
| gatgacaact ctccttcctt tatccaaatt cgctcagttg ccaagaagca tcctaaaact | 1200 |
| tgggtacatt acattgctgc tgaagaggag gactgggact atgctccctt agtcctcgcc | 1260 |
| cccgatgaca gaagttataa aagtcaatat ttgaacaatg gccctcagcg gattggtagg | 1320 |

```
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatatacctt caaacacaaa    2040
atggtctatg aagacacact caccctattc ccattctcag agaaactgt cttcatgtcg    2100 atggaaaacc caggtctatg gattctgggg tgccacaact cagactttcg aacagaggc    2160 atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga atccaccagt cttgaaacgc atcaacggg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata taagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat ggacccctt    2940 ctggtctgcc acactaacac actgaaccct gctcatggga gacaagtgac agtacaggaa    3000
tttgctctgt tttcaccat cttttgatgag accaaaagct ggtacttcac tgaaaatatg    3060
gaaagaaact gcagggctcc ctgcaatatc cagatggaag atcccacttt taagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtgacatgt gttcactgta cgaaaaaaag aggagtataa aatggcactg    3300
tacaatctct atccaggtgt ttttgagaca gtggaaatgt taccatccaa gctggaatt    3360 tgcgggtgg aatgccttat tggcgagcat ctacatgctg ggatgagcac acttttttctg    3420 gtgtacagca ataagtgtca gactcccctg ggaatggctt ctggacacat tagagatttt    3480
cagattacag cttcaggaca atatggacag tgggccccaa gctggccag acttcattat    3540 tccggatcaa tcaatgcctg gagcaccaag gagcccttt cttggatcaa ggtggatctg    3600
ttggcaccaa tgattattca cggcatcaag acccagggtg cccgtcagaa gttctcccagc    3660 ctctacatct ctcagtttat catcatgtat agtcttgatg gaagaagtg gcagacttat    3720
```

-continued

```
cgaggaaatt ccactggaac cttaatggtc ttctttggca atgtggattc atctgggata    3780
aaacacaata tttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa atctctgct taccagcatg    4140 tatgtgaagg agttcctcat ctccagcagt caagatggcc atcagtggac tctctttttt    4200
cagaatggca aagtaaaggt ttttcaggga aatcaagact ccttcacacc tgtggtgaac    4260
tctctagacc caccgttact gactcgctac cttcgaattc accccagag ttgggtgcac    4320 cagattgccc tgaggatgga ggttctgggc tgcgaggcac aggacctcta ctga          4374
```

<210> SEQ ID NO 11
<211> LENGTH: 4374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
atgcagatcg agctgtccac atgctttttt ctgtgcctgc tgcggttctg cttcagcgcc      60
acccggcggt actacctggg cgccgtggag ctgtcctggg actacatgca gagcgacctg     120
ggcgagctgc ccgtggacgc ccggttcccc ccagagtgc ccaagagctt ccccttcaac      180
accagcgtgt gtacaagaa aaccctgttc gtggagttca ccgaccacct gttcaacatc      240
gccaagccca ggcccccctg gatgggcctg ctgggcccca ccatccaggc cgaggtgtac     300
gacaccgtgg tgatcaccct gaagaacatg ccagccacc ccgtgagcct gcacgccgtg      360
ggcgtgagct actggaaggc ctccgagggc gccgagtacg acgaccagac cagccagcgg    420
gagaaagagg acgacaaagt ctttcctggc ggcagccaca cctacgtgtg gcaggtcctg    480
aaagaaaacg gccccatggc ctccgacccc ctgtgcctga cctacagcta cctgagccac    540
gtggacctgg tgaaggacct gaacagcggg ctgattgggg ccctgctggt ctgccgggag    600
ggcagcctgg ccaaagagaa acccagacc ctgcacaagt tcatcctgct gttcgccgtg     660
ttcgacgagg gcaagagctg gcacagcgag accaagaaca gcctgatgca ggaccgggac    720
gccgcctctg ccagagcctg gcccaagatg cacaccgtga acggctacgt gaacagaagc    780
ctgcccggcc tgattggctg ccaccggaag agcgtgtact ggcacgtgat cggcatgggc    840
accacacccg aggtgcacag catctttctg gaagggcaca ccttctggt gcggaaccac    900 cggcaggcca gctggaaat cagccctatc accttcctga ccgcccagac actgctgatg    960
gacctgggcc agttcctgct gttttgccac atcagctctc accagcacga cggcatggaa   1020
gcctacgtga aggtggactc ctgccccgag aacccccagc tgcggatgaa gaacaacgag   1080
gaagccgagg actacgacga cgacctgacc gacagcgaga tggacgtggt gcggttcgac   1140
gacgacaaca gccccagctt catccagatc agaagcgtgg ccaagaagca ccccaagacc   1200
tgggtgcact acatcgccgc cgaggaagag gactgggact acgccccct ggtgctggcc   1260 cccgacgaca aagctacaa gagccagtac ctgaacaatg gccccagcg gatcggccgg   1320 aagtacaaga agtgcggtt catggcctac accgacgaga ccttcaagac ccgggaggcc   1380
```

-continued

```
atccagcacg agagcggcat cctgggcccc ctgctgtacg gcgaagtggg cgacacactg    1440
ctgatcatct tcaagaacca ggccagccgg ccctacaaca tctaccccca cggcatcacc    1500
gacgtgcggc ccctgtacag caggcggctg cccaagggcg tgaagcacct gaaggacttc    1560
cccatcctgc ccggcgagat cttcaagtac aagtggaccg tgaccgtgga ggacggcccc    1620
accaagagcg accccagatg cctgacccgg tactacagca gcttcgtgaa catggaacgg    1680
gacctggcct ccgggctgat cggacctctg ctgatctgct acaaagaaag cgtggaccag    1740
cggggcaacc agatcatgag cgacaagcgg aacgtgatcc tgttcagcgt gttcgatgag    1800
aaccggtcct ggtatctgac cgagaacatc cagcggtttc tgcccaaccc tgccggggtg    1860
cagctggaag atcccgagtt ccaggccagc aacatcatgc actccatcaa tggctacgtg    1920
ttcgacagcc tgcagctgtc cgtgtgtctg cacgaggtgg cctactggta catcctgagc    1980
atcggcgccc agaccgactt cctgagcgtg ttcttcagcg gctacacctt caagcacaag    2040
atggtgtacg aggacaccct gaccctgttc cctttcagcg gcgagaccgt gttcatgagc    2100
atggaaaacc ccggcctgtg gatcctgggc tgccacaaca gcgacttccg gaaccggggc    2160
atgaccgccc tgctgaaggt gtccagctgc gacaagaaca ccggcgacta ctacgaggac    2220
agctacgagg atatcagcgc ctacctgctg tccaagaaca cgccatcga gcccagaagc    2280 ttcagccaga ccccctgt gctgaagcgg caccagagag atcacccg gaccaccctg    2340 cagtccgacc aggaagagat cgattacgac gacaccatca gcgtggagat gaaaaaagaa    2400
gatttcgaca tctacgacga ggacgagaac cagagccccc ggtccttcca gaagaaaacc    2460
cggcactact ttatcgccgc cgtggagcgg ctgtgggact acggcatgag cagcagcccc    2520
cacgtgctgc ggaaccgggc ccagagcggc agcgtgcccc agttcaagaa agtggtgttc    2580
caggaattca ccgacggcag cttcacccag cccctgtacc ggggcgagct gaacgagcac    2640
ctggggctgc tggggcccta catcagggcc gaagtggagg acaacatcat ggtgaccttc    2700
cggaatcagg ccagcagacc ctactccttc tacagcagcc tgatcagcta cgaagaggac    2760
cagcggcagg cgctgaacc ccggaagaac ttcgtgaagc ccaatgagac caagacctac    2820
ttctggaaag tgcagcacca catggccccc accaaggacg agttcgactg caaggcctgg    2880
gcctacttca gcgacgtgga tctggaaaag gacgtgcact ctggactgat tggccctctg    2940
ctggtgtgcc acaccaacac cctgaacccc gcccacggcc ggcaggtgac cgtgcaggaa    3000
ttcgccctgt tcttcaccat cttcgacgag accaagtcct ggtacttcac cgagaatatg    3060
gaacggaact gcagagcccc ctgcaacatc cagatgaag atcctacctt caaagagaac    3120
taccggttcc acgccatcaa cggctacatc atggacaccc tgcctggcct ggtgatggcc    3180
caggaccaga ggatccggtg gtatctgctg tccatgggca gcaacgagaa tatccacagc    3240
atccacttca gcggccacgt gttcaccgtg aggaagaaag aagagtacaa gatggccctg    3300
tacaacctgt accccggcgt gttcgagacc gtggagatgc tgcccagcaa ggccggcatc    3360
tggcgggtgg agtgtctgat cggcgagcac ctgcatgccg ggatgagcac cctgtttctg    3420
gtgtacagca acaagtgcca gacccccctg ggcatggcca gcggccacat ccgggacttc    3480
cagatcaccg cctccggcca gtacggccag tgggcccca agctgccccg gctgcactac    3540
agcggcagca tcaacgcctg gtccaccaaa gagcccttca gctggatcaa ggtggacctg    3600 ctggcccta tgatcatcca cggcattaag acccagggcg ccaggcagaa gttcagcagc    3660
ctgtacatca gccagttcat catcatgtac agcctggacg gcaagaagtg gcagacctac    3720
```

| | |
|---|---:|
| cggggcaaca gcaccggcac cctgatggtg ttcttcggca acgtggacag cagcggcatc | 3780 |
| aagcacaaca tcttcaaccc ccccatcatc gcccggtaca tccggctgca ccccacccac | 3840 |
| tacagcatca gatccaccct gcggatggaa ctgatgggct gcgacctgaa ctcctgcagc | 3900 |
| atgcctctgg gcatggaaag caaggccatc agcgacgccc agatcacagc cagcagctac | 3960 |
| ttcaccaaca tgttcgccac ctggtccccc tccaaggcca ggctgcacct gcagggccgg | 4020 |
| tccaacgcct ggcggcctca ggtgaacaac cccaaagaat ggctgcaggt ggactttcag | 4080 |
| aaaaccatga aggtgaccgg cgtgaccacc cagggcgtga aaagcctgct gaccagcatg | 4140 |
| tacgtgaaag agtttctgat cagcagcagc caggacggcc accagtggac cctgttctttt | 4200 |
| cagaacggca aggtgaaagt gttccagggc aaccaggact ccttcacccc cgtggtgaac | 4260 |
| tccctggacc ccccccctgct gacccgctac ctgcggatcc accccccagtc ttgggtgcac | 4320 |
| cagatcgccc tgaggatgga agtgctggga tgtgaggccc aggatctgta ctga | 4374 |

<210> SEQ ID NO 12
<211> LENGTH: 2351
<212> TYPE: PRT
<213> ORGANISM: Homo sapiens

<400> SEQUENCE: 12

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
```

```
            260                 265                 270
Tyr Trp His Val Ile Gly Met Gly Thr Thr Pro Glu Val His Ser Ile
            275                 280                 285
Phe Leu Glu Gly His Thr Phe Leu Val Arg Asn His Arg Gln Ala Ser
            290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                    325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asp Asn Ser
            370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                    405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
            435                 440                 445
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                    485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
            530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                    565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
            595                 600                 605
Asn Ile Gln Arg Phe Leu Pro Asn Pro Ala Gly Val Gln Leu Glu Asp
            610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                    645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
            675                 680                 685
```

```
Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
                995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095
```

```
Lys Lys Glu Gly Pro Ile Pro Pro Asp Ala Gln Asn Pro Asp Met
1100            1105            1110

Ser Phe Phe Lys Met Leu Phe Leu Pro Glu Ser Ala Arg Trp Ile
1115            1120            1125

Gln Arg Thr His Gly Lys Asn Ser Leu Asn Ser Gly Gln Gly Pro
1130            1135            1140

Ser Pro Lys Gln Leu Val Ser Leu Gly Pro Glu Lys Ser Val Glu
1145            1150            1155

Gly Gln Asn Phe Leu Ser Glu Lys Asn Lys Val Val Val Gly Lys
1160            1165            1170

Gly Glu Phe Thr Lys Asp Val Gly Leu Lys Glu Met Val Phe Pro
1175            1180            1185

Ser Ser Arg Asn Leu Phe Leu Thr Asn Leu Asp Asn Leu His Glu
1190            1195            1200

Asn Asn Thr His Asn Gln Glu Lys Lys Ile Gln Glu Glu Ile Glu
1205            1210            1215

Lys Lys Glu Thr Leu Ile Gln Glu Asn Val Val Leu Pro Gln Ile
1220            1225            1230

His Thr Val Thr Gly Thr Lys Asn Phe Met Lys Asn Leu Phe Leu
1235            1240            1245

Leu Ser Thr Arg Gln Asn Val Glu Gly Ser Tyr Asp Gly Ala Tyr
1250            1255            1260

Ala Pro Val Leu Gln Asp Phe Arg Ser Leu Asn Asp Ser Thr Asn
1265            1270            1275

Arg Thr Lys Lys His Thr Ala His Phe Ser Lys Lys Gly Glu Glu
1280            1285            1290

Glu Asn Leu Glu Gly Leu Gly Asn Gln Thr Lys Gln Ile Val Glu
1295            1300            1305

Lys Tyr Ala Cys Thr Thr Arg Ile Ser Pro Asn Thr Ser Gln Gln
1310            1315            1320

Asn Phe Val Thr Gln Arg Ser Lys Arg Ala Leu Lys Gln Phe Arg
1325            1330            1335

Leu Pro Leu Glu Glu Thr Glu Leu Glu Lys Arg Ile Ile Val Asp
1340            1345            1350

Asp Thr Ser Thr Gln Trp Ser Lys Asn Met Lys His Leu Thr Pro
1355            1360            1365

Ser Thr Leu Thr Gln Ile Asp Tyr Asn Glu Lys Glu Lys Gly Ala
1370            1375            1380

Ile Thr Gln Ser Pro Leu Ser Asp Cys Leu Thr Arg Ser His Ser
1385            1390            1395

Ile Pro Gln Ala Asn Arg Ser Pro Leu Pro Ile Ala Lys Val Ser
1400            1405            1410

Ser Phe Pro Ser Ile Arg Pro Ile Tyr Leu Thr Arg Val Leu Phe
1415            1420            1425

Gln Asp Asn Ser Ser His Leu Pro Ala Ala Ser Tyr Arg Lys Lys
1430            1435            1440

Asp Ser Gly Val Gln Glu Ser Ser His Phe Leu Gln Gly Ala Lys
1445            1450            1455

Lys Asn Asn Leu Ser Leu Ala Ile Leu Thr Leu Glu Met Thr Gly
1460            1465            1470

Asp Gln Arg Glu Val Gly Ser Leu Gly Thr Ser Ala Thr Asn Ser
1475            1480            1485

Val Thr Tyr Lys Lys Val Glu Asn Thr Val Leu Pro Lys Pro Asp
```

-continued

```
            1490                1495                1500
Leu Pro Lys Thr Ser Gly Lys Val Glu Leu Leu Pro Lys Val His
    1505                1510                1515
Ile Tyr Gln Lys Asp Leu Phe Pro Thr Glu Thr Ser Asn Gly Ser
    1520                1525                1530
Pro Gly His Leu Asp Leu Val Glu Gly Ser Leu Leu Gln Gly Thr
    1535                1540                1545
Glu Gly Ala Ile Lys Trp Asn Glu Ala Asn Arg Pro Gly Lys Val
    1550                1555                1560
Pro Phe Leu Arg Val Ala Thr Glu Ser Ser Ala Lys Thr Pro Ser
    1565                1570                1575
Lys Leu Leu Asp Pro Leu Ala Trp Asp Asn His Tyr Gly Thr Gln
    1580                1585                1590
Ile Pro Lys Glu Glu Trp Lys Ser Gln Glu Lys Ser Pro Glu Lys
    1595                1600                1605
Thr Ala Phe Lys Lys Lys Asp Thr Ile Leu Ser Leu Asn Ala Cys
    1610                1615                1620
Glu Ser Asn His Ala Ile Ala Ala Ile Asn Glu Gly Gln Asn Lys
    1625                1630                1635
Pro Glu Ile Glu Val Thr Trp Ala Lys Gln Gly Arg Thr Glu Arg
    1640                1645                1650
Leu Cys Ser Gln Asn Pro Pro Val Leu Lys Arg His Gln Arg Glu
    1655                1660                1665
Ile Thr Arg Thr Thr Leu Gln Ser Asp Gln Glu Glu Ile Asp Tyr
    1670                1675                1680
Asp Asp Thr Ile Ser Val Glu Met Lys Lys Glu Asp Phe Asp Ile
    1685                1690                1695
Tyr Asp Glu Asp Glu Asn Gln Ser Pro Arg Ser Phe Gln Lys Lys
    1700                1705                1710
Thr Arg His Tyr Phe Ile Ala Ala Val Glu Arg Leu Trp Asp Tyr
    1715                1720                1725
Gly Met Ser Ser Ser Pro His Val Leu Arg Asn Arg Ala Gln Ser
    1730                1735                1740
Gly Ser Val Pro Gln Phe Lys Lys Val Val Phe Gln Glu Phe Thr
    1745                1750                1755
Asp Gly Ser Phe Thr Gln Pro Leu Tyr Arg Gly Glu Leu Asn Glu
    1760                1765                1770
His Leu Gly Leu Leu Gly Pro Tyr Ile Arg Ala Glu Val Glu Asp
    1775                1780                1785
Asn Ile Met Val Thr Phe Arg Asn Gln Ala Ser Arg Pro Tyr Ser
    1790                1795                1800
Phe Tyr Ser Ser Leu Ile Ser Tyr Glu Glu Asp Gln Arg Gln Gly
    1805                1810                1815
Ala Glu Pro Arg Lys Asn Phe Val Lys Pro Asn Glu Thr Lys Thr
    1820                1825                1830
Tyr Phe Trp Lys Val Gln His His Met Ala Pro Thr Lys Asp Glu
    1835                1840                1845
Phe Asp Cys Lys Ala Trp Ala Tyr Phe Ser Asp Val Asp Leu Glu
    1850                1855                1860
Lys Asp Val His Ser Gly Leu Ile Gly Pro Leu Leu Val Cys His
    1865                1870                1875
Thr Asn Thr Leu Asn Pro Ala His Gly Arg Gln Val Thr Val Gln
    1880                1885                1890
```

```
Glu Phe Ala Leu Phe Phe Thr Ile Phe Asp Glu Thr Lys Ser Trp
    1895            1900                1905
Tyr Phe Thr Glu Asn Met Glu Arg Asn Cys Arg Ala Pro Cys Asn
    1910            1915                1920
Ile Gln Met Glu Asp Pro Thr Phe Lys Glu Asn Tyr Arg Phe His
    1925            1930                1935
Ala Ile Asn Gly Tyr Ile Met Asp Thr Leu Pro Gly Leu Val Met
    1940            1945                1950
Ala Gln Asp Gln Arg Ile Arg Trp Tyr Leu Leu Ser Met Gly Ser
    1955            1960                1965
Asn Glu Asn Ile His Ser Ile His Phe Ser Gly His Val Phe Thr
    1970            1975                1980
Val Arg Lys Lys Glu Glu Tyr Lys Met Ala Leu Tyr Asn Leu Tyr
    1985            1990                1995
Pro Gly Val Phe Glu Thr Val Glu Met Leu Pro Ser Lys Ala Gly
    2000            2005                2010
Ile Trp Arg Val Glu Cys Leu Ile Gly Glu His Leu His Ala Gly
    2015            2020                2025
Met Ser Thr Leu Phe Leu Val Tyr Ser Asn Lys Cys Gln Thr Pro
    2030            2035                2040
Leu Gly Met Ala Ser Gly His Ile Arg Asp Phe Gln Ile Thr Ala
    2045            2050                2055
Ser Gly Gln Tyr Gly Gln Trp Ala Pro Lys Leu Ala Arg Leu His
    2060            2065                2070
Tyr Ser Gly Ser Ile Asn Ala Trp Ser Thr Lys Glu Pro Phe Ser
    2075            2080                2085
Trp Ile Lys Val Asp Leu Leu Ala Pro Met Ile Ile His Gly Ile
    2090            2095                2100
Lys Thr Gln Gly Ala Arg Gln Lys Phe Ser Ser Leu Tyr Ile Ser
    2105            2110                2115
Gln Phe Ile Ile Met Tyr Ser Leu Asp Gly Lys Lys Trp Gln Thr
    2120            2125                2130
Tyr Arg Gly Asn Ser Thr Gly Thr Leu Met Val Phe Phe Gly Asn
    2135            2140                2145
Val Asp Ser Ser Gly Ile Lys His Asn Ile Phe Asn Pro Pro Ile
    2150            2155                2160
Ile Ala Arg Tyr Ile Arg Leu His Pro Thr His Tyr Ser Ile Arg
    2165            2170                2175
Ser Thr Leu Arg Met Glu Leu Met Gly Cys Asp Leu Asn Ser Cys
    2180            2185                2190
Ser Met Pro Leu Gly Met Glu Ser Lys Ala Ile Ser Asp Ala Gln
    2195            2200                2205
Ile Thr Ala Ser Ser Tyr Phe Thr Asn Met Phe Ala Thr Trp Ser
    2210            2215                2220
Pro Ser Lys Ala Arg Leu His Leu Gln Gly Arg Ser Asn Ala Trp
    2225            2230                2235
Arg Pro Gln Val Asn Asn Pro Lys Glu Trp Leu Gln Val Asp Phe
    2240            2245                2250
Gln Lys Thr Met Lys Val Thr Gly Val Thr Thr Gln Gly Val Lys
    2255            2260                2265
Ser Leu Leu Thr Ser Met Tyr Val Lys Glu Phe Leu Ile Ser Ser
    2270            2275                2280
```

```
Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Phe Ser Gln Asn Pro Pro Val Leu Lys Arg His Gln Arg
1               5                   10

<210> SEQ ID NO 14
<211> LENGTH: 24
<212> TYPE: PRT
<213> ORGANISM: Sus sp.

<400> SEQUENCE: 14

Ser Phe Ala Gln Asn Ser Arg Pro Pro Ser Ala Ser Ala Pro Lys Pro
1               5                   10                  15

Pro Val Leu Arg Arg His Gln Arg
            20

<210> SEQ ID NO 15
<211> LENGTH: 16
<212> TYPE: PRT
<213> ORGANISM: Sus sp.

<400> SEQUENCE: 15

Ser Phe Ser Gln Asn Ser Arg His Gln Ala Tyr Arg Tyr Arg Arg Gly
1               5                   10                  15
```

What is claimed is:

1. A method comprising:
   determining a first level of Factor VIII activity in a blood sample collected from a human subject diagnosed with Hemophilia A following administration of adeno-associated virus (AAV) particles comprising a polynucleotide encoding a Factor VIII protein to the human subject, and while the human subject is receiving an initial course of glucocorticoid steroid treatment;
   determining a second level of Factor VIII activity in a blood sample collected from the human subject after completion of the initial course of glucocorticoid steroid treatment;
   comparing the second level of Factor VIII activity to the first level of Factor VIII activity; and
   administering a tapering dose of the glucocorticoid steroid, wherein:
      when the second level of Factor VIII activity is not less than the first level of Factor VIII activity, a first tapering dose of the glucocorticoid steroid is administered over a time period of no more than three weeks; and
      when the second level of Factor VIII activity is less than the first level of Factor VIII activity, a second tapering dose of the glucocorticoid steroid is administered over a time period exceeding three weeks.

2. The method of claim 1, wherein administering the first tapering dose of the glucocorticoid steroid comprises:
   administering 20 mg of prednisolone or prednisone per day to the human subject, for 5 consecutive days immediately following completion of the initial course of glucocorticoid steroid treatment;
   administering 15 mg of prednisolone or prednisone per day to the human subject, for 3 consecutive days immediately following the 5 days on which the human subject was administered 20 mg of prednisolone or prednisone;
   administering 10 mg of prednisolone or prednisone per day to the human subject, for 3 consecutive days immediately following the 3 days on which the human subject was administered 15 mg of prednisolone or prednisone; and administering 5 mg of prednisolone or prednisone per day to the human subject, for 3 consecutive days immediately following the 3 days on which the human subject was administered 10 mg of prednisolone or prednisone.

3. The method of claim 2, wherein administering the second tapering dose of the glucocorticoid steroid comprises:

administering 30 mg of prednisolone or prednisone per day to the human subject, for 7 consecutive days immediately following completion of the initial course of glucocorticoid steroid treatment;

administering 20 mg of prednisolone or prednisone per day to the human subject, for 7 consecutive days immediately following the 7 days on which the human subject was administered 30 mg of prednisolone or prednisone;

administering 15 mg of prednisolone or prednisone per day to the human subject, for 5 consecutive days immediately following the 7 days on which the human subject was administered 20 mg of prednisolone or prednisone;

administering 10 mg of prednisolone or prednisone per day to the human subject, for 5 consecutive days immediately following the 5 days on which the human subject was administered 15 mg of prednisolone or prednisone; and administering 5 mg of prednisolone or prednisone per day to the human subject, for 5 consecutive days immediately following the 5 days on which the human subject was administered 10 mg of prednisolone or prednisone.

4. The method of claim 1, wherein administering the second tapering dose of the glucocorticoid steroid comprises:

administering 30 mg of prednisolone or prednisone per day to the human subject, for 7 consecutive days immediately following completion of the initial course of glucocorticoid steroid treatment;

administering 20 mg of prednisolone or prednisone per day to the human subject, for 7 consecutive days immediately following the 7 days on which the human subject was administered 30 mg of prednisolone or prednisone;

administering 15 mg of prednisolone or prednisone per day to the human subject, for 5 consecutive days immediately following the 7 days on which the human subject was administered 20 mg of prednisolone or prednisone;

administering 10 mg of prednisolone or prednisone per day to the human subject, for 5 consecutive days immediately following the 5 days on which the human subject was administered 15 mg of prednisolone or prednisone; and administering 5 mg of prednisolone or prednisone per day to the human subject, for 5 consecutive days immediately following the 5 days on which the human subject was administered 10 mg of prednisolone or prednisone.

5. A method comprising:

determining a first level of liver enzyme activity in a blood sample collected from a human subject diagnosed with Hemophilia A prior to administration of adeno-associated virus (AAV) particles comprising a polynucleotide encoding a Factor VIII protein to the human subject;

determining a second level of liver enzyme activity in a blood sample collected from the human subject after administration of AAV particles comprising a polynucleotide encoding a Factor VIII protein to the human, and after completion of an initial course of glucocorticoid steroid treatment;

comparing the second level of liver enzyme activity to the first level of liver enzyme activity; and administering a tapering dose of the glucocorticoid steroid, wherein:

when the second level of liver enzyme activity is not more than the first level of liver enzyme activity, a first tapering dose of the glucocorticoid steroid is administered over a time period of no more than three weeks; and when the second level of liver enzyme activity is greater than the first level of Factor VIII activity, a second tapering dose of the glucocorticoid steroid is administered over a time period exceeding three weeks.

6. The method of claim 5, wherein administering the first tapering dose of the glucocorticoid steroid comprises:

administering 20 mg of prednisolone or prednisone per day to the human subject, for 5 consecutive days immediately following completion of the initial course of glucocorticoid steroid treatment;

administering 15 mg of prednisolone or prednisone per day to the human subject, for 3 consecutive days immediately following the 5 days on which the human subject was administered 20 mg of prednisolone or prednisone;

administering 10 mg of prednisolone or prednisone per day to the human subject, for 3 consecutive days immediately following the 3 days on which the human subject was administered 15 mg of prednisolone or prednisone; and administering 5 mg of prednisolone or prednisone per day to the human subject, for 3 consecutive days immediately following the 3 days on which the human subject was administered 10 mg of prednisolone or prednisone.

7. The method of claim 6, wherein administering the second tapering dose of the glucocorticoid steroid comprises:

administering 30 mg of prednisolone or prednisone per day to the human subject, for 7 consecutive days immediately following completion of the initial course of glucocorticoid steroid treatment;

administering 20 mg of prednisolone or prednisone per day to the human subject, for 7 consecutive days immediately following the 7 days on which the human subject was administered 30 mg of prednisolone or prednisone;

administering 15 mg of prednisolone or prednisone per day to the human subject, for 5 consecutive days immediately following the 7 days on which the human subject was administered 20 mg of prednisolone or prednisone;

administering 10 mg of prednisolone or prednisone per day to the human subject, for 5 consecutive days immediately following the 5 days on which the human subject was administered 15 mg of prednisolone or prednisone; and administering 5 mg of prednisolone or prednisone per day to the human subject, for 5 consecutive days immediately following the 5 days on which the human subject was administered 10 mg of prednisolone or prednisone.

8. The method of claim 5, wherein administering the second tapering dose of the glucocorticoid steroid comprises:
- administering 30 mg of prednisolone or prednisone per day to the human subject, for 7 consecutive days immediately following completion of the initial course of glucocorticoid steroid treatment;
- administering 20 mg of prednisolone or prednisone per day to the human subject, for 7 consecutive days immediately following the 7 days on which the human subject was administered 30 mg of prednisolone or prednisone;
- administering 15 mg of prednisolone or prednisone per day to the human subject, for 5 consecutive days immediately following the 7 days on which the human subject was administered 20 mg of prednisolone or prednisone;
- administering 10 mg of prednisolone or prednisone per day to the human subject, for 5 consecutive days immediately following the 5 days on which the human subject was administered 15 mg of prednisolone or prednisone; and
- administering 5 mg of prednisolone or prednisone per day to the human subject, for 5 consecutive days immediately following the 5 days on which the human subject was administered 10 mg of prednisolone or prednisone.

* * * * *